United States Patent
Klimstra et al.

(10) Patent No.: US 6,172,069 B1
(45) Date of Patent: Jan. 9, 2001

(54) METHOD FOR PREVENTING OR REDUCING PHOTOSENSITIVITY AND OR PHOTOTOXICITY REACTION TO MEDICATIONS

(75) Inventors: Paul Dale Klimstra, Northbrook; Barbara Roniker, Chicago; Edward Allen Swabb, Kenilworth, all of IL (US)

(73) Assignee: G. D. Searle & Company, Chicago, IL (US)

( * ) Notice: Under 35 U.S.C. 154(b), the term of this patent shall be extended for 0 days.

(21) Appl. No.: 08/936,572

(22) Filed: Sep. 24, 1997

Related U.S. Application Data

(63) Continuation of application No. 08/438,002, filed on May 9, 1995, now abandoned, which is a continuation of application No. 08/188,296, filed on Jan. 28, 1994, now Pat. No. 5,668,134.

(51) Int. Cl.$^7$ .................................................. A61K 31/395
(52) U.S. Cl. ............................................................ 514/254
(58) Field of Search .............................................. 514/254

(56) References Cited

U.S. PATENT DOCUMENTS 4,528,287    7/1985    Itoh et al. .............................. 514/254

OTHER PUBLICATIONS

Kiyoshi Marutani, et al. "Reduced Phototoxicity of a Fluoroquinolone Antibacterial Agent with a Methoxy Group at the 8 Position in Mice Irradiated with Long–Wavelength UV Light", *Antimicrobial Agents and Chemotherapy*, vol. 37, No. 10, pp. 2217–2223, (1993).

R. Neringer "Lomefloxacin versus Norfloxacin in the Treatment of Uncomplicated Urinary Tract Infection Three–Day versus Seven–Day Treatment", *Scand. J. Infect.*, vol. 24, No. 6, pp. 773–780, (1992).

Keiichi Tozawa, et al. "A Clinical Study of Lomefloxacin on Patients with Urinary Tract Infections. Focused on Lomefloxacin–induced photosensitivity reaction", *Acta Urol. Jpn.*, vol. 39, pp. 801–805, (1993) *(English translation of Japanese article is attached).

Pierre Treffel, et al. "Chronopharmacokinetics of 5–Methoxypsoralen*", *Acta Derm. Venerol.*, vol. 70, No. 6, pp. 515–517, (1990).

William R. Bowie, et al. "Adverse Reactions in a Dose–Ranging Study with a New Long–Acting Fluoroquinolone, Fleroxacin", *Antimicrobial Agents and Chemotherapy*, vol. 33, No. 10, 1778–1782 (1989).

Hiromi Kumon, et al. "Once Daily Treatment with Sparfloxacin in Complicated Urinary Tract Infections: Clinical and Basic Comparative Studies on Morning and Evening Regimens," *Chemotherapy (Tokyo)* vol. 40, No. 1, pp. 40–59, (1992) *(English translation of Japanese article is attached).

Emad Rizk "A worldwide clinical overview of lomefloxacin, a once–daily fluoroquinolone", *International Journal of Antimicrobial Agents* 2 (1992) 67–68.

Eric Souetre, et al. "5–Methoxypsoralen Increases the Plasma Melatonin Levels in Humans," *The Journal of Investigative Dermatology*, 89(2), 152–55, (1987).

J. M. Sowden, et al. "Beth Puva at Home—A Novel Treatment for Psoriasis," *British Journal of Dermatology*, 127. Suppl. 40, 18–19, (1992).

Andreas E. Stuck, et al. "Fleroxacin Clinical Pharmacokinetics", *Clin. Pharmacokinet.* 22(2): 116–131 (1992).

*Primary Examiner*—James H. Reamer
(74) *Attorney, Agent, or Firm*—Fitzpatrick, Cella, Harper & Scinto

(57) ABSTRACT

The present invention provides a method for preventing or reducing a photosensitivity and/or phototoxicity reaction which may be caused by a once-per-day dose of a medication which causes a photosensitivity and/or phototoxicity reaction in a patient comprising administering the prescribed or suggested dose of the medication to the patient during the evening or early morning hours.

The present invention also provides an article of manufacture comprising: (1) a packaging material, and (2) a once-a-day dose medication which causes a photosensitivity and/or a phototoxicity reaction in a patient contained within said packaging material, wherein such a reaction is prevented or reduced by administering the medication to the patient during the evening or early morning hours, and wherein said packaging material comprises a label which indicates that such a reaction is prevented or reduced by administering the medication to the patient during the evening or early morning hours, and/or that such medication is to be administered during the evening or early morning hours, and/or wherein the packaging material is arranged in a manner which releases the medication to the patient during the evening or early morning hours.

54 Claims, 12 Drawing Sheets

METHOD FOR PREVENTING OR REDUCING PHOTOSENSITIVITY AND OR PHOTOXICITY REACTION TO MEDICATIONS

This application is a continuation of Application Ser. No. 08/438,002 filed May 9, 1995 which, now abondoned, is a continuation application of application Ser. No. 08/188,296, filed on Jan. 28, 1994 now U.S. Pat. No. 5,668,134.

BACKGROUND OF THE INVENTION

1. Field of the Invention

The present invention generally relates to a method for preventing or reducing a photosensitivity and/or phototoxicity reaction which may be caused by a once-per-day dose of an over-the-counter or prescription medication which causes a photosensitivity and/or phototoxicity reaction in a human or animal patient comprising administering the prescribed or suggested dose of the medication to the patient during the evening or early morning hours, between the hours of about 4:00 p.m. and about 4:00 a.m.

The present invention also generally relates to a method for administering a once-per-day dose of an over-the-counter or prescription medication which causes a photosensitivity and/or phototoxicity reaction to a human or animal patient in a manner which prevents or reduces such a reaction comprising administering the prescribed or suggested dose of the medication to the patient during the evening or early morning hours, between the hours of about 4:00 p.m. and about 4:00 a.m.

The present invention also generally relates to, in a method for administering a therapeutically effective amount of a once-a-day medication which medication in such a once-a-day therapeutic amount achieves a concentration in the blood which causes a photosensitivity and/or phototoxicity reaction in the patient to whom the medication is administered, an improvement in the method comprising administering the medication to the patient at a time sufficient for the blood level of such medication to be at a concentration which is less than a concentration which produces a photosensitivity and/or phototoxicity reaction during the daylight hours.

The present invention also generally relates to a method for treating an infection in a patient in a manner which prevents or reduces a photosensitivity and/or phototoxicity reaction which method comprises orally administering to the patient a once-a-day dose of about 25 mg to about 700 mg of lomefloxacin hydrochloride between the hours of about 4:00 p.m. and about 4:00 a.m.

The present invention also generally relates to an article of manufacture comprising: (1) a packaging material, and (2) a once-a-day dose of an over-the-counter or prescription medication which causes a photosensitivity and/or a phototoxicity reaction in a human or animal patient contained within said packaging material, wherein such a reaction is prevented or reduced by administering the medication to the patient during the evening or early morning hours, between the hours of about 4:00 p.m. and about 4:00 a.m., and wherein the packaging material comprises a label which indicates that such a reaction is prevented or reduced by administering the medication to the patient during the evening or early morning hours, between the hours of about 4:00 p.m. and about 4:00 a.m., and/or that such medication is to be administered between the hours of about 4:00 p.m. and about 4:00 a.m., and/or wherein the packaging material is arranged in a manner which releases the medication to the patient during the evening or early morning hours, between the hours of about 4:00 p.m. and about 4:00 a.m.

Deleterious reactions caused by sun exposure can be broadly classified into sunburns or chemically-induced photosensitivity reactions. The reactions produced by such interaction leads to erythema, fever and, at times, blisters similar to those produced by moderate to severe sunburn. Photoreactions may occur through light clothing, such as T-shirts or blouses.

The solar spectra that commonly affect human skin are UVB (ultraviolet B, 290 to 320 nm) and UVA (ultraviolet A, 320 to 400 nm). UVB is known as the "sunburn spectrum," which can cause burning, tanning, aging and carcinogenic changes in the skin. UVA is erythrogenic, but the amount of energy required to induce an erythemic effect is 1000 times greater than for UVB. It has been shown for most drugs associated with photosensitivity reactions that wavelengths from approximately 320 nm to approximately 400 nm (UVA) are most important for photoreactions. These reactions are evoked when UVA light energy is absorbed by an appropriate concentration of drug in the skin. The resulting photochemical reactions can damage cell membranes and lysosomes, and induce an exaggerated sunburn with intense redness, edema and occasionally blisters.

Sunburn is the result of the penetration of the skin by ultraviolet (UV) light, primarily the UVB light. An estimated 95% of UVB radiation reaching skin is absorbed.

The prolonged exposure to UVA light can produce mild burn and hyperpigmentation. UVA radiation penetrates well through the epidermis, but tends to tan more than burn the skin. However, UVA radiation which, while usually burning less, will provide a severe burn when an exposed individual has taken a sensitizing agent, such as a medication which causes a photosensitivity and/or phototoxicity reaction. UVA radiation is not limited to direct sun exposure. Cloud cover, shady areas, light through glass windows and/or car windows may still cause a photosensitivity reaction.

UVA radiation, which is commonly associated with drug-induced phototoxic or photoallergic reactions, has a relatively constant level during daylight hours. UVB radiation, on the other hand, which causes common sunburn, and is a dose-related risk for melanoma, has its strongest effect between 10:00 a.m. and 2:00 p.m. Thus, avoiding the sun between these hours may help to minimize ordinary sunburn, but may not have the same effect on drug-induced photoreactions.

Sunburn is a complex inflammatory process causing dyskeratotic cells, spongiosis, vacuolation of keratinocytes and edema from capillary leakage 12 to 24 hours after exposure to light (from the sun, or from artificial sources). Erythema is the most common symptom. Erythema is a prostaglandin-mediated vasodilary effect, an attempt to protect the epidermis and minimize further damage. At the cellular level of the skin, sun radiation has been shown to reduce the phospholipid content of the skin and alter its cholesterol, a substance which is a contributor to the stability of cell membranes. Sun radiation has also been shown to act on intracellular cell bodies known as lysosomes, which play an important role in controlling the conversion of the living cells of epidermis to horny (keratinized) material which is found as the protective outer layer of the skin. Destruction of lysosomes is believed to be responsible for prematurely keratinized cells. Substances discharged from damaged lysosomes may be responsible for characteristic symptoms of severe sunburn, such as dilation of the blood vessels and fever.

It is well known that numerous, different over-the-counter and prescription medications, including the quinolone class of antibiotics, in widespread use throughout the world today, can cause undesirable and, often, severe and painful photosensitivity and/or phototoxicity reactions in patients exposed to direct or indirect sunlight, or to artificial ultraviolet light. Many of the patients which have experienced such reactions have had to be hospitalized for several days as a result of such reactions, and have required i.v. therapy and other medications. Consequently, these medications, including all quinolone antibiotics, contain appropriate warnings concerning photosensitivity and/or phototoxicity reactions in their product labeling. Patients are advised to avoid excessive sunlight and artificial ultraviolet light while receiving these drugs, and to discontinue therapy if phototoxicity occurs.

In order for medications to cause photosensitivity and/or phototoxicity reactions, the skin has to be exposed to a specified radiation wave length band. The resulting reactions include acute, abnormal sunburn responses (blistered and/or peeling skin, edema, swelling of the face and/or limbs, rashes, first, second and/or third degree burns, itching, pain to the skin, eyes and/or joints, nausea, vomiting, diarrhea, fever, chills, confusion, protein in the urine, red, swollen, tearing and/or photophobic eyes, ulcers, etc.). A summary of commonly-used, commercially-available medications, the type of photoreaction caused thereby, as well as their action spectrum, is presented in Table 1 below.

TABLE 1

SYSTEMIC PHOTOSENSITIZERS

| Name | Type of Photoreaction | Action Spectrum (nm) |
|---|---|---|
| Sulfonamides | Phototoxic and photoallergic | 290–320 |
| Sulfonylureas (tolbutamide, chlorpropamide) | | 290–360 |
| Chlorothiazides | Phototoxic and photoallergic | 290–320 320–400 |
| Phenothiazines | Phototoxic, urticaria eruption, gray-blue hyperpigmentation | 290–400 |
| Antibiotics (tetracyclines, griseofulvin, nalidixic acid) | Phototoxic and photoallergic bullae | 320–400 |
| Furocoumarins (psoralens) | Phototoxic | |
| Nonsteroidal anti-inflammatory agents | Phototoxic and photoallergic | Unknown |
| Anticancer drugs (DTIC, fluorouracil, methotrexate, vinblastine) | Phototoxic | Unknown |
| Estrogens, progestins, and other drugs | Phototoxic, melasma | 290–320 |
| Chlordiazepoxide (Librium) | Photoallergic | 290–360 |
| Cyclamates | Phototoxic and photoallergic | 290–360 |
| Quinidine, quinine | Photoallergic | 320–400 |

Quinolone antibiotics are known to produce photoreactions, which are primarily phototoxic in nature, in humans and in animals.

MAXAQUIN® (lomefloxacin hydrochloride), which is available from G. D. Searle & Co. (Skokie, Ill.), as well as all marketed quinolones, exhibits a dose-dependent, drug-induced, UVA required photosensitivity reaction. The most clinically-relevant human serum levels for lomefloxacin HCl are approximately 0.2 to approximately 5 micrograms per ml of plasma.

Until recently, the mechanism of photoreactions of quinolones were considered unknown. A number of in vitro studies have now been reported on the mechanism of quinolones, including lomefloxacin hydrochloride. Reaction of quinolones in the skin with UVA light may generate singlet oxygen, free radicals or other toxic by-products. These substances, in turn, bind to cellular DNA leading to lipid peroxidation, a critical event in photo-induced cellular lysis.

There clearly exists a need for a method for preventing or reducing a photosensitivity and/or phototoxicity reaction which may be caused by an over-the-counter or prescription medication which causes a photosensitivity and/or phototoxicity reaction in a patient.

Until the discovery of the present invention, in order to reduce the incidence rate and severity of photosensitivity and/or phototoxicity reactions, such as to over-the-counter and prescription medications which cause photosensitivity and/or phototoxicity reactions, for example lomefloxacin hydrochloride, patients for which these medications were prescribed had to minimize their exposure to UVA radiation by wearing appropriate clothing, and by applying suntan creams with high SPF and effective blockage of UVA radiation. In addition, patients had to be careful to minimize their exposure to direct or indirect sunlight during, and for a few days after, receiving medications such as MAXAQUIN®.

It has now been discovered that a method for preventing or reducing photosensitivity and/or phototoxicity reactions in patients for which over-the-counter and/or prescription medications which cause photosensitivity and/or phototoxicity reactions, such as MAXAQUIN®, have been prescribed is through the reduction of the concentration of the medication in the blood and, consequently, in the skin, during the high UVA and/or UVB radiation periods. This can be achieved by administering a single daily dose of the medication to the patients during the evening, or during the early morning hours, preferably before 4:00 a.m., and more preferably just before dinner.

2. Description of the Related Art

U.S. Pat. No. 4,528,287, which is incorporated herein by reference, discloses piperazinyl-quinoline-3-carboxylic acids, pharmaceutically-acceptable salts thereof, a process for preparing them, and a pharmaceutical composition which contains these compounds as an active ingredient.

The concept of administering medications in a manner which minimizes skin levels of drug during periods of peak daily sunlight is novel, and is not known to be discussed in the literature.

There are generally no specific instructions given to a patient concerning the time of day during which a patient should take his once-a-day medication. Generally, once-a-day medications are described and/or prescribed and/or recommended for use in terms of a "daily," rather than an "evening," dose. See, for example, the dosage information for MAXAQUIN® which is present in the *Physician's Desk Reference* (47th Edition, Medical Economics Data, Montrale, N.J., 1993), which is described in terms of a "daily" dose. By convention, most once-a-day medications are taken in the late morning hours (between the hours of 6:00 a.m. and 11:00 a.m.), generally before, with, or just after, breakfast.

SUMMARY OF THE INVENTION

The present invention provides a method for preventing or reducing a photosensitivity and/or phototoxicity reaction which may be caused by a once-per-day dose of an over-the-counter or prescription medication which causes a photosensitivity and/or phototoxicity reaction in a human or animal patient by administering the prescribed or suggested dose of the medication to the patient during the evening or early morning hours, between the hours of about 4:00 p.m. and about 4:00 a.m.

The present invention also provides a method for administering a once-per-day dose of an over-the-counter or prescription medication which causes a photosensitivity and/or phototoxicity reaction to a human (adult or child) or animal patient in a manner which prevents or reduces such a reaction by administering the prescribed or suggested dose of the medication to the patient during the evening or early morning hours, generally between the hours of about 4:00 p.m. and about 4:00 a.m., preferably just prior to dinner.

The present invention also provides, in a method for administering a therapeutically effective amount of a once-a-day medication which medication in such a once-a-day therapeutic amount achieves a concentration in the blood which causes a photosensitivity and/or phototoxicity reaction in the patient to whom the medication is administered, an improvement in the method comprising administering the medication to the patient at a time sufficient for the blood level of such medication to be at a concentration which is less than a concentration which produces a photosensitivity and/or phototoxicity reaction during the daylight hours of between about 6:00 a.m. and about 7:00 p.m.

The present invention also provides a method for treating an infection in a patient in a manner which prevents or reduces a photosensitivity and/or phototoxicity reaction which comprises orally administering to the patient a once-a-day dose of about 25 mg to about 700 mg of lomefloxacin hydrochloride between the hours of about 4:00 p.m. and about 4:00 a.m.

The present invention also provides an article of manufacture comprising: (1) a packaging material, and (2) a once-a-day dose of an over-the-counter or prescription medication which causes a photosensitivity and/or a phototoxicity reaction in a human or animal patient contained within said packaging material, wherein such a reaction is prevented or reduced by administering the medication to the patient during the evening or early morning hours, between the hours of about 4:00 p.m. and about 4:00 a.m., and wherein said packaging material comprises a label which indicates that such a reaction is prevented or reduced by administering the medication to the patient during the evening or early morning hours, between the hours of about 4:00 p.m. and about 4:00 a.m., and/or that such medication is to be administered between the hours of about 4:00 p.m. and about 4:00 a.m., and/or wherein the packaging material is arranged in a manner which releases the medication to the patient during the evening or early morning hours, between the hours of about 4:00 p.m. and about 4:00 a.m.

BRIEF DESCRIPTION OF THE DRAWINGS

FIG. 2 represents observations made during the first 24 hours after radiation.

FIG. 2 shows that the increase in photosensitivity (as indicated by the statistically significant decrease in Minimum Erythema Dose, p=0.002) observed with morning dosing of lomefloxacin hydrochloride was significant, while no changes in sensitivity to radiation was observed with evening dosing of lomefloxacin hydrochloride.

FIG. 3 shows the magnitude of change in photosensitivity between morning and evening dosing, as observed during the first 24 hours after radiation.

FIG. 4 represents observations made during 24–72 hours after radiation.

FIG. 4 shows that the increase in photosensitivity (indicated by the decrease in Minimum Erythema Dose) observed with morning dosing of lomefloxacin hydrochloride was significant, while no changes in sensitivity to radiation were observed with evening dosing.

FIG. 5 shows the magnitude of change in photosensitivity between morning and evening dosing, as observed during 24–72 hours after radiation.

FIG. 6 is a plot of the percent (0% to 100%) of the subjects (N=13) with edema or blisters versus time (in hours) after UVA irradiation. The a.m. dosing group is represented with diagonal-lined areas, and the p.m. dosing group is represented with fully blackened areas. The asterisk (*) in FIG. 6 indicates that no edema or blisters were observed at any of the evaluation times described hereinbelow in Example 5 after the p.m. dose.

FIG. 6 shows the degree of severity of reactions to the UVA light radiation. Edema and blisters, if present, were indications of severity. Edema and blisters were observed only with radiation which followed a.m. dosing.

FIG. 7 shows the correlation between lomefloxacin hydrochloride plasma concentration, which is similar to lomefloxacin hydrochloride skin concentration, and changes in skin sensitivity to light. FIG. 7 shows that when the concentration of lomefloxacin hydrochloride is high, there is a marked reduction in Minimum Erythema Dose from baseline, i.e., there is a significant risk of a photoreaction when exposed to VA radiation.

FIG. 8 shows the correlation between lomefloxacin hydrochloride plasma concentration, which is similar to lomefloxacin hydrochloride skin concentration, and changes in skin sensitivity to light. FIG. 8 shows that when the concentration of lomefloxacin hydrochloride is low, there is no reduction in Minimum Erythema Dose from baseline, i.e., the risk of a photoreaction is minimized.

FIG. 9 represents observations made during the first 24 hours after radiation.

FIG. 9 shows that there was no increase in photosensitivity observed with either morning or evening dosing of lomefloxacin hydrochloride, when UVA plus UVB radiation was employed. The amount of UVA+UVB radiation to give MED is over 100 times less than for UVA radiation alone, as is seen from comparing MED values in FIGS. 2 and 9. FIG. 9 shows that adding the sun-burning effect of UVB radiation overshadows the effect of UVA radiation.

FIG. 10 shows the magnitude of change in photosensitivity between morning and evening dosing observed during the first 24 hours after radiation.

FIG. 11 represents observations made during 24–72 hours after radiation.

FIG. 11 shows that there was no increase in photosensitivity observed with either morning or evening dosing of lomefloxacin hydrochloride, when UVA plus UVB radiation was employed. FIG. 11 shows that adding the sun-burning effect of UVB radiation overshadows the effect of UVA radiation.

FIG. 12 shows the magnitude of change in photosensitivity between morning and evening dosing observed during the first 24 hours after radiation.

DETAILED DESCRIPTION OF THE INVENTION

(1) Definitions

Figure 1:
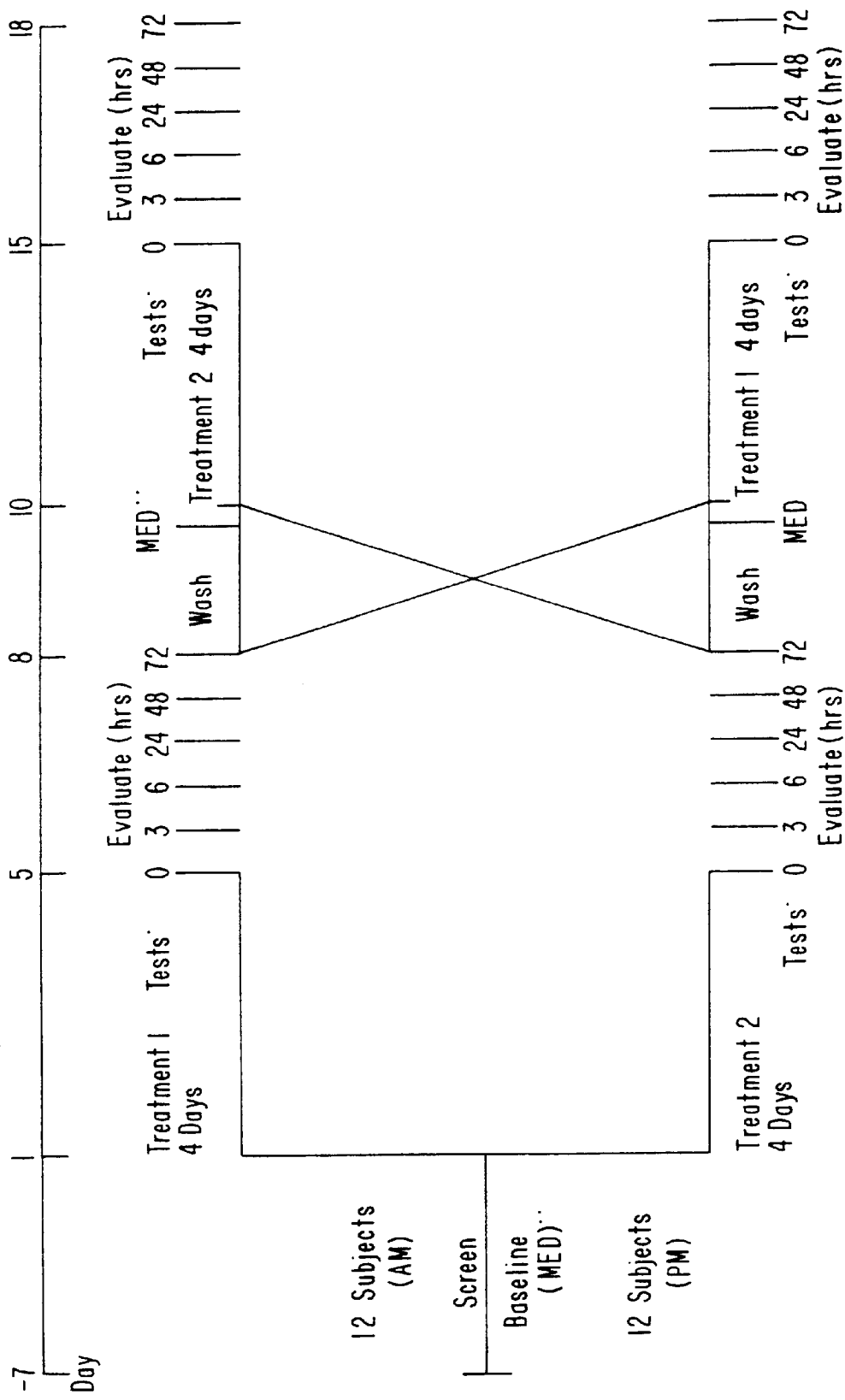
FIG. 1 shows the design of the study described in detail hereinbelow in Example 5.

For purposes of clarity, the terms and phrases used throughout this specification and the appended claims are defined in the manner set forth directly below.

The abbreviation "AUC" as used herein means "Area Under the Curve," which is the value of the amount of medication in the serum at a given point in time (ng.ml⁻¹.hours). It is calculated using the standard trapezoidal rule and the following mathematical formula:

$$\text{Area Under the Curve (AUC)} = \frac{(C_1 + C_2)}{2} \times (t_2 - t_1),$$

where $C_1$ represents the first concentration, $C_2$ represents the second concentration, $t_1$ represents the first time and $t_2$ represents the second time.

The abbreviation "BID" as used herein means twice a day.

The abbreviation "$C_{max}$" as used herein means maximum concentration of medication in the serum (ng/ml).

The abbreviation "$C_{min}$" as used herein means minimum concentration of medication in the serum (ng/ml).

The abbreviation "CRF" as used herein means case report form.

The abbreviation "H" as used herein means hours.

The phrase "half-life" as used herein means the amount of time it takes for 50% of a medication to be lost through biological processes.

The term "joule" as used herein means the amount of radiation energy (UVA and/or UVB) given, in J/cm².

The abbreviation "MED" as used herein means Minimum Erythema Dose, which is the smallest dose of irradiation, UVA and/or UVB, causing erythema of a predetermined area of skin, such as a one square centimeter (1 cm²) patch of skin.

The abbreviation "N" as used herein indicates the number of times a particular experiment was conducted. For example, (N=3) means that a particular experiment was conducted three times.

The abbreviation "NE" as used herein indicates that minimal erythema dose was not established, even at the highest exposure level.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, aerosol, solvent or encapsulating material, involved in carrying or transporting a chemical compound or pharmaceutical agent from one organ, or portion of the body, to another organ, or portion of the body.

The abbreviation "q.d." as used herein means once a day.

The abbreviation "SPF" as used herein means sun protection factor, and is calculated as follows:

$$SPF = \frac{\text{MED of the Sunscreen – Protected Skin}}{\text{MED of the Nonprotected Skin}}.$$

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The abbreviation "$T_{1/2}$" as used herein means half-life.

The abbreviation "$T_{max}$" as used herein means time when plasma concentration of drug reaches a maximum value.

(2) Description of the Invention

The present invention provides a method for preventing or reducing a photosensitivity and/or phototoxicity reaction which may be caused by a once-per-day dose of an over-the-counter or prescription medication which causes a photosensitivity and/or phototoxicity reaction in a human or animal patient comprising administering the prescribed or suggested dose of the medication to the patient during the evening or early morning hours, between the hours of about 4:00 p.m. and about 4:00 a.m., rather than during the late morning or afternoon hours.

The present invention also provides a method for administering a once-per-day dose of an over-the-counter or prescription medication which causes a photosensitivity and/or phototoxicity reaction to a human (adult or child) or animal (mammal or non-mammal) patient in a manner which prevents or reduces such a reaction comprising administering the prescribed or suggested dose of the medication to the patient during the evening or early morning hours, generally between the hours of about 4:00 p.m. and about 4:00 a.m., preferably just prior to dinner, rather than during the late morning or afternoon hours.

The present invention also provides, in a method for administering a therapeutically effective amount of a once-a-day medication which medication in such a once-a-day therapeutic amount achieves a concentration in the blood which causes a photosensitivity and/or phototoxicity reaction in the patient to whom the medication is administered, an improvement in the method comprising administering the medication to the patient at a time sufficient for the blood level of such medication to be at a concentration which is less than a concentration which produces a photosensitivity and/or phototoxicity reaction during the daylight hours of between about 6:00 a.m. and about 7:00 p.m., particularly between the hours of about 9:00 a.m. and about 5:00 p.m., and most particularly between the hours of about 10:00 a.m. and about 2:00 p.m.

The present invention also provides a method for treating an infection in a patient which method comprises orally administering to the patient a once-a-day dose of about 25 mg to about 700 mg, preferably about 100 to 500 mg, more preferably about 150 to 450 mg, and most preferably 200 or 400 mg, of lomefloxacin hydrochloride during the evening or early morning hours, between the hours of about 4:00 p.m. and about 4:00 a.m., rather than during the late morning or afternoon hours.

The present invention also provides an article of manufacture comprising: (1) a packaging material, and (2) a once-a-day dose of an over-the-counter or prescription medication which causes a photosensitivity and/or a phototoxicity reaction in a human or animal patient contained within said packaging material, wherein such a reaction is prevented or reduced by administering the medication to the patient during the evening or early morning hours, between the hours of about 4:00 p.m. and about 4:00 a.m., and wherein said packaging material comprises a label which indicates that such a reaction is prevented or reduced by administering the medication to the patient during the evening or early morning hours, between the hours of about 4:00 p.m. and about 4:00 a.m., and/or that such medication is to be administered between the hours of about 4:00 p.m. and about 4:00 a.m., and/or wherein the packaging material is arranged in a manner which releases the medication to the patient during the evening or early morning hours, between the hours of about 4:00 p.m. and about 4:00 a.m.

Generally, when medications which cause a phototoxicity and/or photosensitivity reaction are administered during the evening, or early morning, hours, rather than during the late morning or afternoon hours, blood and, consequently, skin levels of medication will be low the next day during the peak hours for sunlight and ultraviolet radiation. Thus, these low blood levels of medication will generally minimize the incidence and severity of photosensitivity and/or phototoxic reactions in patients to which these photosensitivity and/or phototoxicity causing medications are administered.

The methods of the present invention may be employed with any once-a-day dose over-the-counter or prescription medication which causes a photosensitivity and/or phototoxicity reaction. Because dosing of the medication takes place in the evening, or early morning, hours, there will generally be a lower, but sufficient for the desired pharmacological indicated property, concentration of medication in the patient's blood and, consequently, in the patient's skin during the peak sunlight hours of the daytime. Thus, photosensitivity and/or phototoxicity reactions which would generally be caused by these medications will be reduced or eliminated.

A variety of different commercially-available drugs may be employed in the methods of the present invention including, but not limited to, antimicrobial agents, such as pentamidine, lomefloxacin, metronidazole, fungistatic agents, germicidal agents, hormones, antipyretic agents, antidiabetic agents, bronchodilators, such as aminophylline, antidiarrheal agents, such as diphenoxylate hydrochloride with atropine sulfate, antiarrhythmic agents, such as disopyramide phosphate and bidisomide, coronary dilation agents, glycosides, spasmolytics, antihypertensive agents, such as verapamil and verapamil hydrochloride and their enantiomers, and betaxolol, antidepressants, antianxiety agents, other psychotherapeutic agents, such as zolpidem, cycloserine and milacemide, corticosteroids, analgesics, such as misoprostol with diclofenac, contraceptives, such as ethynodiol diacetate with ethinyl estradiol, and norethynodrel with mestranol, nonsteroidal anti-inflammatory drugs, such as oxaprozen, blood glucose lowering agents, cholesterol lowering agents, anticonvulsant agents, other antiepileptic agents, immunomodulators, antioholinergics, sympatholytics, sympathomimetics, vasodilatory agents, anticoagulants, antiarrhythmics, such as disopyramide or disobutamide, prostaglandins having various pharmacologic activities, such as misoprostol and enisoprost, diuretics, such as spironolactone and spironolactone with hydrochlorothiazide, sleep aids, such as zolpidem tartrate, antihistaminic agents, antineoplastic agents, oncolytic agents, antiandrogens, antimalarial agents, antileprosy agents, and various other types of drugs. See Goodman and Gilman's *The Basis of Therapeutics* (Eighth Edition, Pergamon Press, Inc., USA, 1990) and *The Merck Index* (Eleventh Edition, Merck & Co., Inc., USA, 1989), each of which is incorporated herein by reference.

Photosensitivity and/or phototoxicity reactions have been documented to be associated with all of the following commercially-available, over-the-counter or prescription medications, each of which is contemplated for use in the methods of the present invention: Avobenzene/padimate-O, ACCUPRIL® tablets (quinapril hydrochloride), Accutane capsules (isotretinoin), Achromycin V capsules (the monohydrochloride of (4S-(4α, 4aα,5aα,6β, 12aα,))-4-(dimethylamino)-1,4,4a,5,5a,6,11,12a-octahydro-3,6,10,12,12a-pentahydroxy-6-methyl-1,11-dioxo-2-naphthacenecarboxamide), Actifed cough syrup (codeine phosphate, triprolidine hydrochloride and pseudoephedrine hydrochloride), Aldactazide tablets (spironolactone and hydrochlorothiazide), ALDOCLOR® tablets (methyldopa and chlorothiazide), Aldoril tablets (methyldopa-hydrochlorothiazide), Alferon® N injection (interferon α-n3 (human leukocyte derived)), ALTACE™ capsules (ramipril), AMBIEN® tablets (zolpidem tartrate), Anafranil capsules (clomipramine hydrochloride), ANAPROX® tablets (naproxen sodium), Ancobon capsules (flucytosine), Ansaid tablets (flurbiprofen), Apresazide capsules (hydralazine hydrochloride and hydrochlorothiazide), Asendin tablets (2-chloro-11-(1-piperazinyl)dibenz(b,f)(1,4)-oxazepine), Atretol™ tablets (carbamazepine), Aureomycin ophthalmic ointment (chlortetracycline hydrochloride), Azo Gantanol® tablets (sulfamethoxazole and phenazopyridine hydrochloride), Azo Gantrisin tablets (sulfisoxazole and phenazopyridine hydrochloride), Azulfidine® tablets and EN-tabs (5-((p-(2-pyridylsulfamoyl)phenyl)-azo)salicylic acid), Bactrim tablets (trimethoprim and sulfamethoxazole), Bactrim I.V. infusion (trimethoprim and sulfamethoxazole), Bactrim pediatric suspension (trimethoprim and sulfamethoxazole), Bactrim suspension (trimethoprim and sulfamethoxazole), Bactrim tablets (trimethoprim and sulfamethoxazole), Benadryl® capsules (diphenhydramine hydrochloride USP), Benadryl® kapseals (diphenhydramine hydrochloride USP), Benadryl® tablets (diphenhydramine hydrochloride USP), Benadryl® parenteral (diphenhydramine hydrochloride USP), Benadryl® steri-vials, ampoules, and steri-dose syringe (diphenhydramine hydrochloride USP), Capoten tablets (captopril), Capozide tablets (captopril-hydrochlorothiazide), Cardizem® CD capsules (diltiazem hydrochloride), Cardizem® SR capsules (diltiazem hydrochloride), Cardizem® tablets (diltiazem hydrochloride), Chibroxin sterile ophthalmic solution (with oral form) (norfloxacin), Children's Advil® suspension (ibuprofen), Cipro® I.V. (ciprofloxacin), Cipro® tablets (ciprofloxacin), Claritin tablets (loratadine), Clinoril tablets (sulindac), Combipres® tablets (clonidine hydrochloride and chlorthalidone), Compazine® injection (prochlorperazine maleate), Compazine® multi-dose vials (prochlorperazine maleate), Compazine® syringes (prochlorperazine maleate), Compazine® spansule capsules (prochlorperazine maleate), Compazine® suppositories (prochlorperazine maleate), Compazine® syrup (prochlorperazine maleate), Compazine® tablets (prochlorperazine maleate), Cordarone tablets (amiodarone hydrochloride), Corzide tablets (nadolol and bendroflumethiazide), Dantrium capsules (dantrolene sodium), Dapsone tablets (4-4' diaminodiphenylsulfone), DAYPRO® caplets (oxaproxin), Declomycin tablets (demeclacycline or (4S-(4α,4aα,5aα,6β,12aα))-7-Chloro-4-dimethylamino)-1,4,4a,5,5a,6,11,12a-octahydro-3,6,10,12,12a-pentahydroxy-1,11-dioxo-2-naphthacenecarboxamide monohydrochloride), DECONAMINE® capsules (chlorpheniramine maleate and d-psuedoephedrine hydrochloride), DECONAMINE® syrup (chlorpheniramine maleate and d-psudoephedrine hydrochloride), DECONAMINE® tablets (chlorpheniramine maleate and d-psudoephedrine hydrochloride), Depakene capsules (valproic acid), Depakene syrup (valproic acid), Depakote sprinkle capsules (divalproex sodium), Depakote tablets (divalproex sodium), DiaBeta® tablets (glyburide), Diabinese tablets (chlorpropamide), Diamox parenteral (acetazolamide), Diamox sequels (acetazolamide), Diamox tablets (acetazolamide), Dimetane-DC cough syrup (brompheniramine maleate, phenylpropanolamine hydrochloride and codeine phosphate), Dimetane-DX cough syrup (brompheniramine maleate, phenylpropanolamine hydrochloride and codeine phosphate), Dipentum® capsules (olsalazine sodium), Diucardin tablets (hydroflumethiazide), Diupres tablets (reserpine and chlorothiazide), Diuril oral suspension (chlorothiazide), Diuril sodium intravenous (chlorothiazide), Diuril tablets (chlorothiazide), Dolobid tablets (diflunisal), DORYX® capsules (doxycycline hyclate), Dyazide capsules (hydrochlorothiazide and triamterene), Dyrenium capsules (triamterene), Efudex cream (5-fluorouracil), Efudex solutions (5-fluorouracil), Elavil injection (amitriptyline HCl), Elavil tablets (amitriptyline HCl), Eldepryl tablets (selegiline hydrochloride), Endep tablets (amitriptyline HCl), Enduron tablets (methyclothiazide), Enduronyl Forte tablets (methyclothiazide and deserpidine), Enduronyl tablets (methyclothiazide and deserpidine), Ergamisol tablets (levamisole hydrochloride), Esidrix tablets (hydrochlorothiazide USP), Esimil tablets (guanethidine monosulfate USP and hydrochlorothiazide USP), Etrafon Forte tablets (perphenazine, USP and amitriptyline hydrochloride, USP), Etrafon 2–10 tablets (perphenazine, USP and amitriptyline hydrochloride, USP), Etrafon tablets (perphenazine, USP and amitriptyline hydrochloride, USP), Etrafon-A tablets (perphenazine, USP and amitriptyline hydrochloride, USP), Eulexin capsules (flutamide), Exna tablets (benzthiazide), FUDR injection (floxuridine), Fansidar tablets (N1-(5,6-dimethoxy-4-pyrimidinyl) sulfanilamide (sulfadoxine) and 2,4-diamino-5-(p-chlorophenyl)-6-ethylpyrimidine (pyrimethamine), Feldene capsules (piroxicam), Flexeril tablets (cyclobenzaprine hydrochloride), FLOXIN® I.V. (ofloxacin injection), FLOXINS® tablets (ofloxacin), Fluorouracil injection (5-fluoro-2,4 (1H,3H)-pyrimidinedione), Fulvicin tablets (griseofulvin), Gantanol® suspension (sulfamethoxazole), Gantanol® tablets (sulfamethoxazole), Gantrisin ophthalmic ointment/solution (sulfisoxazole), Gantrisin pediatric suspension (sulfisoxazole), Gantrisin syrup (sulfisoxazole), Gantrisin tablets (sulfisoxazole), Glucotrol tablets (glipizide), Glynase PresTab tablets (glyburide), Grifulvin V tablets (griseofulvin), Grifulvin oral suspension (griseofulvin), Gristactin capsules (griseofulvin), Grisactin tablets (griseofulvin), Gris-PEG tablets (griseofulvin), Grivate tablets (griseofulvin), Grivate suspension (griseofulvin), Haldol Decanoate 50 injection (haloperidol decanoate), Haldol Decanoate 100 injection (haloperidol decanoate), Haldol tablets (haloperidol decanoate), Hibistat germicidal hand rinse (chlorhexidine gluconate), HISMANAL® tablets (astemizole), HydroDIURIL tablets (hydrochlorothiazide), Hydromox tablets (quinethazone), Hydropres tablets (reserpine and hydrochlorothiazide), Inderide® tablets (propranolol hydrochloride and hydrochlorothiazide), Inderides capsule® (propranolol hydrochloride and hydrochlorothiazide), Intal inhaler (cromolyn sodium), Intron A injection (recombinant interferon α-2b), Lamprene capsules (clofazimine), Lasix oral solution (furosemide), Lasix tablets (furosemide), Lasix injection (furosemide), Limbitrol tablets (chlordiazepoxide and amitriptyline hydrochloride), Lodine capsules (etodolac), Lopressor HCT tablets (metoprolol tartrate USP and hydrochlorothiazide USP), Lotensin tablets (benazepril hydrochloride), LOZOL® tablets (indapamide), Ludiomil tablets (maprotiline hydrochloride USP), Marplan tablets (isocarboxazid), MAXAQUIN® tablets (lomefloxacin HCl), Maxzide tablets (triamterene USP and hydrochlorothiazide USP), Mellaril® concentrate (thioridazine), Mellaril® tablets (thioridazine), Mellaril-S suspension (thioridazine), Mepergan injection (meperidine hydrochloride and promethazine hydrochloride), Methotrexate tablets (methotrexate), Mevacor tablets (lovastatin), Micronase tablets (glyburide), Minizide capsules (prazosin hydrochloride and polythiazide), Minocin intravenous ((4S-(4α,4aα,5aα,12aα))-4,7-bis(dimethylamino)-1,4,4a,5,5a,6,11,12a-octahydro-3,10,12,12a-tetrahydroxy-1,11-dioxo-2-naphthacenecarboxamide monohydrochloride), Minocin oral suspension ((4S-(4α, 4aα,5aα,12aα))-4,7-bis(dimethylamino)-1,4,4a,5,5a,6,11,12a-octahydro-3,10,12,12a-tetrahydroxy-1,11-dioxo-2-naphthacenecarboxamide monohydrochloride), Minocin capsules ((4S-(4α,4aα,5aα,12aα))-4,7-bis(dimethylamino)-1,4,4a,5,5a,6,11,12a-octahydro-3,10,12,12a-tetrahydroxy-1,11-dioxo-2-naphthacenecarboxamide monohydrochloride), Moduretic tablets (amiloride HCl-hydrochlorothiazide), Monodox® capsules (doxycycline monohydrate), Monopril tablets (fosinopril sodium), Children's Motrin liquid suspension (ibuprofen), Motrin tablets (ibuprofen), Mykrox tablets (metolazone), NAPROSYN® suspension (naproxen), NAPROSYN® tablets (naproxen), Navane capsules (thiothixene), Navane intramuscular (thiothixene), NegGram caplets (nalidixic acid), NegGram suspension (nalidixic acid), Neptazane tablets (methazolamide), Nipent injection (pentostatin), Normodyne tablets (labetalol HCl), NOROXIN tablets (norfloxacin), Norpramin tablets (desipramine hydrochloride USP), oretic tablets (hydrochlorothiazide), Oreticyl Forte tablets (hydrochlorothiazide and deserpidine), Orinase tablets (tolbutamide), Ornade capsules (phenylpropanolamine hydrochloride and chlorpheniramine maleate), Orudis capsules (ketoprofen), Oxsoralen lotion (methoxypsoralen), PBZ tablets (tripelennamine hydrochloride USP), PBZ-SR tablets (tripelennamine hydrochloride USP), pHisoHex topical emulsion (hexachlorophene), P & S PLUS® topical tar gel (crude coal tar), Pamelor® capsules (nortriptyline HCl), Pamelor® solution (nortriptyline HCl), Paxil tablets (paroxetine hydrochloride), Pediazole oral suspension (erythromycin ethylsuccinate, USP and sulfisoxazole acetyl, USP), Penetrex™ tablets (enoxacin), Pentasa capsules (mesalamine), Periactin syrup (cyproheptadine HCl), Periactin tablets (cyproheptadine HCl), Phenergan tablets (promethazine hydrochloride), Phenergan injection (promethazine hydrochloride), Phenergan suppositories (promethazine hydrochloride), Phenergan syrup (promethazine hydrochloride), Polytrim® ophthalmic solution (trimethoprim sulfate and polymyxin B sulfate), Pravachol (pravastatin sodium), Prinivil® tablets (lisinopril, MSD), Prinzide tablets (lisinopril-hydrochlorothiazide), Prolixin elixir (fluphenazine hydrochloride), Prolixin enanthate (fluphenazine hydrochloride), Prolixin injection (fluphenazine hydrochloride), Prolixin oral concentrate (fluphenazine hydrochloride), Prolixin tablets (fluphenazine hydrochloride), ProSom tablets (estazolam), Prozac® oral solution (fluoxetine hydrochloride), Prozac® oral Pulvules® (fluoxetine hydrochloride), Pyrazinamide tablets (pyrazinamide), QUINAGLUTE® tablets (quinidine gluconate), Quinidex tablets (quinidine sulfate), Relafen tablets (nabumetone), Ru-Tuss II capsules (chlorpheniramine maleate and phenylpropanolamine hydrochloride), Seldane tablets (terfenadine), Septra tablets (trimethoprim and sulfamethoxazole), Septra suspension (trimethoprim and sulfamethoxazole), Septra I.V. infusion (trimethoprim and sulfamethoxazole), Septra tablets (trimethoprim and sulfamethoxazole), Ser-Ap-Es tablets (reserpine USP, hydralazine hydrochloride USP and hydrochlorothiazide USP), Sinequan capsules (doxepin HCl), Solganal injection (aurothioglucose, USP), Stelazine concentrate (trifluoperazine hydrochloride), Stelazine injection (trifluoperazine hydrochloride), Stelazine tablets (trifluoperazine hydrochloride), Surmontil capsules (trimipramine maleate), SYMMETREL capsules and syrup (amantadine hydrochloride), Taractan concentrate (chlorprothixene), Taractan injectable (chlorprothixene), Taractan tablets (chlorprothixene), TAVIST® syrup (clemastine fumarate, USP), TAVIST® tablets (clemastine fumarate, USP), TAVIST®-1 12 hour relief medicine (clemastine fumarate, USP), TAVIST®-D 12 hour relief medicine (clemastine fumarate, USP), Tegretol Tablets (carbamazepine USP), Tegretol suspension (carbamazepine USP), Temaril tablets (trimeprazine tartrate), Temaril syrup (trimeprazine tartrate), Temaril capsules (trimeprazine tartrate), TENORETIC® tablets (atenolol and chlorthalidone), Terramycin intramuscular solution (oxytetracycline), Thiosulfil Forte tablets (sulfamethizole), Thorazine ampuls (chlorpromazine hydrochloride), Thorazine concentrate (chlorpromazine hydrochloride), Thorazine multi-dose vials (chlorpromazine hydrochloride), Thorazine capsules (chlorpromazine hydrochloride), Thorazine suppositories (chlorpromazine hydrochloride), Thorazine syrup (chlorpromazine hydrochloride), Thorazine tablets (chlorpromazine hydrochloride), Timolide tablets (timolol maleate-hydrochlorothiazide), Tofranil ampuls (imipramine hydrochloride USP), Tofranil tablets (imipramine hydrochloride USP), Tofranil capsules (imipramine hydrochloride USP), Tolinase tablets (tolazamide), Triaminic Expectorant DH (phenylpropanolamine hydrochloride and guaifenesin), Triaminic oral infant drops (phenylpropanolamine hydrochloride, pheniramine maleate and pyrilamine maleate), Triavil tablets (perphenazine-amitriptyline HCl), Trilafon concentrate (perphenazine USP), Trilafon injection (perphenazine USP), Trilafon tablets (perphenazine, USP), Trinalin tablets (azatadine maleate, USP, and pseudoephedrine sulfate, USP), Vaseretic tablets (enalapril maleate-hydrochlorothiazide), Vasosulf opthalmic solution (sulfacetamide sodium-phenylephrine hydrochloride), Vasotec I.V. (enalapril maleate), Vasotec tablets (enalapril maleate), Velban® vials (vinblastine sulfate, USP), Vibramycin capsules (doxycycline monohydrate), Vibramycin intravenous (doxycycline monohydrate), Vibramycin oral suspension (doxycycline monohydrate), Vibra-Tabs tablets (oxytetracycline), Vivactil tablets (protriptyline HCl), Voltaren tablets (diclofenac sodium), X-SEB T® shampoo (crude coal tar), Zaroxolyn tablets (metolazone), ZESTORETIC® oral (lisinopril and hydrochlorothiazide), ZESTRIL® tablets (lisinopril), ZITHROMAX™ capsules (azithromycin), Zocor tablets (simvastatin), ZOLOFT® tablets (sertraline hydrochloride) and others.

Most of the above-described medications are available for oral usage in 2 mg, 4 mg, 5 mg, 8 mg, 10 mg, 16 mg, 25 mg, 50 mg, 75 mg, 100 mg, 125 mg, 150 mg, 200 mg, 250 mg, 400 mg, 500 mg, 750 mg, 1000 mg, etc., tablets, capsules and/or caplets, or as oral suspensions and/or syrups (25 mg/ml, 100 mg/ml, 250 mg/ml, etc), and are, or may be, formulated for administration in a once-a-day dose formulation. The present invention includes, but is not limited to, these different oral dosages.

Medications which cause photosensitivity and/or phototoxicity reactions, and which are administered in more than one dose per day may be suitably reformulated to a once-a-day dose by methods known by those of skill in the art, and administered during the evening, or early morning, hours, in accordance with the present invention, so as to prevent or reduce the photosensitivity and/or phototoxicity reactions caused by these medications. For example, it may be possible to increase the treatment dose of a medication for a particular disease if the photosensitivity and/or phototoxicity reactions caused by the medication have been a limiting side-effect. A person of ordinary skill in the art would know how to reformulate a multiple-dose-a-day medication for administration in a once-a-day dose formulation.

The method of the present invention is preferred for use with antimicrobial agents, particularly with the quinolone antibiotics, and most particularly with the anti-infective agent lomefloxacin hydrochloride (MAXAQUIN®), particularly with the 200 mg or the 400 mg daily dosage, which is available from G. D. Searle & Co. (Skokie, Ill.). Comparable doses of lomefloxacin hydrochloride on a body weight basis have been calculated to be approximately 2.5–8.0 mg per kg of body weight.

MAXAQUIN® (lomefloxacin hydrochloride) is a synthetic, broad-spectrum antimicrobial agent against both Gram-positive and Gram-negative bacteria, comparable to other quinolones, for oral administration. Lomefloxacin HCl, a difluoroquinolone, is the monohydrochloride salt of (±)-1-ethyl-6,8-difluoro-1,4-dihydro-7-(3-methyl-1-piperazinyl)-4-oxo-3-quinolinecarboxylic acid. Its empirical formula is $C_{17}H_{19}F_2N_3O_3 \cdot HCl$, and its structural formula is:

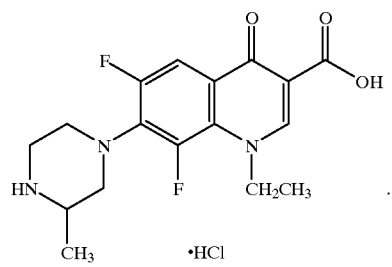

Lomefloxacin HCl is a white to pale yellow powder with a molecular weight of 387.8. It is slightly soluble in water, and practically insoluble in alcohol. Lomefloxacin HCl is stable to heat and moisture, but is sensitive to light in dilute aqueous solution.

Lomefloxacin hydrochloride is approved in the United States, and in several other countries throughout the world, for treatment of a variety of infections (uncomplicated and complicated urinary tract infections, acute exacerbation of chronic bronchitis, and as an agent to prevent infections occurring post-transurethral surgical procedures).

MAXAQUIN® is available as a film-coated tablet formulation containing 400 mg of lomefloxacin base, present as the hydrochloride salt. The base content of the hydrochloride salt is 90.6%. The inactive ingredients are carboxymethylcellulose calcium, hydroxypropyl cellulose, hydroxypropyl methylcellulose, lactose, magnesium stearate, polyethylene glycol, polyoxyl 40 stearate, and titanium dioxide.

MAXAQUIN® is supplied as a scored, film-coated tablet containing the equivalent of 400 mg of lomefloxacin base present as the hydrochloride. The tablet is oval, white, and film-coated with "MAXAQUIN 400" debossed on one side and scored on the other side.

Lomefloxacin HCl is a bactericidal agent with in vitro activity against a wide range of gram-negative and gram-positive organisms. The bactericidal action of lomefloxacin HCl results from interference with the activity of the bacterial enzyme DNA gyrase, which is needed for the transcription and replication of bacterial DNA. The minimum bactericidal concentration (MBC) generally does not exceed the minimum inhibitory concentration (MIC) by more than a factor of 2, except for staphylococci, which usually have MBC's 2 to 4 times the MIC.

Lomefloxacin HCl has been shown to be active against most strains of the following organisms both in vitro and in clinical infections:
Gram-positive aerobes
  *Staphylococcus saprophyticus*
Gram-negative aerobes
  *Citrobacter diversus*
  *Enterobacter cloacae*
  *Escherichia coli*
  *Haemophilus influenzae*
  *Klebsiella pneumoniae*
  *Moraxella* (Branhamella) *catarrhalis*
  *Proteus mirabilis*
  *Pseudomonas aeruginosa*.

Lomefloxacin HCl is minimally metabolized, although 5 metabolites have been identified in human urine. The glucuronide metabolite is found in the highest concentration, and accounts for approximately 9% of the administered dose. The other 4 metabolites together account for less than 0.5% of the dose. Approximately 10% of an oral dose was recovered as unchanged drug in the feces.

Serum protein binding of lomefloxacin HCl is approximately 10%.

The following are mean tissue or fluid to plasma ratios of lomefloxacin following oral administration.

| Tissue or Body Fluid | Mean Tissue or Fluid to Plasma Ratio |
|---|---|
| Bronchial mucosa | 2.1 |
| Bronchial secretions | 0.6 |
| Prostatic tissue | 2 |
| Sputum | 1.3 |
| Urine | 140.0 |
| Blister Fluid | 1.0 |

MAXAQUIN® film-coated tablets are indicated for the treatment of adults with mild to moderate infections caused by susceptible strains of the designated microorganisms in the conditions listed below:

LOWER RESPIRATORY TRACT

Acute Bacterial Exacerbation of Chronic Bronchitis caused by *Haemophilus influenzae* or *Moraxella* (Branhamella) *catarrhalis.*

URINARY TRACT

Uncomplicated Urinary Tract Infections (cystitis) caused by *Escherichia coli, Klebsiella pneumoniae, Proteus mirabilis* or *Staphylococcus saprohyticus.*

Complicated Urinary Tract Infections caused by *Escherichia coli, Klebsiella pneumoniae, Proteus mirabilis, Pseudomonas aeruginosa, Citrobacter diversus* or *Enterobacter cloacae.*

Photosensitivity and/or phototoxicity reactions have been reported in clinical trials of lomefloxacin HCl to varying degrees. Moderate to severe photosensitivity and/or phototoxic reactions have occurred in patients who were treated with lomefloxacin HCl, and who were exposed to direct or indirect sunlight, or to artificial ultraviolet light (e.g. sunlamps). These photosensitivity and/or phototoxicity reactions have also occurred in subjects exposed to shaded or diffuse light, including exposure through glass.

In clinical trials, most of the adverse events reported were mild to moderate in severity and transient in nature. During these clinical investigations, 2869 patients received MAXAQUIN®. In 2.6% of the patients, lomefloxacin was discontinued because of adverse events, primarily involving the gastrointestinal system (0.7%), skin (1.0%), or central nervous system (0.5%). The adverse clinical events with the highest incidence ($\geq 1\%$) in patients, regardless of relationship to drug, were nausea (3.7%), headache (3.2%), photosensitivity (2.4%), dizziness (2.3%), and diarrhea (1.4%).

Photosensitivity has been reported in 2.4% of patients treated with lomefloxacin hydrochloride and exposed to direct or indirect sunlight, or to artificial sunlight (e.g. sunlamps).

Lomefloxacin hydrochloride is recommended for a once-a-day administration. Due to its rapid absorption and distribution, if administered in the morning, it results in near peak serum and skin levels when daylight radiation is high. Therefore, if given in the early evening, lomefloxacin levels should be low by the next day when daytime radiation is high. If exposure begins at 2 hours after dosing, subjects would be receiving radiation during the time when both plasma and skin levels of lomefloxacin were near peak.

MAXAQUIN® may be prescribed by a physician to a patient as follows:

Patients with Normal Renal Functions: The recommended daily dose of MAXAQUIN® is described in the following chart:

| Body System | Infection | Unit Dose | Frequency | Duration | Daily Dose |
|---|---|---|---|---|---|
| Lower respiratory tract | Acute bacterial exacerbation of chronic bronchitis | 400 mg | q.d. | 10 days | 400 mg |
| Urinary tract | Cystitis | 400 mg | q.d. | 10 days | 400 mg |
| | Complicated Urinary Tract Infections | 400 mg | q.d. | 14 days | 400 mg |

Patients with Impaired Renal Function: Lomefloxacin HCl is primarily eliminated by renal excretion. Modification of dosage is recommended in patients with renal dysfunction. In patients with a creatinine clearance greater than 10, but less than 40 ml/min/1.73 m$^2$, the recommended dosage is an initial loading dose of 400 mg followed by daily maintenance doses of 200 mg (½ tablet) once daily for the duration of treatment. It is suggested that serial determinations of lomefloxacin levels be performed to determine any necessary alteration in the appropriate next dosing interval.

If only the serum creatinine is known, the following formula may be used to estimate creatinine clearance:

$$\text{Men: } \frac{(\text{weight in kg}) \times (140 - \text{age})}{(72) \times \text{serum creatinine (mg/dL)}}$$

Women: $(0.85) \times$ (calculated value for men).

Generally, one hundred per cent of orally-administered MAXAQUIN® is absorbed by the body and, thus, enters into the systemic circulation.

Several pharmacokinetic studies which have been performed in healthy volunteers have demonstrated that lomefloxacin is rapidly absorbed with peak serum concentrations achieved within 1–2 hours after dosing. The terminal elimination half-life of unchanged drug is approximately 8 hours over the entire range of single and multiple doses studied. Lomefloxacin concentrations reach steady-state by the end of the second day of dosing, an observation consistent with the eight hour terminal half-life. Sixteen (16) hours after dosing of MAXAQUIN®S, the plasma level of MAXAQUIN® is approximately one-fourth of the plasma level of MAXAQUIN® immediately after dosing.

A 400 mg oral dose of lomefloxacin hydrochloride produces drug concentrations in many body tissues and body fluids comparable to or higher than drug concentrations in systemic circulation. The low plasma protein binding of lomefloxacin contributes to this wide distribution.

Lomefloxacin HCl concentrations in the inflammatory exudate fluid of blisters formed with irritants peak 1.5 to 2.0 hours later than serum concentrations, but have the same terminal half-life. Equilibrium between the serum and blister fluid is achieved approximately two hours postdose, with a partition coefficient of 1.0 (blister fluid:serum). The concentration vs. time profiles in blister fluid following single dose administration are similar to those obtained at steady-state during a once daily dosing regimen. These results suggest that lomefloxacin hydrochloride quickly reaches moderately perfused tissues, such as the skin, and is distributed rapidly outside the vascular system. It is further suggested that lomefloxacin is eliminated from these tissues at approximately the same rate as from plasma.

For additional information concerning MAXAQUIN®, see U.S. Pat. No. 4,528,287 and the *Physicians Desk Reference*, supra., each of which is incorporated herein by reference.

Commercially-available antimicrobial agents which are contemplated for use in the methods of the present invention, either alone or in combination with one or more other drugs, include, but are not limited to, quinolone antibiotics (amifloxacin, cinoxacin, ciprofloxacin (Cipro®), difloxacin, enoxacin (Penetrex®), fleroxacin, flumequine, lomefloxacin, miloxacin, nalidixic acid, norfloxacin (Noroxin®), ofloxacin (Floxin®), oxolinic acid, pefloxacin, pipemidic acid, piromidic acid, rosoxacin, temafloxacin, tosufloxacin and others), sulfonamide antibiotics (derivatives of para-aminobenzene-sulfonamide, such as acetyl sulfamethoxypyrazine, acetyl sulfisoxazole, azosulfamide, benzylsulfamide, chloramine-B, chloramine-T, dichloramine T, formosulfathiazole, $N^2$-Formylsulfisomidine, $N^4$-β-D-glucosylsulfanilamide, mafenide, 4'-(methylsulfamoyl)sulfanilanilide, p-nitrosulfathiazole, noprylsulfamide, phthalylsulfacetamide, phthalylsulfathiazole, salazosulfadimide, succinylsulfathiazole sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, which is often employed in combination with trimethoprim in a drug known as co-trimoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicylic acid, $N^4$-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasolazine, sulfasomizole, sulfasymazine, sulfathiazole, sulfathiourea, sulfatolamide, sulfisomidine, sulfisoxazole and others), macrolide antibiotics (azithromycin, carbomycin, clarithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin and others), tetracycline antibiotics (apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin, tetracycline and others), amphenicol antibiotics (azidamfenicol, chloramphenicol, chloramphenicol palmitate, chloramphenicol pantothenate, florfenicol, thiamphenicol and others), aminoglycoside antibiotics (amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, streptonicozid, tobramycin and others), ansamycin antibiotics (rifamide, rifampin, rifamycin sv, rifaximin and others), cephalosporin antibiotics (cefaclor, cefadroxil, cefamandole, cefatrizine, cefazedone, cefazolin, cefixime, cefmenoxime, cefodizime, cefonicid, cefoperazone, ceforanide, cefotaxime, cefotiam, cefpimizole, cefpiramide, cefpodoxime proxetil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin C, cephalothin, cephapirin sodium, cephradine, pivcefalexin and others) cephamycin antibiotics (cefbuperazone, cefmetazole, cefminox, cefotetan, cefoxitin and others), monobactam antibiotics (aztreonam, carumonam, tigemonam and others), oxacephem antibiotics (flomoxef, moxolactam and others), penicillin antibiotics (amidinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, cafecillin sodium, carindacillin, clometocillin, cloxacillin, cyclacillin, dicloxacillin, diphenicillin sodium, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, talmapicillin, temocillin, ticarcillin and others), lincosamide antibiotics (clindamycin, lincomycin and others), polypeptide antibiotics (amphomycin, bacitracin, capreomycin, colistin, enduracidin, enviomycin, fusafungine, gramicidin(s), gramicidin S, mikamycin, polymyxin, polymyxin B-methanesulfonic acid, pristinamycin, ristocetin, teicoplanin, thiostrepton, tuberactinomycin, tyrocidine, tyrothricin, vancomycin, viomycin, viomycin pantothenate, virginiamycin, zinc bacitracin and others), 2,4-diaminopyrimidine antibiotics (brodimoprim, tetroxoprim, trimethoprim and others), nitrofuran antibiotics (furaltadone, furazolium chloride, nifuradene, nifuratel, nifurfoline, nifurpirinol, nifurprazine, nifurtoinol, nitrofurantoin and others), sulfone antibiotics (acedapsone, acediasulfone, acetosulfone sodium, dapsone, diathymosulfone, glucosulfone sodium, solasulfone, succisulfone, sulfanilic acid, p-sulfanilylbenzylamine, p,p'-sulfonyldianiline-N,N'digalac toside, sulfoxone sodium, thiazolsulfone and others), imipenem, clofazimine, cycloserine, mupirocin, tuberin, clofoctol, hexedine, methenamine, methenamine anhydromethylene citrate, methenamine hippurate, methenamine mandelate, methenamine sulfosalicylate, nitroxoline, xibornol, diathymosulfone, glucosulfone sodium, hydnocarpic acid, solasulfone, succisulfone, sulfoxone sodium, p-aminosalicylic acid, p-aminosalicylic acid hydrazide, benzoylpas, 5-bromosalicylhydroxamic acid, capreomycin, clofazimine, cyacetacide, cycloserine, dihydrostreptomycin, enviomycin, ethambutol, ethionamide, 4'-formylsuccinanilic acid thiosemicarbazone, furonazide, glyconiazide, isobutol, isoniazid, isoniazid methanesulfonate, morphazinamide, opiniazide, parsiniazide, phenyl aminosalicylate, protionamide, pyrazinamide, rifampin, salinazid, streptomycin, subathizone, sulfoniazide, thiacetazone, tiocarlide, tuberactinomycin, tubercidin, tuberin, verazide, viomycin, viomycin pantothenate and others. (See Goodman and Gilman's *The Basis of Therapeutics*, supra., and *The Merck Index*, supra.)

These commercially-available antimcrobial agents are generally available for oral usage in 2 mg, 4 mg, 5 mg, 8 mg, 10 mg, 16 mg, 25 mg, 50 mg, 75 mg, 100 mg, 125 mg, 150 mg, 200 mg, 250 mg, 400 mg, 500 mg, 750 mg, 1000 mg, etc., tablets, capsules and/or caplets, or as oral suspensions and/or syrups (25 mg/ml, 100 mg/ml, 250 mg/ml, etc), and are, or may be, formulated for administration in a once-a-day dose formulation. The present invention includes, but is not limited to, these different oral dosages.

Antimicrobial agents which are administered in more than one dose per day may be suitably reformulated to a once-a-day dose by methods known by those of skill in the art, and administered during the evening, or early morning, hours, in accordance with the present invention, so as to prevent or reduce the photosensitivity and/or phototoxicity reactions caused by these agents. For example, it may be possible to increase the treatment dose of an antimicrobial agent for a particular disease if the photosensitivity and/or phototoxicity reactions caused by the agent have been a limiting side-effect. A person of ordinary skill in the art would know how to reformulate a multiple-dose-a-day medication for administration in a once-a-day dose formulation.

Contemplated equivalents of the various medications described hereinabove which are contemplated for use in the methods of the present invention include compounds, drugs or medications which otherwise correspond thereto, and which have the same general properties thereof, wherein one or more simple variations of substituents are made which do not adversely affect the efficacy of the compound, drug or medication. The methods of the present invention contemplates the use of all such compounds, drugs and/or medications, including cis- and trans- geometric isomers, R- and S-enantiomers, diastereomers, d-isomers, l-isomers, the racemic mixtures thereof, and other mixtures thereof, as falling within the scope of the present invention.

The active ingredient(s) of certain medications contemplated for use in the methods of the present invention may contain a basic functional group, such as amino, alkylamino or dialkylamino, and may, thus, be capable of forming pharmaceutically-acceptable salts with pharmaceutically-acceptable acids. The term "pharmaceutically-acceptable salts" in this respect, refers to the relatively non-toxic, inorganic and organic acid addition salts of these active ingredients. Representative salts include the hydrobromide, hydrochloride, sulfate, bisulfate, phosphate, nitrate, acetate, valerate, oleate, palmitate, stearate, laureate, benzoate, lactate, phosphate, tosylate, citrate, maleate, fumarate, succinate, tartrate, naphthoate, mesylate, glucoheptonate, lactobionate, and laurylsulphonate salts and the like. (See, for example, S. M. Berge et al., "Pharmaceutical Salts," *J. Pharm. Sci.*, 66, 1–19 (1977), which, as well as all other documents referred to herein, is incorporated herein by reference.)

In other cases, the active ingredient(s) of medications contemplated for use in the methods of the present invention may contain one or more acidic functional groups, such as carboxyl and the like, and, thus, may be capable of forming pharmaceutically-acceptable salts of those active ingredients with pharmaceutically-acceptable bases. The term "pharmaceutically-acceptable salts" in these instances refers to the relatively non-toxic, inorganic and organic base addition salts of these active ingredients. Representative alkali or alkaline earth salts include the lithium, sodium, potassium, calcium, magnesium, and aluminum salts and the like. (See, for example, S. M. Berge et al., "Pharmaceutical Salts," supra.)

Although the methods of the present invention are preferred for use with once-a-day dose over-the-counter and/or prescription medications administered orally, in solid or liquid form, to humans (adults and/or children) and/or animals, these methods may be employed with once-a-day dose medications administered by any suitable route of administration, including parenteral administration, topical application (including buccally, rectally, pulmonary (inhalation) and sublingually), rectal or vaginal administration, nasal administration or intracisternal administration.

In accordance with the methods of the present invention, while it is preferred that the over-the-counter or prescription medication be administered in the evening just prior to dinner (between the hours of about 4:30 p.m. and about 9:30 p.m., preferably between the hours of about 5:30 p.m. and about 8:00 p.m., most preferably at about 6:00 p.m.), the medication may be administered anytime during the evening hours, between the hours of about 4:00 p.m. and about 4:00 a.m. This includes 4:00 p.m., 5:00 p.m., 6:00 p.m., 7:00 p.m., 8:00 p.m., 9:00 p.m., 10:00 p.m., 11:00 p.m., 12:00 p.m., 1:00 a.m., 2:00 a.m., 3:00 a.m., 4:00 a.m., and any variation of the minutes and/or seconds within any of these hours, such as 4:01 p.m., 4:02 p.m., 4:03 p.m., 4:04 p.m., 4:05 p.m., 4:06 p.m., 4:07 p.m., 4:08 p.m., 4:09 p.m., 4:10 p.m., etc.

A person of ordinary skill in the art will know how to choose the specific optimal evening dosing time, or range of times, for a particular over-the-counter or prescription medication, which will depend upon the half life of the photosensitivity and/or phototoxicity causing active ingredient(s) which is present in the medication.

A person of ordinary skill in the art will know how to administer a particular over-the-counter or prescription medication to a patient at a time sufficient for the blood level of such medication to be at a concentration which is less than a concentration which produces a photosensitivity and/or phototoxicity reaction during the daylight hours.

The unit dose and/or multiple dose packaging materials, labels and other mechanisms which may be employed in the article of manufacture of the present invention may be made of commercially-available paper, cardboard, foil, metal, plastic, glass, printable film, such as polyethylene terephthalate (PET) or polyvinyl chloride (PVC), and/or other suitable materials, with or without one or more layers of any type of an adhesive material (polyethylene, polyester, vinyl, acrylics, etc.). They may be of any convenient shape or size which is suitable for the particular medication being packaged. For example, see the commercially-available packaging and labeling for each of the medications described hereinabove which have been documented to be associated with photosensitivity and/or phototoxicity reactions, all of which are incorporated herein by reference.

The article of manufacture of the present invention may be labeled and/or arranged in a manner known by those of skill in the art which minimizes the risk that a once-a-day dose of a photosensitivity and/or phototoxicity causing medication will be taken by a patient at a time other than during the evening hours, or during the early morning hours. For example, the article of manufacture may have a label which conspicuously directs that a patient take a medication at a particular time during the evening or early morning hours. As another example, the article of manufacture may be a device which is arranged in a manner which only releases a medication at a particular time during the evening or early morning hours, or which only opens at a particular time during the evening or early morning hours.

(3) Utility

The methods and article of manufacture of the present invention have been found to result in the complete prevention or reduction of photosensitivity and/or phototoxicity reactions resulting from a once-a-day dose of an over-the-counter and/or prescription medication which causes such reactions, particularly orally-administered medications and, thus, are useful for preventing or reducing undesirable and, often painful, photosensitivity and/or phototoxicity reactions in human (adults and/or children) or animal (mammals and/or non-mammals) patients to which such medications are administered.

In addition, the lives of these patients, some of whom have employment which may require them to be outside or otherwise exposed to UVA radiation during many or all of the daylight hours (farmers, landscapers, gardeners, mailmen, construction workers, contractors, cab drivers, truck drivers, salesmen, policemen, sanitation engineers, boat tour guides, professional sports players, etc.), and some of whom have hobbies which normally take them outside during the daylight hours (gardening, swimming, boating, hiking, horseback riding, running, jogging, baseball, football, soccer, etc.), may become significantly less burdensome during the daylight hours. (For example, patients who take one or more of these medications may no longer have to avoid sunlight. Further, less protective sunscreen and clothing may be necessary during the daylight hours. However, any such changes in the behavior of these patients should be made under the guidance of a physician.)

(4) Dosage and Mode of Administration

The over-the-counter and/or prescription medications which may be employed in the methods of the present invention for medical and/or veterinarian use, many of which have been described hereinabove, optionally, may be combined with one or more other compounds, medications or materials. Because they are employed therapeutically, they would generally be used under the guidance of a physician. The appropriate dosage and form of administration of these medications will be suitably selected by methods which are consistent with conventional medical, pharmaceutical and veterinarian practices.

Actual dosage levels of the active ingredient(s) of the medications (over-the-counter or prescription) which may be employed in the methods of the present invention may be varied so as to obtain an amount of the active ingredient(s) which is effective to achieve the desired therapeutic response for a particular human (adult or child) or animal patient, and mode of administration, without being toxic to the patient.

The selected dosage level will depend upon a variety of factors including the activity of the particular active agent(s) employed, or the salt thereof, the route of administration, the time of administration, the rate of excretion of the particular active agent(s) being employed, the severity of the medical ailment, the duration of the treatment, other medications, compounds and/or materials used in combination with the particular active agent(s) employed, the age, sex, weight, condition, general health and prior medical history of the patient being treated, and like factors well known in the medical, pharmaceutical and veterinary arts.

A physician or veterinarian having ordinary skill in the art can readily determine and prescribe the effective amount of the medication required to alleviate or ameliorate a particular patient's ailment. For example, the physician or veterinarian could start doses of the medication at levels lower than that required in order to achieve the desired therapeutic effect and gradually increase the dosage until the desired effect is achieved.

In general, a suitable once-a-day dose of a medication will be that amount of the medication which is the lowest dose effective to produce a desired therapeutic effect. Such an effective dose will generally depend upon the factors described above.

MAXAQUIN® at a lower 200 mg a day dose may be given under the guidance of a physician during the evening hours, particularly before the evening meal, for infections such as uncomplicated urinary tract infections (UTIs). MAXAQUIN® at the higher dose of 400 mg a day dose may be given under the guidance of a physician during the evening hours, particularly before dinner, for complicated UTIs and other indications of severe intensity for which lomefloxacin hydrochloride is indicated. See the discussion presented hereinabove concerning the recommended dosing of MAXAQUIN®.

The total daily usage of a particular prescription and, sometimes, over-the-counter, medication will be determined by an attending physician or veterinarian within the scope of sound medical or veterinarian judgement.

The once-a-day dose medications (over-the-counter or prescription) which may be employed in the methods of the present invention include those suitable for oral, nasal, topical (including buccal and sublingual), rectal, vaginal and/or parenteral administration, with orally administered medications being preferred.

Once-a-day dose medications suitable for oral administration may be in the form of capsules, cachets, pills, tablets, lozenges, powders, granules, as a solution or a suspension in an aqueous or non-aqueous liquid, as an oil-in-water or water-in-oil liquid emulsion, as an elixir or syrup, as pastilles or as a bolus, electuary or paste and/or as mouth washes and the like.

Liquid dosage forms for oral administration of the medications which may be employed in the methods of the present invention include emulsions, microemulsions, solutions, suspensions, syrups and elixirs.

Formulations of the medications which may be employed in the methods of the present invention for rectal or vaginal administration may be presented as a suppository.

Formulations of the medications which may be employed in the methods of the present invention which are suitable for vaginal administration also include pessaries, tampons, creams, gels, pastes, foams or spray formulations.

Dosage forms for the topical or transdermal administration of medications which may be employed in the methods of the present invention include powders, sprays, ointments, pastes, creams, lotions, gels, solutions, patches and inhalants.

Ophthalmic formulations, eye ointments, powders, solutions and the like, are also contemplated as being within the scope of the methods of the present invention.

While the various aspects of the present invention are described herein with some particularity, those of skill in the art will recognize numerous modifications and variations which remain within the spirit of the invention. These modifications and variations are within the scope of the invention as described and claimed herein.

(5) EXAMPLES

The following examples describe and illustrate the methods of the present invention, as well as other aspects of the present invention, and the results achieved thereby, in further detail. Both an explanation of, and the actual procedures for, the various aspects of the present invention are described where appropriate. These examples are intended to be merely illustrative of the methods of the present invention, and not limiting thereof in either scope or spirit. Those of skill in the art will readily understand that known variations of the conditions and processes described in these examples can be used in the methods of the present invention.

Unless indicated otherwise herein, all of the starting materials, all of the over-the-counter and prescription medications and all of the equipment employed in the examples and/or otherwise discussed herein are commercially available. Sources for these materials, equipment and medications include Sigma Chemical Co. (St. Louis, Mo.), Aldrich Chemical Co. (Milwaukee, Wis.), Lancaster Synthesis (Windham, N.H.), Fisher Scientific (Pittsburgh, Pa.), Boehringer Mannheim Biochemicals (Indianapolis, Ind.), Fluka Chemical Corp. (Ronkonkoma, N.Y.), TCI, American Tokyo Kasei, Inc. (Atlanta, Ga.), Chemical Dynamics Corp. (South Plainfield, N.J.), G. D. Searle & Co. (Skokie, Ill.), Miles Inc., Pharmaceutical Division (West Haven, Conn.), Ortho Pharmaceuticals (Raritan, N.J.), Abbott Laboratories (Abbott Park, Ill.), Baxter Healthcare (Deerfield, Ill.), Merck & Co., Inc. (West Point, Pa.), Rhone-Poulenc Rorer Pharmaceutical (Collegeville, Pa.), Roche Laboratories (Nutley, N.J.), Roche Dermatologics (Nutley, N.J.), Wyeth-Ayerst Laboratories (Philadelphia, Pa.), Bristol Myers-Squibb Company (Princeton, N.J.), Ciba Pharmaceutical Company (Summitt, N.J.), Du Pont Pharmaceuticals (Wilmington, Del.), Johnson & Johnson Merck Consumer Pharmaceuticals Co. (Ft. Washington, Pa.), Glaxo Pharmaceuticals (Research Triangle Park, N.C.), Eli Lilly and Company (Indianapolis, Ind.), 3M Pharmaceuticals (St. Paul, Min.), Ortho-McNeil (Raritan, N.J.), Parke-Davis (Morris Plains, N.J.), Procter & Gamble (Cincinnati, Ohio), Ross Laboratories (Columbus, Ohio), U.S. Pharmaceutical (Decatur, Ga.), Lederle (Wayne, N.J.), Burroughs Wellcome Co. (Research Triangle Park, N.C.), The Purdue Frederick Company (Norwalk, Conn.), Hoechst-Roussel Pharmaceuticals, Inc. (Somerville, N.J.), Syntex Laboratories, Inc. (Palo Alto, Calif.), The Upjohn Company (Kalamazoo, Mich.), Kabi Pharmacia (Piscataway, N.J.), Marion Merrell Dow, Inc. (Kansas City, Mo.), Schering Corporation (Kenilworth, N.J.), Boehringer Mannheim Corporation (Indianapolis, Ind.), SmithKline Beecham Pharmaceuticals (Philadelphia, Pa.), Berlex Laboratories (Wayne, N.J.), Pfizer Labs Division (New York, N.Y.), A. H. Robins Company, Inc. (Richmond, Va.), Stuart Pharmaceuticals (Wilmington, Del.), Somerset Pharmaceuticals (Danville, N.J.), Sandoz Pharmaceuticals Corp. (East Hanover, N.J.), Sandoz Pharmaceuticals/Consumer Division (East Hanover, N.J.), Janssen Pharmaceutica, Inc. (Piscataway, N.J.), Schering Corporation (Kenilworth, N.J.), Fujisawa Pharmaceutical Company (Deerfield, Ill.), McNeil Pharmaceuticals, Inc. (Largo, Fla.), Stuart Pharmaceuticals (Wilmington, Del.), Fisons Consumer Health (Rochester, N.Y.), Fisons Corporation (Rochester, N.Y.), Dista (Madrid, Spain), Geigy Pharmaceuticals (Oxdoley, N.Y.), Key Pharmaceuticals, Inc. (Kenilworth, N.J.), Baker Cummins Pharmaceuticals, Inc. (Miami, Fla.), Roerig Division of Pfizer Incorporated (New York, N.Y.), Jacobus Pharmaceuticals Co., Inc. (Princeton, N.J.), Basel Pharmaceuticals Division of Ciba-Geigy Corp. (Summit, N.J.), Bristol Laboratories (Evansville, Ind.), Allergan Herbert (Irvine, Calif.), Athena Neurosciences, Inc. (South San Francisco, Calif.), IOLAB Corp. (Claremont, Calif.), James River Corp., (Milford, N.J.), Reynolds Metals Company (Richmond, Va.), Dupont (Wilmington, Del.), Morton Chemicals (Chicago, Ill.), Klockner-Pentaplast of America, Inc. (Gordonsville, Va.), Uhlmann Packaging Systems, Inc. (Fairfield, N.J.), Aylward Enterprises, Inc. (New Bern, N.C.), Storz Ophthalmics (St. Louis, Mo.), ICN Pharmaceuticals (Costa Mesa, Calif.) and Service Industries Midwest, Inc. (Rolling Meadows, Ill.).

All patents and publications referred to in the examples, and throughout this specification, are hereby incorporated herein by reference, without admission that such is prior art.

Example 1

General Pharmacokinetics of MAXAOUIN® in Volunteers

In 6 fasting healthy male volunteers, approximately 95% to 98% of a single oral dose of lomefloxacin HCl was absorbed. Absorption was rapid following single doses of 200 and 400 mg ($T_{max}$ 0.8 to 1.4 hours). Mean plasma concentration increased proportionally between 100 and 400 mg as shown below.

| Dose (mg) | Mean Plasma Concentration (µg/ml) | Area under Curve (AUC) (µg·h/ml) |
|---|---|---|
| 100 | 0.8 | 5.6 |
| 200 | 1.4 | 10.9 |
| 400 | 3.2 | 26.1 |

In 6 healthy male volunteers administered 400 mg of lomefloxacin HCl on an empty stomach q.d. for 7 days, the following mean pharmacokinetic parameter values were obtained:

| | |
|---|---|
| $C_{max}$ | 2.8 µg/ml |
| $C_{min}$ | 0.27 µg/ml |
| $AUC_{0-24\,h}$ | 25.9 µg·h/ml |
| $T_{max}$ | 1.5 h |
| $t_{½}$ | 7.75 h |

The elimination half-life in 8 subjects with normal renal function was approximately 8 hours. At 24 hours post dose, subjects with normal renal function receiving single doses of 200 or 400 mg lomefloxacin HCl had mean plasma lomefloxacin HCl concentrations of Q.10 and 0.24 µg/ml, respectively. Steady-state concentrations were achieved within 48 hours of initiating therapy with once-a-day dosing. There was no drug accumulation with single daily dosing in patients with normal renal function.

Approximately 65% of an orally administered dose of lomefloxacin HCl was excreted in the urine as unchanged drug in patients with normal renal function. Following a 400 mg dose of lomefloxacin HCl administered q.d. for 7 days, the mean urine concentration was in excess of 300 µg/ml 4 hours post dose. The mean urine concentration exceeded 35 µg/ml for at least 24 hours after dosing.

Following a single 400 mg dose of lomefloxacin HCl, the solubility of lomefloxacin HCl in urine usually exceeded its peak urinary concentration 2 to 6 fold. In this study, urine pH affected the solubility of lomefloxacin with solubilities ranging from 7.8 mg/ml at pH 5.2, to 2.4 mg/ml at pH 6.5, and 3.03 mg/ml at pH 8.12.

The urinary excretion of lomefloxacin HCl was virtually complete within 72 hours after cessation of dosing, with approximately 65% of the dose being recovered as parent drug and 9% as its glucuronide metabolite. The mean renal clearance was 145 ml/min in subjects with normal renal function (GFR=120 ml/min).

Food effect: When lomefloxacin and food were administered concomitantly, the rate of drug absorption was delayed

[$T_{max}$ increased to 2 hours (delayed by 41%), $C_{max}$ decreased by 18%], and the extent of absorption (AUC) was decreased by 12%.

Pharmacokinetics in the Geriatric Population: In 16 healthy elderly volunteers (61 to 76 years of age) with normal renal function for their age, the half-life of lomefloxacin HCl (mean of 8 hours) and peak plasma concentration (mean of 4.2 μg/ml) following a single 400 mg dose were similar to those in 8 younger subjects dosed with a single 400 mg dose. Thus, drug absorption appeared to be unaffected in the elderly. Plasma clearance was, however, reduced in this elderly population by approximately 25%, and the AUC was increased by approximately 33%. This slower elimination most likely reflects the decreased renal function normally observed in the geriatric population.

Pharmacokinetics in the Renally Impaired Patients: In 8 patients with creatinine clearance ($Cl_{Cr}$) between 10 and 40 ml/min/1.73 m², the mean AUC after a single 400 mg dose of lomefloxacin HCl increased 335% over the AUC demonstrated in patients with a $Cl_{Cr}$>80 ml/min/1.73 m². Also, in these patients, the mean $t_{1/2}$ increased to 21 hours. In 8 patients with $Cl_{Cr}$<10 ml/min/1.73 m², the mean AUC after a single 400 mg dose of lomefloxacin HCl increased 700% over the AUC demonstrated in patients with a $Cl_{Cr}$>80 ml/min/1.73 m². In these patients with $Cl_{Cr}$<10 ml/min/1.73 m², the mean $t_{1/2}$ increased to 45 hours. The plasma clearance of lomefloxacin was closely correlated with creatinine clearance, ranging from 31 ml/min/1.73 m² when creatinine clearance was zero to 271 ml/min/1.73 m² at a normal creatinine clearance of 110 ml/min/1.73 m². Peak lomefloxacin concentrations were not affected by the degree of renal function when single doses of lomefloxacin were administered.

Pharmacokinetics in Patients with Cirrhosis: In 12 patients with histologically confirmed cirrhosis, no significant changes in rate or extent of lomefloxacin HCl exposure ($C_{max}$, $T_{max}$, $t_{1/2}$ or AUC) were observed when they were administered 400 mg of lomefloxacin HCl as a single dose.

Example 2

Photosensitivity Reactions in Healthy Volunteers after Administration of Lomefloxacin HCl, Ciprofloxacin and Doxycycline A clinical study concerning the issue of photosensitivity and/or phototoxicity reactions caused by lomefloxacin HCl, ciprofloxacin and/or doxycycline was conducted in normal male volunteers (N-31), exposing them to UVA and UVA/UVB radiation subsequent to administration of oral doses of lomefloxacin HCl, 400 mg twice per day (BID), ciprofloxacin 750 mg twice per day (BID) and doxycycline 100 mg twice per day (BID) for 14 days.

This study was a single center, open label, multiple does, parallel, randomized study in healthy male volunteers. There were 16 patients in the lomefloxacin HCl arm, and there were 15 patients each in the ciprofloxacin and the doxycycline arms.

Drug administration began on day three. Single dermatological sites were chosen on each of the subjects to be the site which was to be evaluated over time. Twenty joules of radiation were administered to these sites in day 1, day 6 and day 16. Also, graded UVA-UVB exposure was performed on days 2, 7 and 16. The dermatological responses were scored at 1, 24 and 48 hours after each UVA exposure and at 24 hours after the combined UVA-UVB exposure.

The definitions which were employed in interpreting this study were that photosensitivity was to be assessed by exposure duration associated with the smallest dermatological response score above zero, which was defined as the minimal erythrogenic dose after the UVA-UVB exposure. The photosensitivity and/or phototoxicity reaction was taken by definition to be an increase of equal to or greater than 1 unit in what was defined as a dermatological response over baseline values after the UVA exposure.

The results of this study revealed significant rates of photosensitivity reactions for the two quinolone antibiotics, lomefloxacin (64%) and ciprofloxacin (13%).

Example 3

Multicenter Comparative Safety and Efficacy Study of Lomefloxacin HCl

A double blind, randomized, parallel group, three-arm clinical study concerning the photosensitivity reactions caused by lomefloxacin HCl was the multicenter comparative safety and efficacy study which was conducted in Sweden. 400 mg of lomefloxacin HCl was given once a day (q.d.) for either three days or seven days. 703 patients were enrolled in this study, before newly-raised awareness of photosensitivity reactions associated with lomefloxacin HCl.

The safety section of the protocol and the Informed Consent Form employed in this study did not reflect any special instructions or warnings to the patients. However, about one year into the study, on Feb. 2, 1989, a letter was sent out to each of the study investigators regarding the possible risks of lomefloxacin HCl photosensitivity reactions. This information was again communicated to the study investigators at an Investigator's Meeting which was held on Jun. 8, 1989. The above-described warnings to study investigators apparently may have not been shared with the patients taking part in the study because photosensitivity rates for this study were reported as 4% for lomefloxacin HCl 400 mg×3 days, and as 10% for lomefloxacin HCl 400 mg×7 days.

Example 4

Photosensitivity Reactions in Healthy Volunteers After Administration of Lomefloxacin HCl or Trimethoprim in the Evenings A clinical trial concerning photosensitivity reactions caused by lomefloxacin HCl, and resulting in the total elimination of photosensitivity reactions in volunteers to which lomefloxacin HCl was administered in the evening hours, was conducted in the United Kingdom. Patients with uncomplicated urinary tract infection were randomized to receive lomefloxacin HCl 200 mg taken at night for 3 nights and trimethoprim in a double-blind study.

The clinical success in the lomefloxacin HCl group in evaluable patients 7–9 days posttreatment was 98.1%, with overall incidence of adverse events at 18%, and no photosensitivity reactions reported. This study appears to have a high degree of efficacy, with no reports of photosensitivity reactions, even with no special instruction to patients in the Informed Consent Form or the Patient Instructions.

Example 5

Clinical Comparison of the Phototoxicity Potential of Oral Lomefloxacin Hydrochloride in Normal Healthy Volunteers using Morning or Evening Dosing Introduction In this clinical study, the photosensitivity and/or phototoxicity reactions to MAXAQUIN® occurring 2 and 16 hours after dosing was analyzed during the period between Sep. 30, 1993, and Oct. 25, 1993, to determine whether photosensitivity to UVA and/or UVB radiation correlated with time after dosing and plasma levels of drug. It was hypothesized that, if this were true, the safety of MAX- AQUIN® use by patients might be improved by recommending evening, rather than morning or afternoon, administration of MAXAQUIN® to patients as a way to prevent or reduce the risk of photosensitivity and/or phototoxicity reactions. With evening dosing, the highest levels of drug in the blood and in the skin would occur during the night, and the lowest levels of drug in the blood and in the skin would occur during the period of peak sunlight the next day.

This study describes a randomized, single site, double-blind, two treatment, two period, two sequence, cross-over clinical pharmacology study which was performed according to FDA regulations in 27 healthy normal volunteers with fair skin that could easily burn when exposed to sunlight, to assess the photosensitivity and/or phototoxicity potential of oral 400 mg lomefloxacin hydrochloride (MAXAQUIN®) administered once daily for 4 consecutive days either in the morning (morning dose group), as described hereinbelow, or in the early evening (evening dose group), as described hereinbelow. Irradiation and evaluation of irradiated sites began at 2 hours after the final morning dose of lomefloxacin HCl for the morning dosing group, and began 16 hours after the final evening dose of lomefloxacin HCl for the evening dosing group.

The primary objective of the study was to assess whether longer intervals (16 hours versus 2 hours) between lomefloxacin HCl dosing and exposure to UVA radiation, i.e., evening versus morning dosing, would reduce the risk of photosensitivity reactions in subjects exposed to UVA radiation generated by a solar simulator. This determination was based on a comparison of the difference between baseline Minimal Erythema Dose (MED, $J/cm^2$) and posttreatment delayed MED for the a.m. and p.m. dosing.

This study was designed to assess whether dosing of lomefloxacin hydrochloride in the early evening (16 hours before exposure to radiation), rather than in the morning (2 hours before exposure to radiation), would significantly reduce skin photosensitivity and/or phototoxicity response resulting from the administration of lomefloxacin HCl in subjects exposed to artificial sources of UVA and/or UVB radiation (a solar simulator with appropriate filters) the following day. This investigation measured the morning vs. evening difference in response to different energy levels of UVA and/or UVB radiation induced by this solar simulator. The primary variable for analysis was delayed MED.

The primary focus of this study was to compare the Minimum Erythema Dose (MED) (the smallest dose of irradiation (UVA and/or UVB) causing erythema of a predetermined area of skin, such as a 1 $cm^2$ patch of skin) for the two dosing groups of MAXAQUIN® (p.m. vs a.m.) for UVA and/or UVB data.

"Baseline MED" was defined as the lowest dose of UVA radiation alone, or UVA and UVB radiation, that produced a minimal perceptible erythema filling a 1 $cm^2$ patch of skin 24 hours post radiation.

"Delayed MED" was defined as the lowest dose of UVA radiation alone, or UVA and UVB radiation, that produced a minimal perceptible erythema filling a 1 $cm^2$ patch of skin, when testing the area 24, 48 and 72 hours post radiation.

"Immediate MED" was defined as the lowest dose producing minimal perceptible erythema filling a 1 $cm^2$ patch of skin when testing the area 0, 3, and 6 hours post radiation.

"$MED_{UVA}$" was defined as the MED produced by a UVA light source.

"$MED_{UVA+UVB}$" was defined as the MED produced by a full spectrum UVA plus UVB light source.

In order to determine the levels of lomefloxacin HCl immediately before exposure to radiation, and during the 72 hours after such exposure, blood was sampled at predesignated times during the study, as described hereinbelow in detail.

The logistics of the study required that the clock time of dosing of MAXAQUIN® and, therefore, UVA and/or UVB exposure may vary among subjects. The relative timing was, however, kept constant, so that the p.m. doses followed the a.m. doses by 10 hours, and light tests were performed 2 hours after the final a.m. doses. As described in more detail hereinbelow, the scoring of all skin sites exposed to a controlled ultraviolet light source was performed using the same scoring criteria throughout the study.

Baseline measurements of MED to full spectrum exposure to UVA and UVB radiation, and to UVA radiation alone, were taken during the screening period discussed hereinbelow. At the completion of the screening process, subjects with established MED who had satisfactorily met all the inclusion criteria (see discussion hereinbelow), and who had none of the exclusion criteria (see discussion hereinbelow), were randomized to participate in the study.

This study was divided into two treatment periods separated by a five-day washout period.

Each subject received a single daily dose (either p.m. or a.m.) of active 400 mg lomefloxacin hydrochloride over a five-day period, complemented with a matching capsule of inert ingredients as an alternative treatment (oral administration of 400 mg lomefloxacin in the morning and a matching inert capsule in the evening, or an inert capsule in the morning and a matching dose of 400 mg lomefloxacin in the evening, for a total of eight doses over a five-day period).

After all baseline procedures, including determination of baseline $MED_{UVA}$ and $MED_{UVA+UVB}$ values 24 hours post-radiation, were completed, all subjects started Study Day 1 of Treatment Period 1 with an evening dose of study medication, and completed this phase of the treatment regime with a morning dose of study medication on Study Day 5. Two hours after the final morning dose, and 16 hours after the last evening dose, a randomly selected site composed of six patches of skin, each with an area of one square centimeter, on the back or buttock of the subject was irradiated with incremental amounts of energy. Immediately following irradiation (0 hour), and at 3, 6, 24, 48 and 72 hours following irradiation, each skin patch area was evaluated to determine the MEDs, and assess the severity of skin reaction using a five-grade system, as described hereinbelow. The lowest of the MEDs determined at 0, 3 and 6 hours post-radiation were referred to as immediate MEDs, and the lowest of the MEDs determined at 24, 48 and 72 hours post-radiation were referred to as delayed MEDs.

A washout period lasting 5 days followed Treatment Period 1, and was concluded by determining MED levels. On the fifth washout day, subjects were irradiated for determination of Treatment Period 2 baseline MEDs. Irradiated sites were evaluated for Treatment Period 2 baseline MEDs, and graded for severity at 24 hours post-radiation.

After the above-described irradiation, in Treatment Period 2, each subject was crossed over to receive the alternate treatment regimen for a total of eight doses over a five-day period (5 days of alternative a.m. or p.m. treatment). Using the same design as for Treatment Period 1, subjects began with an evening dose of study medication on Study Day 11, and completed the treatment regimen with a morning dose of study medication on Study Day 15. Randomly chosen skin sites were irradiated and assessed using the same procedures and timepoints as described for Treatment Period 1.

In order to determine the correlation between MED measurements and plasma levels of lomefloxacin HCl, a number of plasma samples were drawn during both treatment periods, as described in more detail hereinbelow.

Safety was assessed based on data from physical examinations, clinical laboratory evaluations, and reported adverse events.

Determination of photosensitivity was based on a comparison of the difference between baseline Minimal Erythema Dose (MED, $J/cm^2$) and post-treatment delayed MED for the a.m. and p.m. dosing groups. Severity of response was assessed by comparing the number of subjects who developed responses of edema and/or blisters on the radiated skin sites. The correlation between lomefloxacin HCl plasma levels at time of irradiation and delayed $MED_{UVA}$ was also assessed.

Time

Some of the times presented hereinbelow are in military time, which employs a 24-hour clock (0100 hours to 2400 hours). The following chart may be employed to convert military time to non-military time:

| TIME | |
|---|---|
| Military Time | Non-Military Time |
| 0100 | 1:00 a.m. |
| 0200 | 2:00 a.m. |
| 0300 | 3:00 a.m. |
| 0400 | 4:00 a.m. |
| 0500 | 5:00 a.m. |
| 0600 | 6:00 a.m. |
| 0700 | 7:00 a.m. |
| 0800 | 8:00 a.m. |
| 0900 | 9:00 a.m. |
| 1000 | 10:00 a.m. |
| 1100 | 11:00 a.m. |
| 1200 | 12:00 NOON |
| 1300 | 1:00 p.m. |
| 1400 | 2:00 p.m. |
| 1500 | 3:00 p.m. |
| 1600 | 4:00 p.m. |
| 1700 | 5:00 p.m. |
| 1800 | 6:00 p.m. |
| 1900 | 7:00 p.m. |
| 2000 | 8:00 p.m. |
| 2100 | 9:00 p.m. |
| 2200 | 10:00 p.m. |
| 2300 | 11:00 p.m. |
| 2400 | 12:00 a.m. |

Criteria for Inclusion

The criteria employed for including volunteers in this study were as follows:
1. Subjects had to be healthy Caucasian males or females, 18–55 years of age.
2. Females had to be nonpregnant and nonlactating. All females, including those of non-childbearing potential, were required to take a serum pregnancy test with negative results, prior to randomization. Females of childbearing potential had to use a contraception method acceptable to the investigator.
3. Subjects had to weigh at least 40 kg, and less than 100 kg.
4. Subjects had to have skin type I or II (Fitzpatrick Classification, which is described in T. Fitzpatrick, "The Validity and Practicality of Sunreactive Skin Types I thought IV," 124: 869–871 Arch. Dermatol (1988)).
5. Subjects had to be able and willing to undergo medical history, physical and laboratory examinations prior to and at the end of the study.
6. Subjects had to be able to be domiciled in a controlled environment for 16 days from 0700 hours to 1900 hours (earlier than 0700 hours or later than 1900 hours if procedures required).
7. Subjects had to be able to abstain from consumption or usage of all alcoholic beverages, perfumes, body lotions and creams 48 hours before, during, and 24 hours following completion of this study.
8. Documented written informed consent had to be obtained prior to admission to this study.
9. Negative hepatitis B surface antigen test results had to be obtained within the last 7 days prior to admission to this study.

Criteria for Exclusion

The following criteria were employed to exclude individuals from this study:
1. Subjects with a history of sun hypersensitivity or photosensitive dermatoses.
2. Subjects with a history of allergic reaction or hypersensitivity to quinolone or tetracycline antibiotics.
3. Scars, moles, blemishes or excessive hair on the back or any condition which may interfere with the scoring or erythema responses.
4. Recent sunburn or prolonged sun exposure within the six weeks prior to this study.
5. Insufficient untanned skin areas (back, buttocks) for all phototesting.
6. MED/UVA greater than 30 $J/cm^2$ at baseline with the radiation sources described hereinbelow.
7. Concurrent medications of any kind, including over-the-counter preparations, or any antibiotic/antimicrobial treatment within two weeks prior to the study.
8. A subject with a significant history, clinical or laboratory evidence of renal, hepatic, cardiovascular, gastrointestinal or hematological disease, alcohol or drug abuse.
9. Subjects with history of convulsive disorders.
10. Any subject who had received any investigational medication within 30 days prior to the first dose of study medication, or who was scheduled to receive an investigational drug other than lomefloxacin HCl during the course of this study.
11. Subjects previously admitted to the study.

Patient Disposition

A sufficient number of subjects was to be enrolled in the study to ensure that a total of at least 24 evaluable subjects (12 per treatment sequence) completed the study. Subjects discontinuing participation in the study were to be replaced to ensure completion of the study by at least 24 subjects. It was determined prior to study initiation that this sample size should be sufficient to detect a mean difference between the two treatments of the change between baseline versus post-treatment $MED_{UVA}$ of 5 $J/cm^2$ of UVA radiation with at least 90% power at the two-sided 5% significance level.

Subjects were eligible to enroll in this study if they met all of the inclusion criteria described above, but met none of the exclusion criteria described above.

A total of 28 patients were enrolled at a single United States center. 14 subjects were randomized into each treatment sequence group. Only 27 subjects were evaluable for efficacy analyses.

The phototoxicity analysis described hereinbelow was performed on the 27 subjects who completed the study.

Demographics

The subjects were from 18 to 55 years of age, with a median age of 34. All subjects were healthy and Caucasian, with 71% males and 29% females (nonpregnant, nonlactating and using oral contraception if of childbearing potential). Patient heights and weights were similar for the two treatment sequence groups.

Treatment sequence group comparability with regard to demographic characteristics at baseline was assessed. Continuous variables were analyzed using the Kruskal-Wallis test (age, height and weight), which is known by those of skill in the art. Categorical data were analyzed using the Pearson chi-square test, which is known by those of skill in the art, for marginal homogeneity. Age data were also grouped into quintiles for analysis of the distribution between treatment sequence groups using the Pearson chi-square test.

Reasons for Study Termination

One subject withdrew from the study due to procedural non-compliance. No statistically significant difference was found between the number of withdrawals between the treatment sequence groups (p=0.309).

Randomization Procedures

Twenty seven (27) subjects complying with the above-described inclusion criteria, and having none of the above-described exclusion criteria, were enrolled in the study, and were randomly assigned to receive either a morning dose of 400 mg of lomefloxacin hydrochloride in an encapsulated tablet (morning lomefloxacin HCl dose group), or of a matching inert capsule consisting of Avicel Ph101, hydroxypropyl cellulose, Avicel Ph102, explotab and magnesium stearate (evening lomefloxacin HCl dose group), each of which was supplied by G. D. Searle & Co. (Skokie, Ill.), and the opposite in the evening. The medication a subject was randomized to receive was determined from a computer generated randomization code prepared at G. D. Searle & Co. prior to the start of the study. A subject who met the entrance criteria was to be sequentially assigned the next available subject number, and was to receive the treatment regimen assigned to that number.

After Treatment Period I (5 days), and then after a 5-day wash out period, subjects were crossed over to the other regimen. (Volunteers which had previously been in the morning lomefloxacin HCl dose group were now placed into the evening lomefloxacin HCl group, and vice versa.)

All subjects began Study Day 1 with an evening dose of lomefloxacin HCl, or matching inert capsule, and completed this treatment period with the morning dose of alternative treatment. All subjects received 4 single daily doses of encapsulated 400 mg lomefloxacin hydrochloride tablets either in the morning, or in the evening, as described in more detail hereinbelow.

Labeling of Clinical Supplies

Two-part labels were computer-generated for this blinded study. One part of the label, containing study and subject information, was attached to the container, and the other part was a tear-off portion that contained the same information, plus a sealed pouch containing the identity of the assigned treatment. This tear-off tab was removed at the time of dispensing, attached to the subject's appropriate Case Report Form (CRF) and retained in the Investigator's study file.

Code Breaks

The identity of the treatment(s) to which a subject was assigned was concealed in a tear-off part of the label in a sealed pouch.

Schedule of Observations and Procedures

The eligibility of patients for enrollment in this study was determined with the 7-day pre-study screening period described hereinbelow immediately preceding randomization of subjects into the study. Randomization was followed by a 5-day treatment period, followed by radiation 2 hours after the last morning dose of study medication and 72 hours of evaluation of test sites. At the end of a 5-day wash out period and MED determination, the subjects were crossed-over to 5 days of the alternative treatment. The last morning dose of study medication was followed in 2 hours by irradiation and in 72 hours by evaluation of radiated sites.

Pretreatment Screening Period

Medical History and Physical Examination

All subjects underwent a physical examination, including vital signs and a 12-lead EKG, and furnished a medical history within 7 days prior to receiving the first dose of study medication.

Clinical Laboratory Tests

Within seven days prior to receiving the first dose of study medication, subjects were evaluated for study eligibility by performing the laboratory tests listed below. These tests were performed as close as possible before administration of baseline radiation.

| a. | Hematology | |
|---|---|---|
| | WBC w/differential | |
| | RBC count | |
| | HGB | |
| | HCT | |
| | Platelet count | |
| b. | Biochemistries | |
| | Potassium | Urea Nitrogen |
| | Chloride | Total Bilirubin |
| | Calcium | Alkaline Phosphatase |
| | BUN | SGOT/AST |
| | Creatinine | SGPT/ALT |
| | Glucose | Uric Acid |
| | Sodium | |
| c. | Urinalysis | |
| | Protein | |
| | Glucose | |
| | Blood | | d. Serum pregnancy test for all females within 48 hours of study entry, and on Study Day 18 as part of end of study procedures.

e. Urine Drug and Alcohol Screen.

f. Hepatitis B.

g. Plasma sample for pK analysis was collected at pre-designated times, as described in more detail hereinbelow. (All plasma samples were sent to Pharmaco-LSR (Richmond, Va.) for analysis).

All clinical laboratory determinations were performed at the SciCor laboratories (Indianapolis, Ind.).

Phototoxicity—Sites, Radiation Source and Grading

Sites: The back and buttocks of each subject were examined and 8 sites, each of which could accommodate 6 one centimeter square ($cm^2$) patches, were chosen randomly for irradiation and post-irradiation evaluation. The sites chosen were between the shoulder and the waist adjacent to the spinal midline, or on the buttocks, and were free of any physical interference or suntan. The 8 sites were numbered (top right of person to bottom left). The assignment of each of the 8 body sites to time of testing (i.e. pretreatment 1, posttreatment 1, pretreatment 2, posttreatment 2) was done through randomization at the study site. No skin site was irradiated more than once during the entire study, including the screening.

Radiation source: The source of radiation employed was an Oriel (Santa Monica, Calif.) Xenon Arc 1000 watt solar simulator, with the following filters: WG320 filter (1 mm thick, emitting full spectrum UVA and UVB radiation), WG335 filter (3 mm thick, emitting almost exclusively UVA radiation) or UG11 filter (to filter infrared radiation).

Prior to initiation of the study, the solar simulator designated to be used in this study was checked and calibrated in accordance with regulations to determine suitability of UV solar simulators for testing sunscreen drug products for over-the-counter human use. The calibration and quality assurance assessment were performed by Rapid Precision Testing Laboratories (Cordova, Tenn.) in September 1993. The measurements of the entire spectrophotometric system varied by less than 1% during the course of the calibration. The UVA emission for the solar simulator with 3 mm WG335 and UG11 filters produced the $MED_{UVA}$ with a mean exposure of 13.9 minutes. The power spectrum contained only 0.148% UVB radiation.

The pretreatment, i.e. baseline, Minimal Erythema Dose (MED) was determined up to seven days prior to beginning study medication using increasing doses of radiation. The MED was measured separately for UVA wavelengths and UVA+UVB wavelengths.

For predrug exposure MED determination, 2 sets each with six 1 $cm^2$ patches on the back or buttocks were irradiated with increasing doses of UVA and UVB radiation, and UVA radiation alone, up to 7 days prior to beginning of drug treatment. With respect to UVA light source, irradiation began at 5 $J/cm^2$, and was increased by increments of 5 $J/cm^2$ using a different skin patch for each exposure. The maximum radiation dose was 30 $J/cm^2$. Subjects with MED greater than 30 $J/cm^2$ were excluded from the study. Full spectrum UVA and UVB light source irradiation began at 0.060 $J/cm^2$, and incrementally increased to the maximum of 0.148 $J/cm^2$. A different skin patch was used for each exposure.

Grading: The response of the skin to UVA and/or UVB radiation was observed to determine the Minimal Erythematous Dose (MED) of UVA and/or UVB radiation. The number of skin patches with edema, or local swelling of the skin surface, were also counted. MEDs were measured separately for UVA and UVB radiation, and for UVA radiation alone. The baseline MED was defined in the manner described hereinabove. The 24 hour evaluation was allowed to be performed in the morning of Study Day 1. Severity of reactions causing edema and/or blisters were graded under the following grading system:

| Grade | Radiation Site Condition |
| --- | --- |
| 0 | No reaction |
| 0.5 | Minimal perceptible erythema |
| 1 | Definite erythema |
| 2 | Erythema with edema |
| 3 | Blisters with edema |

Severity was assessed by comparing the numbers of subjects with responses graded as 2 (edema) or 3 (blisters).

Admission of Subjects

After screening, eligible subjects who had satisfactorily met all the inclusion criteria, and who had none of the exclusion criteria, were randomized, and were allocated a 3 digit study number. In addition, they were identified by first, middle, and last initials. If the subject had no middle initial, a dash was used.

Treatment Period I—Study Days 1–5

The first dose of study medication was given at 6:00 p.m. on Study Day 1 under the supervision of site personnel. (The logistics of the study required that the clock time of dosing of drug and UV exposure may vary among subjects. The relative timing was, however, kept constant, so that the p.m. dose followed the a.m. dose by 10 hours, and light tests were performed starting at 2 hours after the final a.m. dose).

Starting on Study Day 4, immediately prior to administration of the p.m. dose, the following blood samples were collected:

| Day 4 | 0 (zero) hour = 6 p.m. (immediately before p.m. dose) 2 hours = 8 p.m. |
| --- | --- |
| Day 5–8 | 14 hours = 8 a.m. 16 hours = 10 a.m. 19 hours = 1 p.m. 38 hours = 8 a.m. 62 hours = 8 a.m. 86 hours = 8 a.m. |

Two hours after the administration of the last dose of Treatment Period 1 (a.m. dose), the two randomly selected sites on each subject's back or buttocks were exposed one to UVA and UVB radiation, and one to UVA radiation alone. In order to protect the subjects from excessive radiation, as well as assess the true Minimum Erythema Dose (MED), the posttreatment irradiation doses for each subject was adjusted in accordance with their pretreatment MEDs. The following table was used to determine each subject's minimum and maximum posttreatment radiation dose:

| Pre-Drug MED $J/cm^2$ | Post-Drug radiation start at $J/cm^2$ | Maximum radiation to be applied $J/cm^2$ | Increments of change $J/cm^2$ |
| --- | --- | --- | --- |
| 30 | 5 | 30 | 5 |
| 25 | 5 | 30 | 5 |
| 20 | 2.5 | 25 | 1 × 2.5 then 4 × 5 |
| 15 | 2.5 | 15 | 5 × 2.5 |
| <15 | 1.25 | not to exceed pre-drug MED | 1.25 and 2.5 to reach pre-drug MED |

For postdrug MED determination, 2 sites each with six 1 $cm^2$ patches on the back or buttocks, randomly selected by the study site, were irradiated using the above dosing schedule. Any of the sites of radiation were used only once throughout the study including the screening.

The lowest of the MED values for 24, 48 and 72 hours (considered delayed MED) were used as the posttreatment MED for that subject in the analysis. Severity of reactions causing edema and/or blisters were graded by the grading system described hereinabove.

Immediately after exposure (zero hour), and at 3, 6, 24, 48 and 72 hours post-radiation, each of the sites were read and graded in the manner described hereinabove.

Any adverse events or symptoms occurring during Treatment Period 1 were recorded on the appropriate CRF. Any skin reaction outside of the 8 radiation sites was reported appropriately as an adverse event.

Wash Study Days 6–10

Subjects were required to stay at the study site between the hours of 0700 hours and 1900 hours (sooner than 0700 hours or later than 1900 hours if the procedure required) on wash days 6, 7 and 8. During these days, the 24, 48 and 72 hours evaluation of MED and grading of radiation sites took place.

There were no procedures scheduled for Study Day 9. Subjects were not required to stay in the research facilities on Day 9, but were required to return to these facilities on Study Day 10. The subjects were instructed to avoid sunlight, and to wear protective clothing and special sunscreen provided to them by the study site. Subjects were required to report all sun exposures, as well as any adverse events, symptoms or medications they may have taken on Study Day 9.

Subjects returned to the study site at 0700 hours on Study Day 10. The two skin sites which had been pre-assigned for radiation (back and buttocks) were radiated in the manner described hereinabove.

Adverse events, symptoms or medications taken during the 5 day wash were recorded on appropriate CRFs. Any skin reaction occurring outside of the radiation sites was reported appropriately as an adverse event.

Treatment Period II (Cross-Over Phase)—Study Days 11–15

Subjects returned to the site by 0700 hours on Study Day 11.

MED determination and grading at 25 hours postradiation was performed in the manner described hereinabove. The purpose of this MED determination was to evaluate whether the subject's MED, after 5 days of washout, had returned to baseline (predrug) levels which, as described hereinabove, had been established earlier. The MED value obtained here served as the baseline for adjustments of posttreatment 2 radiation dosing (see below).

A pK plasma sample was taken prior to the first p.m. dose of the Treatment Period II.

The first dose of study medication was given at 1800 hours (or at an adjusted time) of Study Day 11 under the supervision of site personnel. (The logistics of the study required that the clock time of dosing of drug and UV radiation exposure may vary among subjects. The relative timing was, however, kept constant, so that the p.m. dose followed the a.m. dose by 10 hours, and light tests were performed 2 hours after the final a.m. dose).

Starting on Study Day 14, prior to, and following, administration of the p.m. dose, blood samples were collected as follows:

| Day 14 | 0 (zero) hour = 6 p.m. |
| | (immediately before p.m. dose) |
| | 2 hours = 8 p.m. |
| | 5 hours = 11 p.m. |
| Day 15–18 | 14 hours = 8 a.m. |
| | 16 hours = 10 a.m. |
| | 19 hours = 1 p.m. |
| | 38 hours = 8 a.m. |
| | 62 hours = 8 a.m. |
| | 86 hours = 8 a.m. |

Two hours after the administration of the last dose of Treatment Period II (a.m. dose), two randomly selected sites on each subject's back or buttocks were separately exposed to UVA and UVB radiation, and to UVA radiation alone. In order to protect the subjects from excessive radiation, as well as to assess the true Minimum Erythema Dose (MED), the posttreatment irradiation doses for each subject was adjusted in accordance with their pretreatment (screening-baseline) MEDs. The same table presented hereinabove was used to determine each subject's minimum and maximum posttreatment radiation dose.

For postdrug MED determination, 2 sites each of six 1 $cm^2$ patches on the back or buttocks, randomly selected by the study site, were irradiated using the above-described dosing schedule. Each of the sites of radiation were used only once throughout the study, including the screening.

The lowest of the MED values for 24, 48 and 72 hours (considered delayed MED) were used as the posttreatment MED for that subject in the analysis. Severity of erythema, presence of edema and/or blisters were graded according to the same grading system presented hereinabove.

Immediately after exposure, and at 3, 6, 24, 48 and 72 hours post-radiation, each of the sites was read and graded in the manner described hereinabove.

Any adverse events or symptoms occurring during Treatment Period II were recorded on the appropriate CRF. Any skin reaction occurring outside radiation sites was reported appropriately as an adverse event. Any medication(s), other than study medication, taken by the subject was also recorded.

Post-Treatment Period

Following the grading of the radiation sites at 72 hours after Treatment Period II, a physical examination including the vital signs and 12-lead EKG was conducted. At this time, symptoms were assessed and laboratory tests, including a serum pregnancy test for all female participants, was performed. In addition, clinical laboratory values that have become significantly abnormal during the study were reported and followed further, where necessary, until resolved.

Case Report Forms (CRFs)

Subject source documents were the physician's subject records maintained at the study site. In most cases, the source documents were the hospital's or the physician's chart. In cases where the source documents were the hospital's or the physician's chart, the information collected on the CRFs matched those charts.

It was the Investigator's responsibility to ensure completion of, and to review and approve, all CRFs. Individual CRFs were signed by the Investigator, or by a Sub-Investigator. These signatures served to attest that the information contained on the CRFs was true. At all times, the Investigator had final responsibility for the accuracy and authenticity of all clinical and laboratory data entered on the CRFs.

Military time was used for all time entries.

Clinical Supplies

The Investigator maintained adequate records showing the receipt, dispensing, return, or other disposition of the investigational drug, including the date, quantity, batch or code number, and identification of subjects (number, initials) who received study drug.

Blood Chemistry/Hematology

Pre-study and post-study mean results of serum concentration of lomefloxacin hydrochloride and standard deviations were determined, together with counts of observations above and below the laboratory normal range.

A baseline blood sample for drug assay was taken prior to the first administration of study drug. Blood samples for drug concentration determination were obtained immediately before administering the evening dose of study drug on Study Days 4 (Treatment Period 1) and 14 (Treatment Period 2), with additional samples collected at 2, 14, 16, 19, 38, 62 and 86 hours after administering the last dose.

The following were instructions given for human blood collection, and for processing for the determination of plasma lomefloxacin hydrochloride concentrations:

1. Place tourniquet on the arm before blood is collected.
2. Make venipuncture with a 21-gauge needle and remove tourniquet.
3. Collect blood into 10 ml labeled vacutainer containing sodium heparin over a period of less than 30 seconds.
4. Invert (gently) the vacutainer four times to mix and place in an ice bath, protected from direct light, prior to centrifugation.

5. Begin centrifugation within 15 minutes after blood collection, i.e., after removal of the vacutainer from the subject.
6. Centrifuge the vacutainer at 1200×g for 10 minutes at 4° C.
7. Remove plasma immediately and place into an appropriately labeled cryotube.
8. Cap the cryotube and immediately place in a freeze at −20° C.
9. Keep plasma frozen until analyzed.

Note:

(1) Steps 4 through 8 (specimen processing) were to be carried out within 30 minutes after blood collection, i.e., after removal of the vacutainer from the subject.

(2) Samples were shipped on dry ice to Pharmaco-LSR (Richmond, Va.).

(3) Blood samples were not allowed to sit or be stored under direct light to prevent potential photodecomposition of lomefloxacin hydrochloride.

Clinical Laboratory Data

Clinical laboratory data were analyzed for both treatment sequence groups combined using scatterplots, t-tests and shift tables, which are known by those of skill in the art. Changes from baseline to posttreatment were noted and reviewed for clinical and statistical significance.

Photoreaction Analyses

Most drug related photoreactions are induced by wavelengths of 320 to 400 nm, the UVA range, therefore, the primary analysis focused on UVA radiation. In addition, the delayed MEDs, which offer better consistency and reproducibility than immediate MEDs, were considered to be a primary variable for the assessment of MED values.

Since a significant number of baseline MED values for Treatment Period 2 could not be established, even with application of the maximum amount of UVA radiation allowed by the protocol (30 J/cm$^2$, based on predetermined acceptable levels of exposure to UVA radiation), the primary analysis focused on the data for Treatment Period 1.

Within-treatment differences between delayed $MED_{UVA}$s and baseline $MED_{UVA}$s were tested using the signed rank test, which is known by those of skill in the art. Between treatment comparisons of these differences were tested using a two-sample t-test, which is known by those of skill in the art. To confirm the results of this analysis, those baseline $MED_{UVA}$s that could not be defined for Treatment Period 2 were set to 35 J/cm$^2$, and the data analyzed using an ANOVA model, which is known by those of skill in the art, with sequence, subject within sequence, period and treatment as independent factors.

The same statistical methods were used to detect between and within treatment differences in change from baseline to posttreatment immediate $MED_{UVA}$s.

Identical methods were applied to the UVA+UVB data for delayed and immediate $MED_{UVA+UVB}$ analysis.

The proportion of subjects with UVA-induced edema or blisters at 0, 3, 6, 24, 48 and 72 hours following irradiation was summarized and displayed graphically for each treatment group.

The relationship between plasma concentration at time of irradiation and delayed $MED_{UVA}$ was explored using regression analysis by testing the equality of the slopes of the regression of delayed $MED_{UVA}$ on plasma concentration, obtaining estimates of the parameters of the regression line, and determining the correlation coefficient.

An alternate, more conservative set of $MED_{UVA}$s was identified where $MED_{UVA}$ was defined as a minimal perceptible erythema not necessarily covering the full size of a one square centimeter patch. These data were then analyzed in two ways using an ANOVA model with sequence, subject within sequence, period and treatment as independent factors. The first analysis was limited to subjects who had measurable baseline and delayed $MED_{UVA}$s for at least one treatment period. The second analysis was performed after the $MED_{UVA}$s greater than 30 J/cm$^2$ were arbitrarily set at 35 J/cm$^2$.

Clinical Laboratory Data

Clinical laboratory data were analyzed for both treatment sequence groups combined using scatterplots, t-tests and shift tables, which are known by those of skill in the art. Changes from baseline to posttreatment were noted and reviewed for clinical and statistical significance.

Significant Testing

Statistical tests were two-sided and conducted at the 5% level of significance.

Results

The statistical and other results of this study are discussed hereinbelow, and are presented in Tables 2–7 hereinbelow, and in FIGS. 1–12 hereinbelow. Tables 2–5 display descriptive statistics, and FIGS. 2–5 and 9–12 graphically display baseline and MED values for Treatment Period 1. The severity of erythema as assessed by the presence of edema (Grade 2), or the presence of blisters (Grade 3) for Treatment Period 1 is displayed in FIG. 6 and in Table 7. A plot of lomefloxacin HCl plasma concentration (Table 6) and delayed $MED_{UVA}$s over time is displayed in FIGS. 7 and 8 for a.m. and p.m. dosing in Treatment Period 1.

No statistically significant treatment sequence differences were observed for any of the baseline demographics for all subjects (p≧0.118 for all comparisons). Hence, the demographic information for both treatment sequence groups is combined.

The primary analysis performed in this study was focused on comparing the MED for the two dosing groups of lomefloxacin hydrochloride (p.m. vs a.m.). The difference in MED from baseline to posttreatment was analyzed using an analysis of variance model with treatment (a.m./p.m.), sequence, subject within sequence, and period as independent factors. If normality assumptions were not met, a nonparametric method of analyzing data from cross-over studies was used, as described in B. Jones, et al., *Design and Analysis of Cross-Over Trials* (Chapman & Hall, London, N.Y., 1989). Grading scores of severity of erythema were analyzed using the methods described hereinabove. For these scores, a separate analysis was performed for 0, 3, 6, 24, 48 and 72 hour responses.

The relationship between serum concentration of lomefloxacin and MED measurements was explored using regression analysis.

Because a significant number of baseline MED values in the second period were not established, 35 J/cm$^2$, the next possible increment level, was substituted for these missing values in order to be able to analyze the data using a crossover mode. The results from analysis of variance on the ranks of UVA data indicated a statistically significant period effect (p=0.005). Because of this significance, and 78% missing baselines for Treatment Period 2, the data for only the first period was analyzed. The number of subjects in each treatment group was sufficient in Treatment Period 1 to hold the above-described justification of sample size specified herein.

Tables 2–5, which are presented hereinbelow, display descriptive statistics for MED values for UVA radiation alone, and for UVA and UVB radiation, for Treatment Period 1. Table 6, which is also presented hereinbelow, displays plasma concentration data for Treatment Period 1. The severity of erythema as assessed by the presence of edema (Grade=2) or presence of blisters (Grade=3) for Treatment Period 1 is displayed in Table 7, which is presented hereinbelow.

Figure 4:
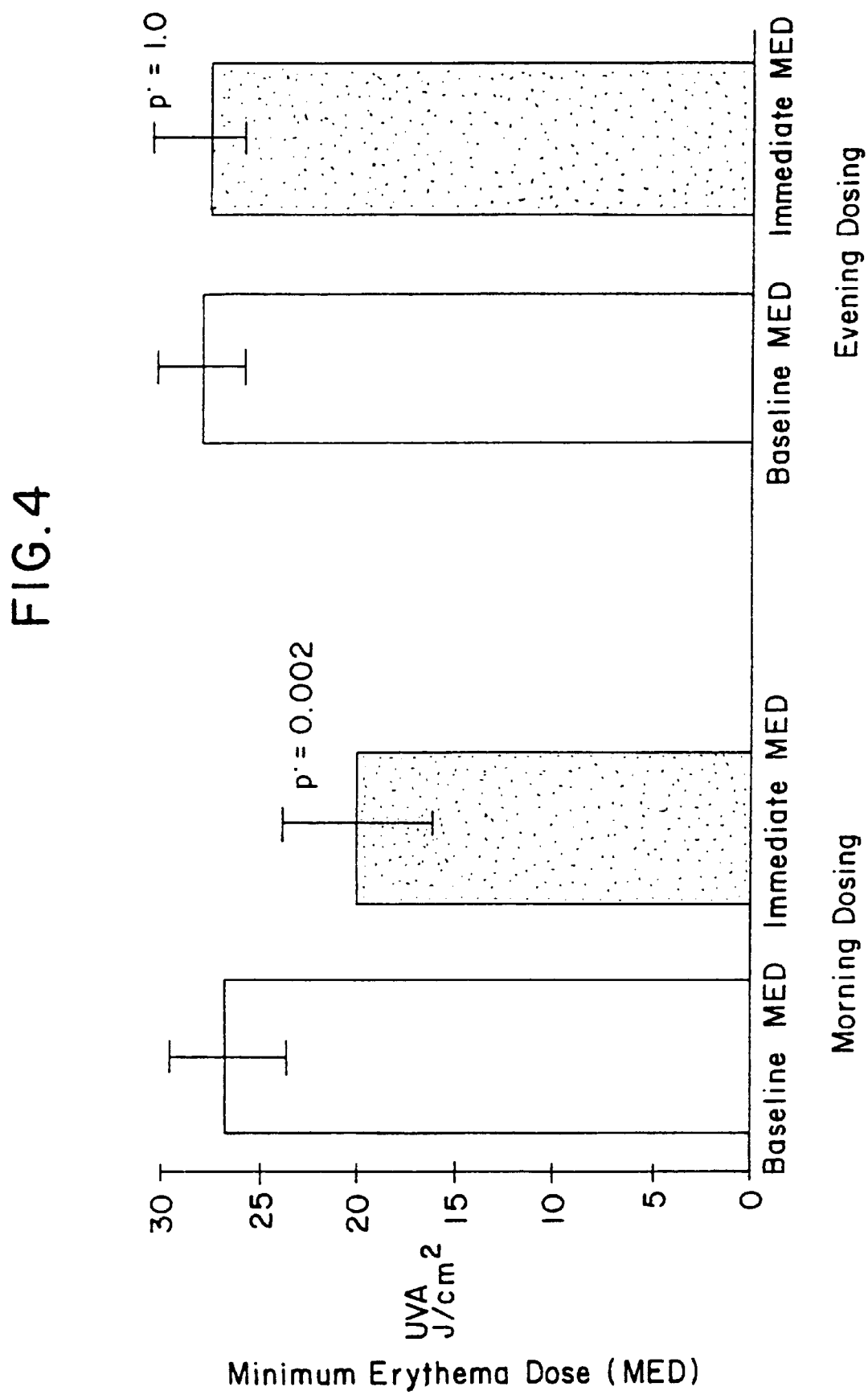
FIG. 4 graphically displays mean baseline and delayed Minimum Erythema Dose (MED) values in $J/cm^2$ (UVA radiation) for the morning dosing and evening dosing lomefloxacin hydrochloride groups in Treatment Period 1 in the study described in detail hereinbelow in Example 5. The bars represent standard deviations, and the p values are from the within treatment comparison of baseline versus post-treatment delayed MED.
Figure 5:
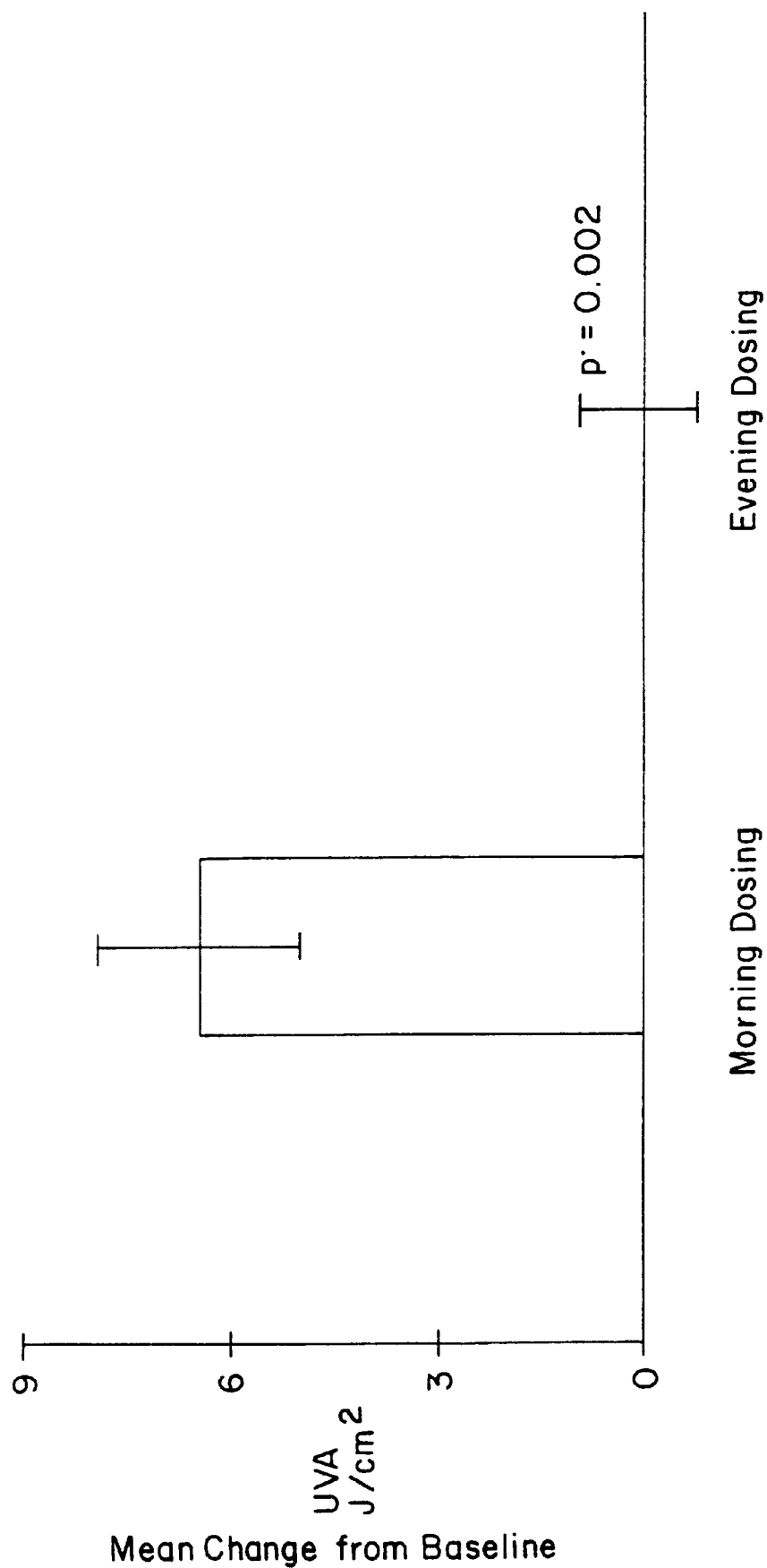
FIG. 5 graphically displays the change from baseline in mean delayed Minimum Erythema Dose (MED) values in $J/cm^2$ (UVA radiation) for the morning dosing and evening dosing lomefloxacin hydrochloride groups in Treatment Period 1 in the study described in detail hereinbelow in Example 5. The bars represent standard errors, and the p value is from between treatment comparison of change from baseline to post-treatment delayed MED.

Treatment Period 1 UVA data showed that the mean delayed $MED_{UVA}$s were statistically significantly different from the mean baseline $MED_{UVA}$s for the a.m. lomefloxacin HCl dosing group (mean=6.5, p=0.002, Table 2, FIG. 4). For the p.m. lomefloxacin HCl dosing group, no difference was observed between the baseline and posttreatment means for delayed $MED_{UVA}$ (p=1.000, Table 2, FIG. 4). There was a statistically significant difference between mean changes for a.m. and p.m. dosing (p=0.002, FIG. 5).

Figure 2:
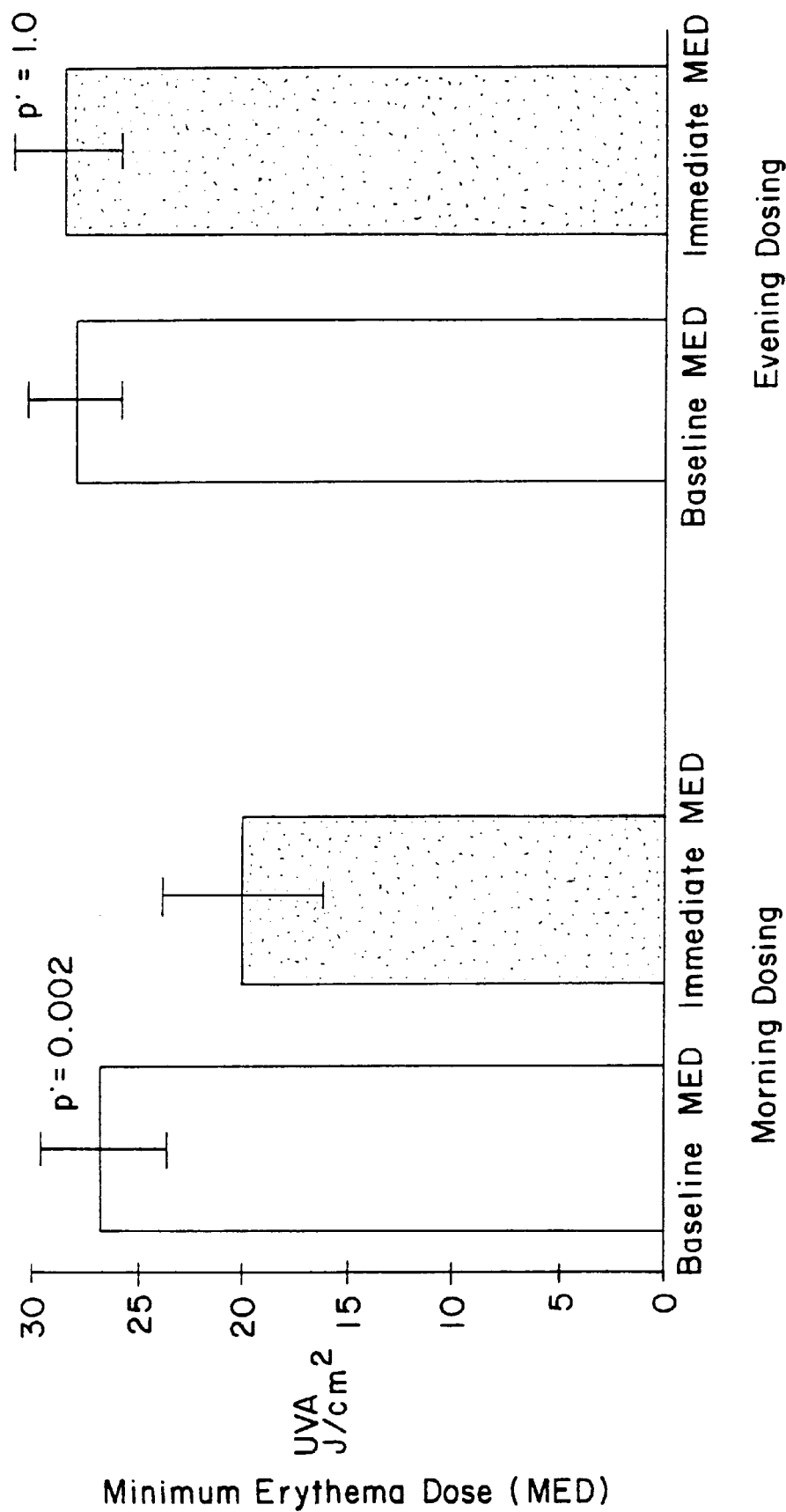
FIG. 2 graphically displays mean baseline and immediate Minimum Erythema Dose (MED) values in $J/cm^2$ (UVA radiation) for the morning dosing and evening dosing lomefloxacin hydrochloride groups in Treatment Period 1 in the study described in detail hereinbelow in Example 5. The bars represent standard deviations, and the p values are from the within treatment comparison of baseline versus post-treatment immediate MED.
Figure 3:
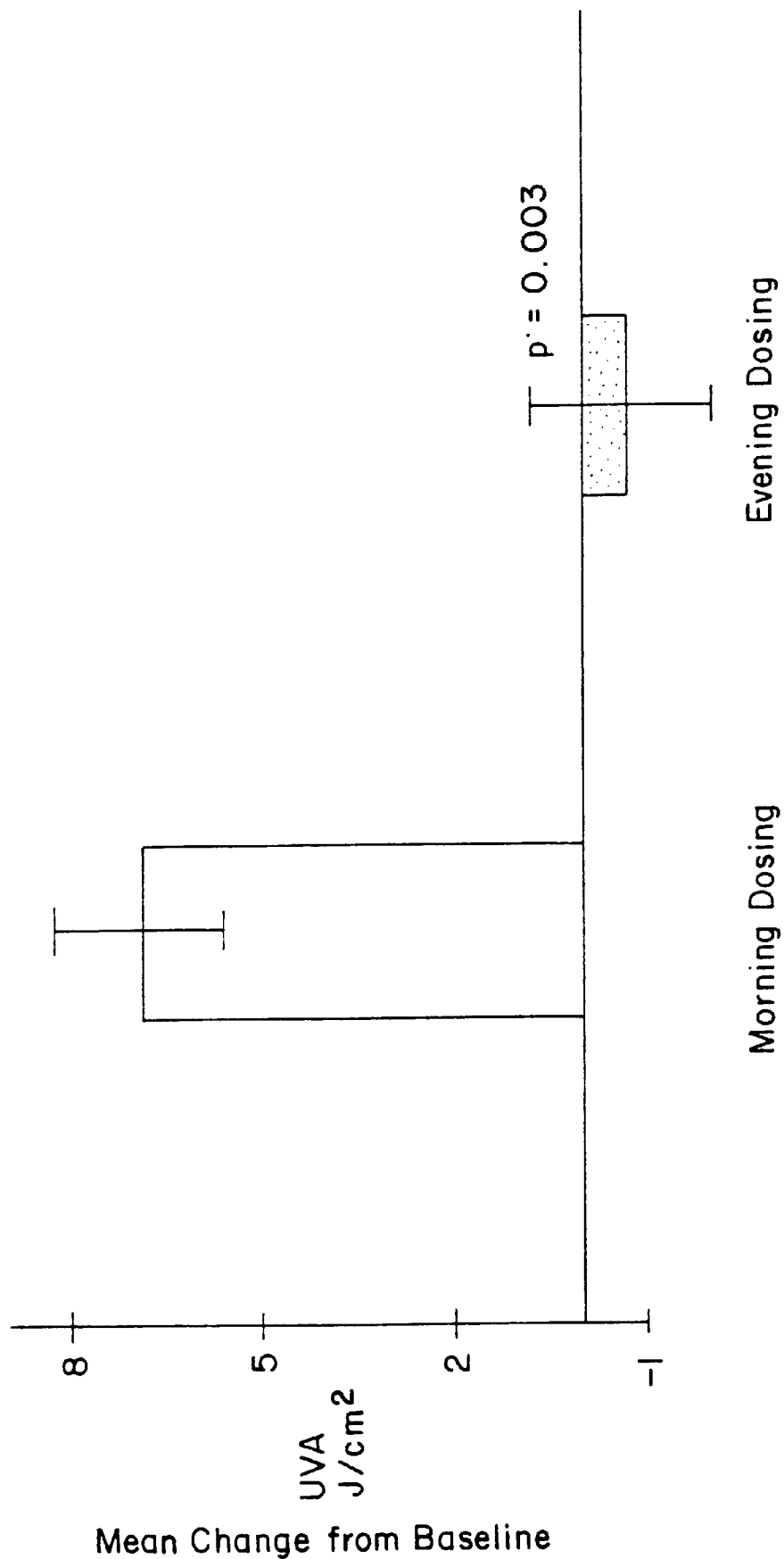
FIG. 3 graphically displays the change from baseline in mean immediate Minimum Erythema Dose (MED) values in $J/cm^2$ (UVA radiation) for the morning dosing and evening dosing lomefloxacin hydrochloride groups in Treatment Period 1 in the study described in detail hereinbelow in Example 5. The bars represent standard errors, and the p value is from between treatment comparison of change from baseline to post-treatment immediate MED.

Treatment Period 1 UVA data showed that the mean immediate $MED_{UVA}$s were statistically significantly different from the mean baseline $MED_{UVA}$s for the a.m. lomefloxacin HCl dosing group (mean=6.9, p=0.002, Table 4, FIG. 2). For the p.m. lomefloxacin HCl dosing group, no difference was observed between the baseline and posttreatment means for immediate $MED_{UVA}$ (mean=−0.6, p=1.000, Table 4, FIG. 2). There was a statistically significant difference between mean changes for a.m. and p.m. dosing (p=0.003, FIG. 3).

Figure 6:
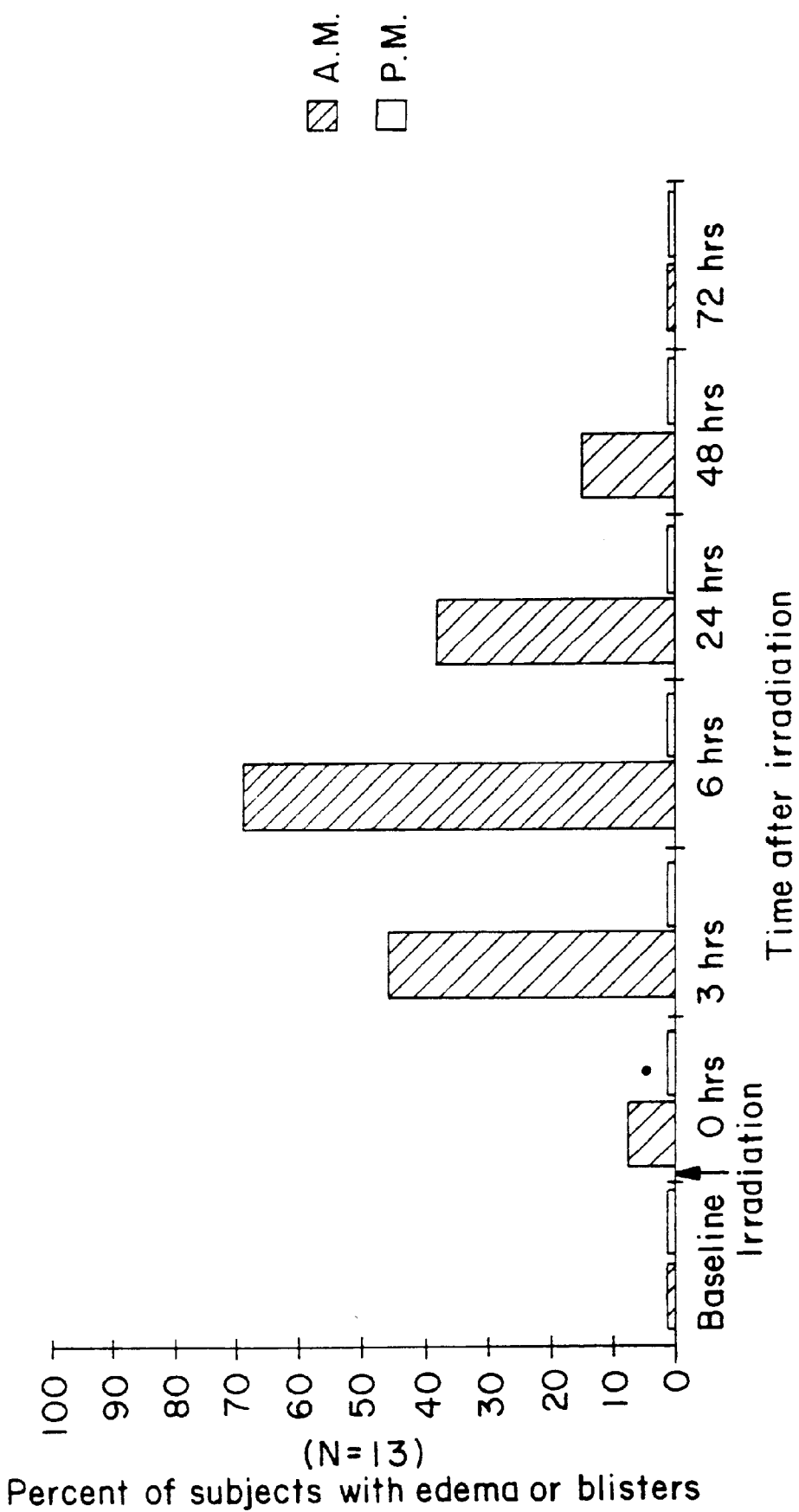
FIG. 6 graphically displays the severity of UVA-induced photoreactions (edema or blisters) for the morning dosing and evening dosing lomefloxacin hydrochloride groups in the study described in detail hereinbelow in Example 5.
Figure 7:
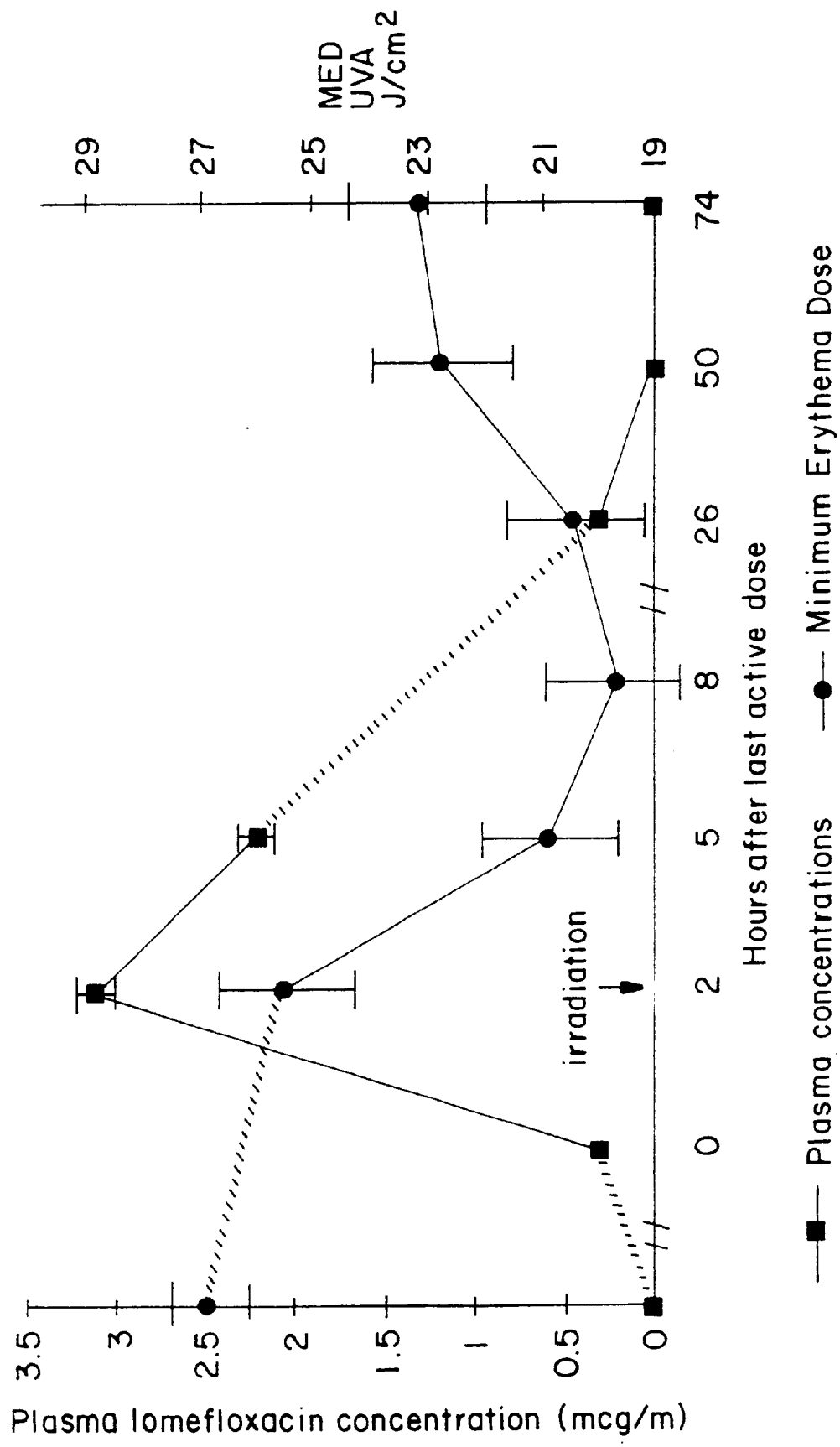
FIG. 7 is a plot of plasma lomefloxacin hydrochloride concentration (mcg/ml) versus hours after last active dose versus mean UVA Minimum Erythema Dose (MED) values in $J/cm^2$ for volunteers receiving morning doses of lomefloxacin hydrochloride, as described hereinbelow in detail in Example 5. The bars represent standard errors. The squares represent the plasma concentration of lomefloxacin hydrochloride, and the circles represent minimum erythema dose.
Figure 8:
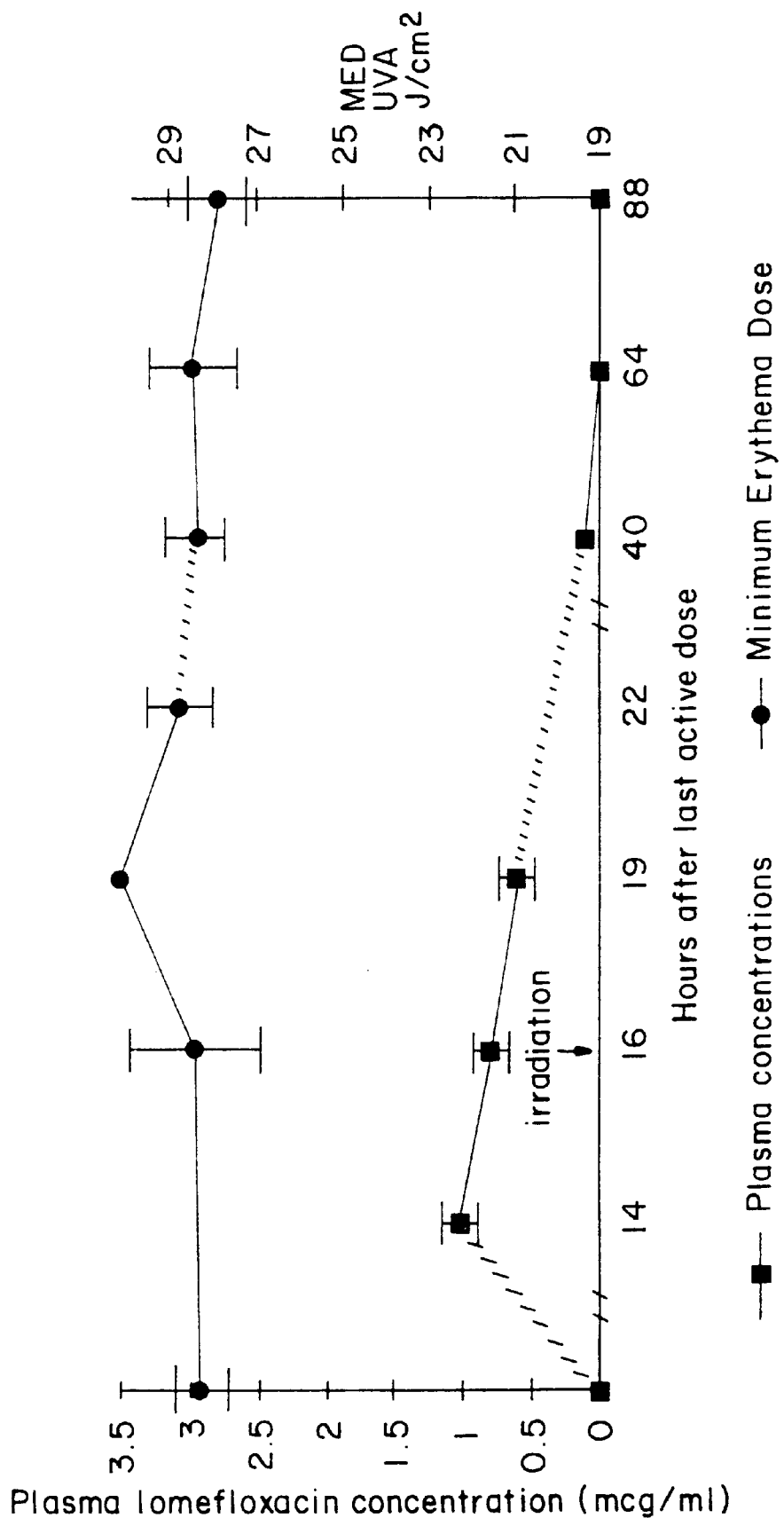
FIG. 8 is a plot of plasma lomefloxacin hydrochloride concentration (mcg/ml) and UVA Minimum Erythema Dose (MED) values in J/cm² versus hours after last active dose for volunteers receiving evening doses of lomefloxacin hydrochloride, as described hereinbelow in detail in Example 5. The bars represent standard errors. The squares represent the plasma concentration of lomefloxacin hydrochloride, and the circles represent minimum erythema dose.

The assessment of the severity of the UVA-induced photoreactions showed responses of edema or blisters in the a.m. dosing group (Table 7, FIG. 6). Edema or blisters occurred on the specified radiation sites with greatest frequency at the 6 hour post-radiation evaluation with 9 subjects (69%) having such responses. None of the subjects in the p.m. dosing group had a phototoxic response with edema or blisters at any of the time periods assessed.

The relationship between delayed $MED_{UVA}$ and lomefloxacin HCl plasma concentration at irradiation was explored using regression analysis. There was a statistically significant negative linear relationship between plasma lomefloxacin HCl concentration and $MED_{UVA}$ (slope=−4.99, p<0.001). The correlation coefficient was −0.72, indicating a moderately strong inverse relationship between plasma concentration and delayed $MED_{UVA}$. As plasma concentration decreased with elapsed time after drug administration, the energy required for an $MED_{UVA}$ increased.

The secondary analysis of this study included assessments of immediate and delayed $MED_{UVA+UVB}$s produced by solar simulated full spectrum UVA+UVB wavelengths. These data are presented in Tables 3 and 5, and are graphically displayed in FIGS. 9–12.

Figure 9:
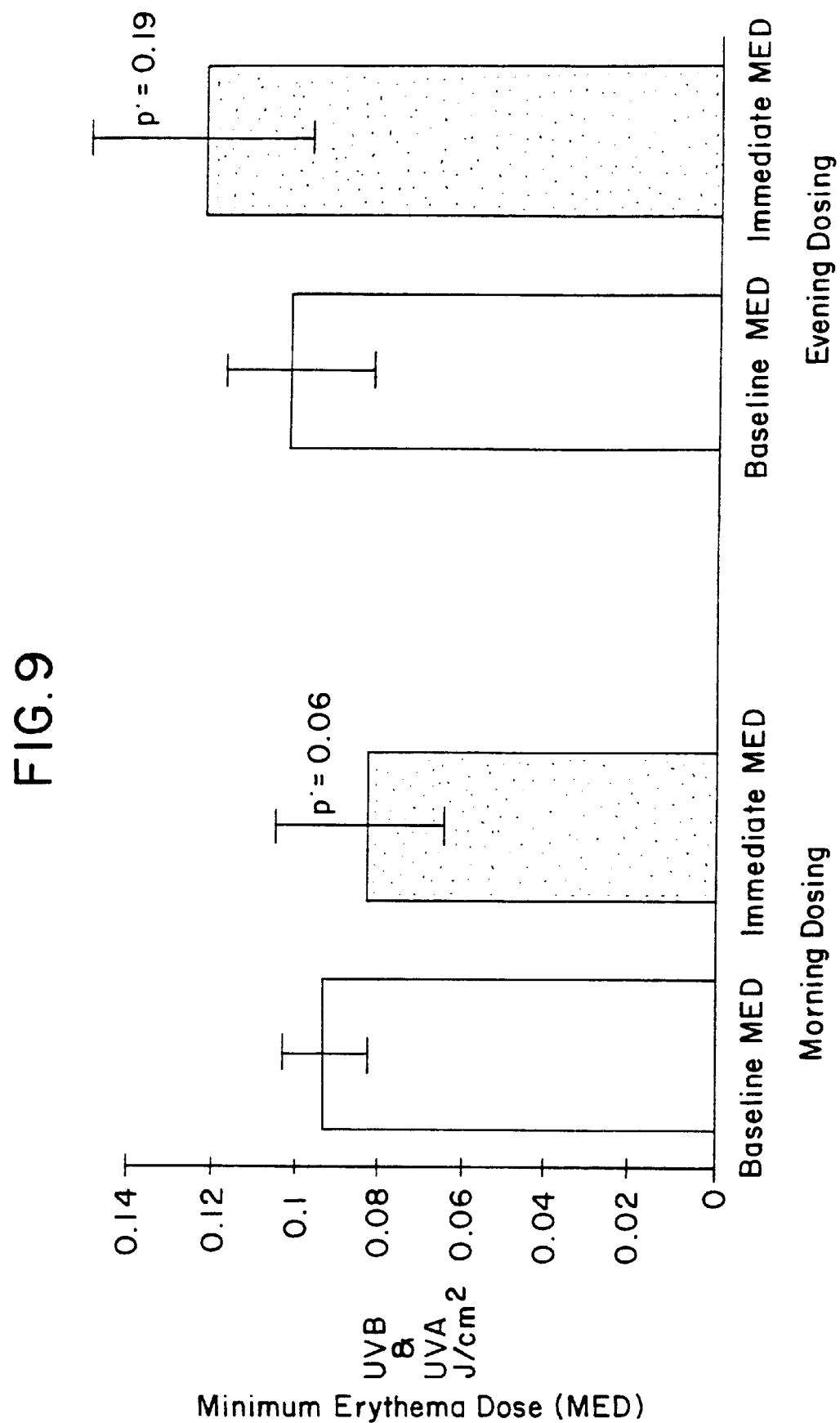
FIG. 9 graphically displays mean baseline and immediate Minimum Erythema Dose (MED) values in J/cm² (full spectrum UVA plus UVB radiation) for the morning dosing and evening dosing lomefloxacin hydrochloride groups in Treatment Period 1 in the study described in detail hereinbelow in Example 5. The bars represent standard deviations, and the p values are from the within treatment comparison of baseline versus post-treatment immediate MED.
Figure 10:
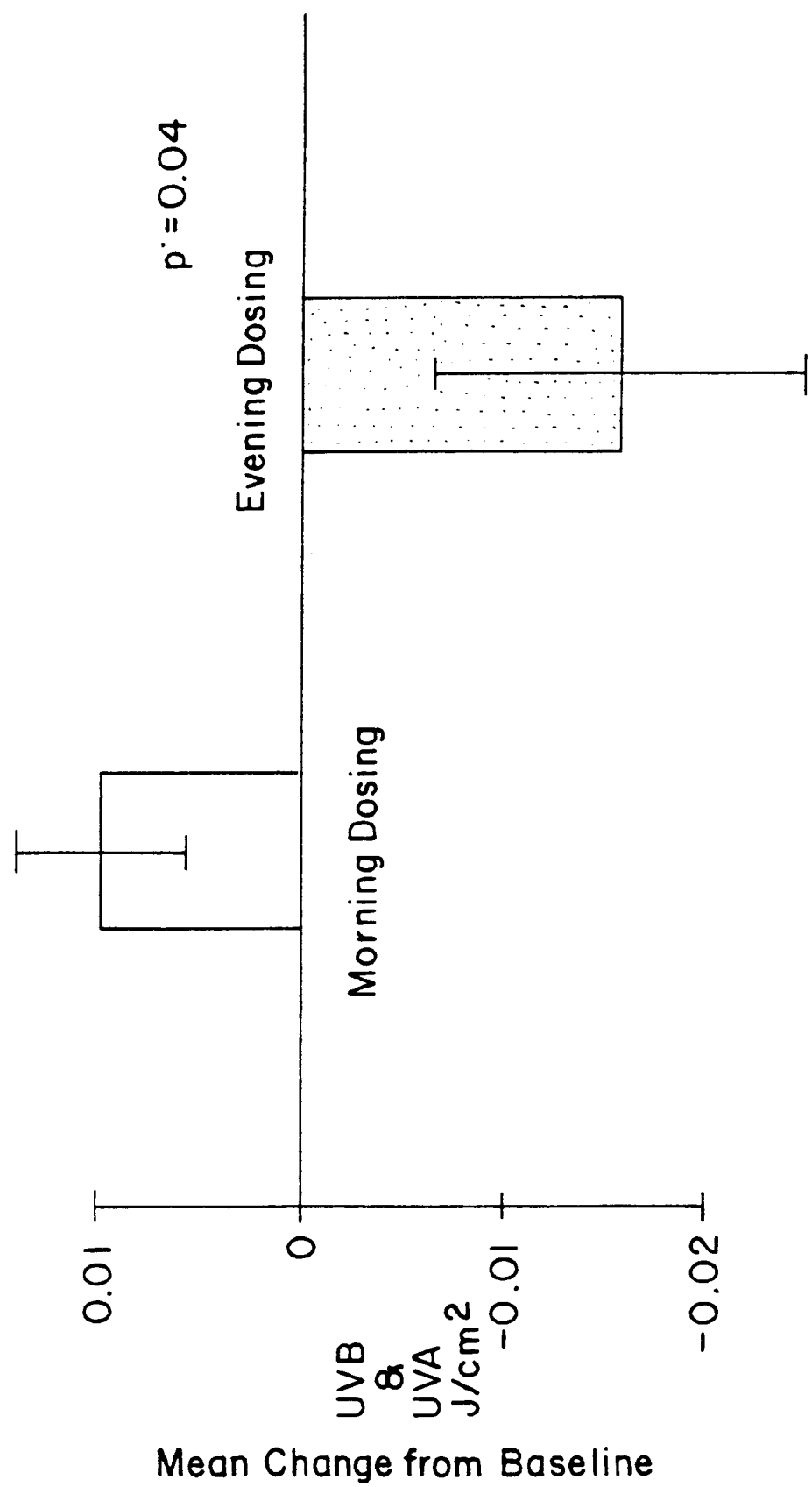
FIG. 10 graphically displays the change from baseline in mean immediate Minimum Erythema Dose (MED) values in J/cm² (full spectrum UVA plus UVB radiation) for the morning dosing and evening dosing lomefloxacin hydrochloride groups in Treatment Period 1 in the study described in detail hereinbelow in Example 5. The bars represent standard errors, and the p value is from between treatment comparison of change from baseline to post-treatment immediate MED.
Figure 11:
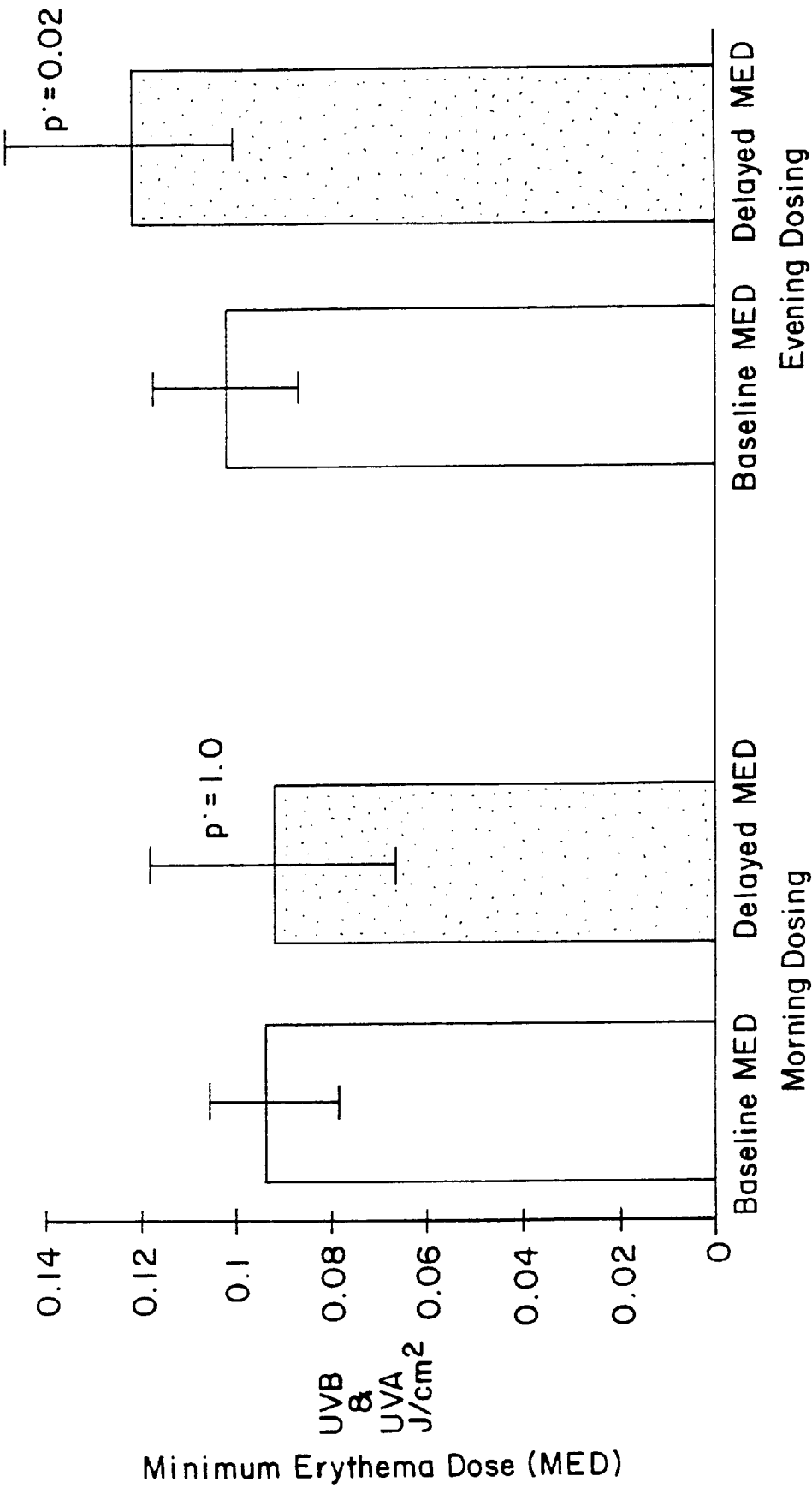
FIG. 11 graphically displays mean baseline and delayed Minimum Erythema Dose (MED) values in J/cm² (full spectrum UVA plus UVB radiation) for the morning dosing and evening dosing lomefloxacin hydrochloride groups in Treatment Period 1 in the study described in detail hereinbelow in Example 5. The bars represent standard deviations, and the p values are from the within treatment comparison of baseline versus post-treatment delayed MED.
Figure 12:
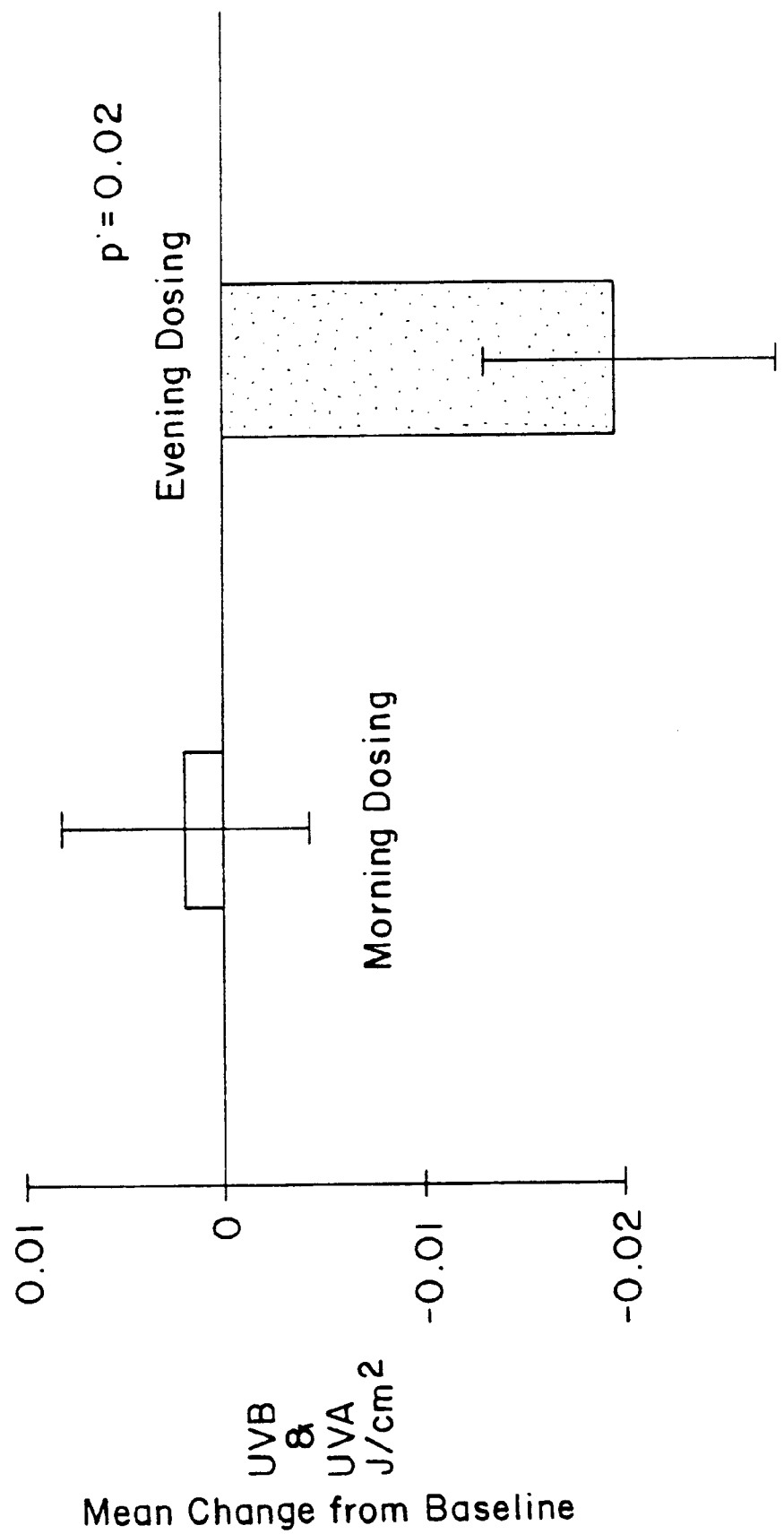
FIG. 12 graphically displays the change from baseline in mean delayed Minimum Erythema Dose (MED) values in J/cm² (full spectrum UVA plus UVB radiation) for the morning dosing and evening dosing lomefloxacin hydrochloride groups in Treatment Period 1 in the study described in detail hereinbelow in Example 5. The bars represent standard errors, and the p value is from between treatment comparison of change from baseline to post-treatment delayed MED.

The full spectrum UVA+UVB data indicate that, in the a.m. lomefloxacin HCl dosing group, neither the changes between baseline and posttreatment immediate $MED_{UVA+UVB}$, nor between baseline and posttreatment delayed $MED_{UVA+UVB}$, were statistically significant (immediate $MED_{UVA+UVB}$ mean=0.010, p=0.06, Table 5, FIG. 9; delayed $MED_{UVA+UVB}$ mean=0.002, p=1.000, Table 3, FIG. 11). The full spectrum UVA+UVB data indicate that in the p.m. lomefloxacin HCl dosing group, the changes between baseline and posttreatment immediate $MED_{UVA+UVB}$ were not statistically significant (mean=−0.016, p=0.19, Table 5, FIG. 9), but the changes between baseline and posttreatment delayed $MED_{UVA+UVB}$ were statistically significant (mean=−0.021, p=0.02, Table 3, FIG. 11). There was a statistically significant difference between the a.m. and p.m. dosing group changes for immediate and delayed $MED_{UVA+UVB}$s (immediate, p=0.04, FIG. 10; delayed, p=0.02, FIG. 12).

The assessment of the severity of the UVA+UVB radiation-induced photoreactions showed no change in a.m. or p.m. dosing when compared with their respective baselines (Table 7).

An exploratory, conservative analysis of the UVA data obtained by redefining $MED_{UVA}$ as minimal perceptible erythema not necessarily covering the full size of a one square centimeter patch, produced results similar to those reported earlier. The difference between baseline and posttreatment delayed $MED_{UVA}$ was analyzed using an ANOVA model with subject, subject within sequence, treatment and period as independent factors. Whether the undefined $MED_{UVA}$s were set as "missing," or set to the arbitrary value of 35 J/cm$^2$, results were similar, showing a statistically significant treatment effect (p=0.002 when set as missing, and p=0.003 when assigned values of 35 J/cm$^2$), but none of the other effects were statistically significant.

In summary, results of changes in $MED_{UVA}$s indicate that the skin of lomefloxacin HCl treated subjects is less sensitive to light when lomefloxacin HCl was administered 16 hours prior to UVA exposure (evening dosing) than when administered two hours prior to UVA exposure (morning dosing). The results were consistent for immediate and delayed evaluations. In addition, plasma levels at the time of irradiation have a significant negative linear relationship with delayed MED induced by UVA radiation. As plasma concentration decreased, the amount of energy required for an $MED_{UVA}$ increased.

When exposure occurred after morning dosing (2 hour interval), sixty-nine percent of the subjects experienced edema or blisters on the sites of radiation. These findings are consistent with the reported "exaggerated sunburn" that is characteristic of drug-induced photoreactions, and serve to validate the experimental design and outcome of this study. None of the subjects developed these responses when exposure occurred after evening dosing (16 hour interval).

The pharmacokinetic/pharmacodynamic results of this study indicate that, as the drug plasma concentrations decrease, the amount of energy required for an $MED_{UVA}$ increases. The plasma concentration peaks approximately two hours following dosing with lomefloxacin HCl, about the same time the UVA radiation was applied when subjects received an a.m. dose. A negative correlation between plasma lomefloxacin HCl concentrations at time of UVA exposure, and the extent of skin response to UV radiation, was observed.

FIGS. 1–12 show that MAXAQUIN® administered approximately sixteen hours prior to UVA irradiation exposure (evening dosing) is significantly less phototoxic than MAXAQUIN® administered two hours prior to UVA irradiation exposure (morning dosing). There exists a positive correlation between MAXAQUIN® plasma concentrations at the time of UVA irradiation and the extent of photosensitivity and/or phototoxicity. Dosing of MAXAQUIN® approximately sixteen hours before exposure to UVA irradiation (evening dosing) will decrease or completely eliminate the extent of photosensitivity and/or phototoxicity caused by the administration of MAXAQUIN®.

FIGS. 1–12 show that UVA irradiation two hours after administration of MAXAQUIN® will generally result in significant photosensitivity and/or phototoxicity reactions, whereas UVA irradiation sixteen hours after administration of MAXAQUIN® will generally not cause photosensitivity and/or phototoxicity reactions.

It can be concluded from this clinical study that once-a-day evening dosing of MAXAQUIN® will reduce or completely prevent the risk of photosensitivity and/or phototoxicity reactions during peak daylight hours of the following day. Longer intervals (16 hours versus 2 hours) between lomefloxacin HCl dosing and exposure to UVA radiation emitted by a solar simulator (i.e., evening versus morning dosing) reduces the potential risk of photoreaction, as assessed by comparison of differences between posttreatment versus baseline $MED_{UVA}$s. The mean decrease from baseline to posttreatment UVA-induced MEDs was significantly higher in the a.m. dosing group than in the p.m. dosing group. UVA-induced reactions of edema and occasionally blisters on the sites of radiation were observed only in subjects in the a.m. dosing group, and not in subjects in the p.m. dosing group.

TABLE 2

| SUBJECT ID | STUDY DRUG | BASELINE | 24 H | 48 H | 72 H | DELAYED MED | CHANGE BASELINE |
|---|---|---|---|---|---|---|---|
| \multicolumn{8}{c}{DELAYED MINIMAL ERYTHEMA DOSE (MED) UVA EXPOSURE - PERIOD I/AM TREATMENT} |
| 252-US0001-0001 | AM/PM | 30.000 | 10.000 | 15.000 | 15.000 | 10.000 | 20.000 |
| 252-US0001-0002 | AM/PM | 25.000 | 20.000 | 25.000 | 25.000 | 20.000 | 5.000 |
| 252-US0001-0005 | AM/PM | 25.000 | 15.000 | 15.000 | 20.000 | 15.000 | 10.000 |
| 252-US0001-0008 | AM/PM | 25.000 | 20.000 | 30.000 | 30.000 | 20.000 | 5.000 |
| 252-US0001-0010 | AM/PM | 25.000 | 20.000 | 20.000 | 25.000 | 20.000 | 5.000 |
| 252-US0001-0012 | AM/PM | 30.000 | 20.000 | 20.000 | 20.000 | 20.000 | 10.000 |
| 252-US0001-0013 | AM/PM | 25.000 | 20.000 | 25.000 | 25.000 | 20.000 | 5.000 |
| 252-US0001-0014 | AM/PM | 25.000 | 30.000 | 30.000 | 30.000 | 30.000 | −5.000 |
| 252-US0001-0017 | AM/PM | 30.000 | 25.000 | 25.000 | 25.000 | 25.000 | 5.000 |
| 252-US0001-0019 | AM/PM | 25.000 | 25.000 | 25.000 | 20.000 | 20.000 | 5.000 |
| 252-US0001-0020 | AM/PM | 25.000 | 20.000 | 20.000 | 20.000 | 20.000 | 5.000 |
| 252-US0001-0022 | AM/PM | 30.000 | 20.000 | 25.000 | 25.000 | 20.000 | 10.000 |
| 252-US0001-0026 | AM/PM | 25.000 | 20.000 | 20.000 | 20.000 | 20.000 | 5.000 |
| 252-US0001-0028 | AM/PM | 30.000 | | | | | |
| | Mean | 26.786 | 20.385 | 22.692 | 23.077 | 20.000 | 6.538 |
| | Standard Deviation | 2.486 | 4.770 | 4.837 | 4.349 | 4.564 | 5.547 |
| | Standard Error | 0.664 | 1.323 | 1.342 | 1.206 | 1.266 | 1.538 |
| | N | 14 | 13 | 13 | 13 | 13 | 13 |
| \multicolumn{8}{c}{DELAYED MINIMAL ERYTHEMA DOSE (MED) UVA EXPOSURE - PERIOD I/PM TREATMENT} |
| 252-US0001-0003 | PM/AM | 25.000 | 30.000 | 30.000 | 30.000 | 30.000 | −5.000 |
| 252-US0001-0004 | PM/AM | 25.000 | 25.000 | 30.000 | 25.000 | 25.000 | 0.000 |
| 252-US0001-0006 | PM/AM | 25.000 | 25.000 | 20.000 | 30.000 | 20.000 | 5.000 |
| 252-US0001-0007 | PM/AM | 25.000 | 25.000 | 25.000 | 25.000 | 25.000 | 0.000 |
| 252-US0001-0009 | PM/AM | 30.000 | 30.000 | 30.000 | 30.000 | 30.000 | 0.000 |
| 252-US0001-0011 | PM/AM | 30.000 | 30.000 | 30.000 | 30.000 | 30.000 | 0.000 |
| 252-7S0001-0015 | PM/AM | 30.000 | 30.000 | 30.000 | 30.000 | 30.000 | 0.000 |
| 252-US0001-0016 | PM/AM | 30.000 | NE(a) | NE(a) | NE(a) | NE(a) | |
| 252-US0001-0018 | PM/AM | 30.000 | 30.000 | NE(a) | NE(a) | 30.000 | 0.000 |
| 252-US0001-0021 | PM/AM | 25.000 | 30.000 | 30.000 | 30.000 | 30.000 | −5.000 |
| 252-US0001-0023 | PM/AM | 30.000 | NE(a) | NE(a) | NE(a) | NE(a) | |
| 252-US0001-0024 | PM/AM | 30.000 | 30.000 | 30.000 | NE(a) | 30.000 | 0.000 |
| 252-US0001-0025 | PM/AM | 30.000 | 25.000 | 25.000 | 25.000 | 25.000 | 5.000 |
| 252-US0001-0027 | PM/AM | 30.000 | 30.000 | 30.000 | 30.000 | 30.000 | 0.000 |
| | Mean | 28.214 | 28.333 | 28.182 | 28.500 | 27.917 | 0.000 |
| | Standard Deviation | 2.486 | 2.462 | 3.371 | 2.415 | 3.343 | 3.015 |
| | Standard Error | 0.664 | 0.711 | 1.016 | 0.764 | 0.965 | 0.870 |
| | N | 14 | 12 | 11 | 10 | 12 | 12 |

TABLE 3

| SUBJECT ID | STUDY DRUG | BASELINE | 24 H | 48 H | 72 H | DELAYED MED | CHANGE BASELINE |
|---|---|---|---|---|---|---|---|
| \multicolumn{8}{c}{DELAYED MINIMAL ERYTHEMA DOSE (MED) UVA/UVB EXPOSURE - PERIOD I/AM TREATMENT} |
| 252-US0001-0001 | AM/PM | 0.060 | 0.060 | 0.075 | 0.060 | 0.060 | 0.000 |
| 252-US0001-0002 | AM/PM | 0.094 | 0.075 | 0.094 | 0.094 | 0.075 | 0.019 |
| 252-US0001-0005 | AM/PM | 0.094 | 0.060 | NE(a) | 0.075 | 0.060 | 0.034 |
| 252-US0001-0008 | AM/PM | 0.094 | NE(a) | NE(a) | NE(a) | NE(a) | |
| 252-US0001-0010 | AM/PM | 0.094 | 0.094 | 0.094 | 0.118 | 0.094 | 0.000 |
| 252-US0001-0012 | AM/PM | 0.094 | 0.094 | 0.094 | 0.094 | 0.094 | 0.000 |
| 252-US0001-0013 | AM/PM | 0.094 | 0.075 | 0.094 | 0.118 | 0.075 | 0.019 |
| 252-US0001-0014 | AM/PM | 0.094 | NE(a) | NE(a) | NE(a) | NE(a) | |
| 252-US0001-0017 | AM/PM | 0.094 | 0.118 | NE(a) | NE(a) | 0.118 | −0.024 |
| 252-US0001-0019 | AM/PM | 0.075 | 0.075 | NE(a) | NE(a) | 0.075 | 0.000 |
| 252-US0001-0020 | AM/PM | 0.094 | 0.094 | 0.118 | 0.118 | 0.094 | 0.000 |
| 252-US0001-0022 | AM/PM | 0.118 | 0.118 | 0.118 | NE(a) | 0.118 | 0.000 |
| 252-US0001-0026 | AM/PM | 0.118 | 0.148 | 0.148 | 0.148 | 0.148 | −0.030 |
| 252-US0001-0028 | AM/PM | 0.094 | | | | | |
| | Mean | 0.094 | 0.092 | 0.104 | 0.103 | 0.092 | 0.002 |
| | Standard Deviation | 0.014 | 0.027 | 0.023 | 0.028 | 0.027 | 0.018 |
| | Standard Error | 0.004 | 0.008 | 0.008 | 0.010 | 0.008 | 0.005 |
| | N | 14 | 11 | 8 | 8 | 11 | 11 |

TABLE 3-continued

| SUBJECT ID | STUDY DRUG | BASELINE | 24 H | 48 H | 72 H | DELAYED MED | CHANGE BASELINE |
|---|---|---|---|---|---|---|---|
| DELAYED MINIMAL ERYTHEMA DOSE (MED) UVA/UVB EXPOSURE - PERIOD I/PM TREATMENT ||||||||
| 252-US0001-0003 | PM/AM | 0.094 | 0.094 | NE(a) | NE(a) | 0.094 | 0.000 |
| 252-US0001-0004 | PM/AM | 0.094 | 0.094 | NE(a) | NE(a) | 0.094 | 0.000 |
| 252-US0001-0006 | PM/AM | 0.094 | NE(a) | NE(a) | NE(a) | NE(a) | |
| 252-US0001-0007 | PM/AM | 0.060 | 0.094 | NE(a) | NE(a) | 0.094 | −0.034 |
| 252-US0001-0009 | PM/AM | 0.094 | NE(a) | NE(a) | NE(a) | NE(a) | |
| 252-US0001-0011 | PM/AM | 0.094 | NE(a) | 0.118 | 0.118 | 0.118 | −0.024 |
| 252-7S0001-0015 | PM/AM | 0.118 | NE(a) | NE(a) | NE(a) | NE(a) | |
| 252-US0001-0016 | PM/AM | 0.118 | NE(a) | NE(a) | NE(a) | NE(a) | |
| 252-US0001-0018 | PM/AM | 0.118 | 0.094 | 0.094 | 0.118 | 0.094 | 0.024 |
| 252-US0001-0021 | PM/AM | 0.094 | 0.148 | NE(a) | NE(a) | 0.148 | −0.054 |
| 252-US0001-0023 | PM/AM | 0.118 | 0.148 | 0.148 | 0.148 | 0.148 | −0.030 |
| 252-US0001-0024 | PM/AM | 0.118 | 0.148 | NE(a) | NE(a) | 0.148 | −0.030 |
| 252-US0001-0025 | PM/AM | 0.118 | 0.148 | 0.148 | 0.148 | 0.148 | −0.030 |
| 252-US0001-0027 | PM/AM | 0.118 | 0.148 | NE(a) | NE(a) | 0.148 | −0.030 |
| | Mean | 0.104 | 0.124 | 0.127 | 0.133 | 0.123 | −0.021 |
| | Standard Deviation | 0.017 | 0.028 | 0.026 | 0.017 | 0.027 | 0.022 |
| | Standard Error | 0.005 | 0.009 | 0.013 | 0.009 | 0.009 | 0.007 |
| | N | 14 | 9 | 4 | 4 | 10 | 10 |

TABLE 4

| SUBJECT ID | STUDY DRUG | BASELINE | 0 H | 3 H | 6 H | IMMEDIATE MED | CHANGE BASELINE |
|---|---|---|---|---|---|---|---|
| IMMEDIATE MINIMAL ERYTHEMA DOSE (MED) UVA EXPOSURE - PERIOD I/AM TREATMENT ||||||||
| 252-US0001-0001 | AM/PM | 30.000 | 25.000 | 15.000 | 15.000 | 15.000 | 15.000 |
| 252-US0001-0002 | AM/PM | 25.000 | 30.000 | 20.000 | 20.000 | 20.000 | 5.000 |
| 252-US0001-0005 | AM/PM | 25.000 | 25.000 | 15.000 | 15.000 | 15.000 | 10.000 |
| 252-US0001-0008 | AM/PM | 25.000 | NE(a) | 25.000 | 20.000 | 20.000 | 5.000 |
| 252-US0001-0010 | AM/PM | 25.000 | 25.000 | 20.000 | 20.000 | 20.000 | 5.000 |
| 252-US0001-0012 | AM/PM | 30.000 | 25.000 | 20.000 | 20.000 | 20.000 | 10.000 |
| 252-US0001-0013 | AM/PM | 25.000 | 30.000 | 25.000 | 20.000 | 20.000 | 5.000 |
| 252-US0001-0014 | AM/PM | 25.000 | NE(a) | NE(a) | 30.000 | 30.000 | −5.000 |
| 252-US0001-0017 | AM/PM | 30.000 | NE(a) | 25.000 | 25.000 | 25.000 | 5.000 |
| 252-US0001-0019 | AM/PM | 25.000 | 30.000 | 25.000 | 20.000 | 20.000 | 5.000 |
| 252-US0001-0020 | AM/PM | 25.000 | 15.000 | 15.000 | 15.000 | 15.000 | 10.000 |
| 252-US0001-0022 | AM/PM | 30.000 | 25.000 | 20.000 | 15.000 | 15.000 | 15.000 |
| 252-US0001-0026 | AM/PM | 25.000 | 25.000 | 25.000 | 20.000 | 20.000 | 5.000 |
| 252-US0001-0028 | AM/PM | 30.000 | | | | | |
| | Mean | 26.786 | 25.500 | 20.833 | 19.615 | 19.615 | 6.923 |
| | Standard Deviation | 2.486 | 4.378 | 4.174 | 4.312 | 4.312 | 5.220 |
| | Standard Error | 0.664 | 1.384 | 1.205 | 1.196 | 1.196 | 1.448 |
| | N | 14 | 10 | 12 | 13 | 13 | 13 |
| IMMEDIATE MINIMAL ERYTHEMA DOSE (MED) UVA EXPOSURE - PERIOD I/PM TREATMENT ||||||||
| 252-US0001-0003 | PM/AM | 25.000 | 30.000 | 30.000 | 30.000 | 30.000 | −5.000 |
| 252-US0001-0004 | PM/AM | 25.000 | NE(a) | NE(a) | 30.000 | 30.000 | −5.000 |
| 252-US0001-0006 | PM/AM | 25.000 | NE(a) | NE(a) | NE(a) | NE(a) | |
| 252-US0001-0007 | PM/AM | 25.000 | NE(a) | NE(a) | NE(a) | NE(a) | |
| 252-US0001-0009 | PM/AM | 30.000 | 25.000 | 30.000 | 25.000 | 25.000 | 5.000 |
| 252-US0001-0011 | PM/AM | 30.000 | NE(a) | NE(a) | NE(a) | NE(a) | |
| 252-7S0001-0015 | PM/AM | 30.000 | NE(a) | NE(a) | NE(a) | NE(a) | |
| 252-US0001-0016 | PM/AM | 30.000 | NE(a) | NE(a) | NE(a) | NE(a) | |
| 252-US0001-0018 | PM/AM | 30.000 | NE(a) | 30.000 | 30.000 | 30.000 | 0.000 |
| 252-US0001-0021 | PM/AM | 25.000 | NE(a) | NE(a) | 30.000 | 30.000 | −5.000 |
| 252-US0001-0023 | PM/AM | 30.000 | NE(a) | NE(a) | NE(a) | NE(a) | |
| 252-US0001-0024 | PM/AM | 30.000 | 30.000 | 30.000 | 30.000 | 30.000 | 0.000 |
| 252-US0001-0025 | PM/AM | 30.000 | NE(a) | NE(a) | 25.000 | 25.000 | 5.000 |
| 252-US0001-0027 | PM/AM | 30.000 | NE(a) | 30.000 | 30.000 | 30.000 | 0.000 |
| | Mean | 28.214 | 28.333 | 30.000 | 28.750 | 28.750 | −0.625 |
| | Standard Deviation | 2.486 | 2.887 | 0.000 | 2.315 | 2.315 | 4.173 |
| | Standard Error | 0.664 | 1.667 | 0.000 | 0.818 | 0.818 | 1.475 |
| | N | 14 | 3 | 5 | 8 | 8 | 8 |

TABLE 5

| SUBJECT ID | STUDY DRUG | BASELINE | 0 H | 3 H | 6 H | IMMEDIATE MED | CHANGE BASELINE |
|---|---|---|---|---|---|---|---|
| IMMEDIATE MINIMAL ERYTHEMA DOSE (MED) UVA/UVB EXPOSURE - PERIOD I/AM TREATMENT | | | | | | | |
| 252-US0001-0001 | AM/PM | 0.060 | 0.094 | 0.075 | 0.060 | 0.060 | 0.000 |
| 252-US0001-0002 | AM/PM | 0.094 | NE(a) | 0.075 | 0.075 | 0.075 | 0.019 |
| 252-US0001-0005 | AM/PM | 0.094 | NE(a) | 0.075 | 0.060 | 0.060 | 0.034 |
| 252-US0001-0008 | AM/PM | 0.094 | NE(a) | NE(a) | NE(a) | NE(a) | |
| 252-US0001-0010 | AM/PM | 0.094 | NE(a) | 0.075 | 0.075 | 0.075 | 0.019 |
| 252-US0001-0012 | AM/PM | 0.094 | NE(a) | 0.075 | 0.075 | 0.075 | 0.019 |
| 252-US0001-0013 | AM/PM | 0.094 | NE(a) | 0.094 | 0.094 | 0.094 | 0.000 |
| 252-US0001-0014 | AM/PM | 0.094 | NE(a) | NE(a) | NE(a) | NE(a) | |
| 252-US0001-0017 | AM/PM | 0.094 | NE(a) | NE(a) | 0.094 | 0.094 | 0.000 |
| 252-US0001-0019 | AM/PM | 0.075 | NE(a) | 0.075 | 0.075 | 0.075 | 0.000 |
| 252-US0001-0020 | AM/PM | 0.094 | NE(a) | 0.075 | 0.075 | 0.075 | 0.019 |
| 252-US0001-0022 | AM/PM | 0.118 | NE(a) | 0.148 | 0.118 | 0.118 | 0.000 |
| 252-US0001-0026 | AM/PM | 0.118 | NE(a) | NE(a) | 0.118 | 0.118 | 0.000 |
| 252-US0001-0028 | AM/PM | 0.094 | | | | | |
| | Mean | 0.094 | 0.094 | 0.087 | 0.084 | 0.084 | 0.010 |
| | Standard Deviation | 0.014 | | 0.026 | 0.020 | 0.020 | 0.012 |
| | Standard Error | 0.004 | | 0.009 | 0.006 | 0.006 | 0.004 |
| | N | 14 | 1 | 8 | 11 | 11 | 11 |
| IMMEDIATE MINIMAL ERYTHEMA DOSE (MED) UVA/UVB EXPOSURE - PERIOD I/PM TREATMENT | | | | | | | |
| 252-US0001-0003 | PM/AM | 0.094 | NE(a) | NE(a) | 0.094 | 0.094 | 0.000 |
| 252-US0001-0004 | PM/AM | 0.094 | NE(a) | NE(a) | NE(a) | NE(a) | |
| 252-US0001-0006 | PM/AM | 0.094 | NE(a) | NE(a) | NE(a) | NE(a) | |
| 252-US0001-0007 | PM/AM | 0.060 | NE(a) | NE(a) | NE(a) | NE(a) | |
| 252-US0001-0009 | PM/AM | 0.094 | NE(a) | NE(a) | NE(a) | NE(a) | |
| 252-US0001-0011 | PM/AM | 0.094 | NE(a) | NE(a) | 0.118 | 0.118 | −0.024 |
| 252-7S0001-0015 | PM/AM | 0.118 | NE(a) | NE(a) | NE(a) | NE(a) | |
| 252-US0001-0016 | PM/AM | 0.118 | NE(a) | NE(a) | NE(a) | NE(a) | |
| 252-US0001-0018 | PM/AM | 0.118 | NE(a) | 0.094 | 0.094 | 0.094 | 0.024 |
| 252-US0001-0021 | PM/AM | 0.094 | NE(a) | NE(a) | 0.148 | 0.148 | −0.054 |
| 252-US0001-0023 | PM/AM | 0.118 | NE(a) | NE(a) | 0.148 | 0.148 | −0.030 |
| 252-US0001-0024 | PM/AM | 0.118 | NE(a) | NE(a) | NE(a) | NE(a) | |
| 252-US0001-0025 | PM/AM | 0.118 | NE(a) | 0.148 | 0.118 | 0.118 | 0.000 |
| 252-US0001-0027 | PM/AM | 0.118 | NE(a) | NE(a) | 0.148 | 0.148 | −0.030 |
| | Mean | 0.104 | | 0.121 | 0.124 | 0.124 | −0.016 |
| | Standard Deviation | 0.017 | | 0.038 | 0.024 | 0.024 | 0.026 |
| | Standard Error | 0.005 | | 0.027 | 0.009 | 0.009 | 0.010 |
| | N | 14 | 0 | 2 | 7 | 7 | 7 |

TABLE 6

LOMEFLOXACIN PLASMA CONCENTRATIONS (mcg/ml)
LOMEFLOXACIN a.m. - PERIOD I

| | Subject Number | | | | | | | | | |
|---|---|---|---|---|---|---|---|---|---|---|
| Hour* | 1 | 2 | 5 | 8 | 10 | 12 | 13 | 14 | 17 | 19 |
| Predose | 0.000 | 0.000 | 0.000 | 0.000 | 0.000 | 0.000 | 0.000 | 0.000 | 0.000 | 0.000 |
| 0 | 1.160 | 1.160 | 1.060 | 1.540 | 1.520 | 1.350 | 0.901 | 1.370 | 1.080 | 1.180 |
| 2 | 0.786 | 1.030 | 0.889 | 1.460 | 1.360 | 1.030 | 0.711 | 1.090 | 0.840 | 0.915 |
| 14 | 0.271 | 0.368 | 0.243 | 0.385 | 0.479 | 0.297 | 0.210 | 0.350 | 0.204 | 0.279 |
| 16 | 2.920 | 2.420 | 3.160 | 3.730 | 3.000 | 3.660 | 2.650 | 2.840 | 2.950 | 3.050 |
| 19 | 1.850 | 1.710 | 1.810 | 2.370 | 2.360 | 2.280 | 1.780 | 2.060 | 1.750 | 1.720 |
| 38 | 0.230 | 0.318 | 0.281 | 0.346 | 0.467 | 0.319 | 0.251 | 0.361 | 0.201 | 0.157 |
| 62 | 0.039 | 0.064 | 0.027 | 0.054 | 0.073 | 0.035 | 0.027 | 0.053 | 0.021 | 0.016 |
| 86 | 0.011 | 0.016 | 0.006 | 0.013 | 0.019 | 0.007 | 0.009 | 0.017 | 0.000 | 0.000 |
| Cmax (ng/ml) | 2.920 | 2.420 | 3.160 | 3.730 | 3.000 | 3.660 | 2.650 | 2.840 | 2.950 | 3.050 |
| Tmax (hr) | 16 | 16 | 16 | 16 | 16 | 16 | 16 | 16 | 16 | 16 |
| AUC (mcg/hr) | 42.222 | 44.371 | 43.556 | 58.741 | 59.874 | 52.652 | 39.706 | 50.448 | 39.839 | 39.843 |

| | Subject Number | | | | | | | |
|---|---|---|---|---|---|---|---|---|
| Hour* | 20 | 22 | 26 | 28 | Mean | S.D. | S. Error | C.V. (%) |
| Predose | 0.000 | 0.000 | 0.000 | 0.000 | 0.0 | 0.0 | 0.0 | 0.0 |
| 0 | 1.520 | 1.720 | 1.360 | 1.800 | 1.3 | 0.3 | 0.1 | 19.6 |
| 2 | 1.200 | 1.280 | 1.110 | 1.500 | 1.1 | 0.2 | 0.1 | 22.9 |
| 14 | 0.317 | 0.283 | 0.419 | | 0.3 | 0.1 | 0.0 | 25.8 |

TABLE 6-continued

| | | | | | | | | |
|---|---|---|---|---|---|---|---|---|
| 16 | 2.940 | 4.040 | 2.580 | | 3.1 | 0.5 | 0.1 | 15.4 |
| 19 | 2.880 | 3.060 | 2.390 | | 2.2 | 0.4 | 0.1 | 20.8 |
| 38 | 0.258 | 0.263 | 0.367 | | 0.3 | 0.1 | 0.0 | 27.7 |
| 62 | 0.036 | 0.027 | 0.042 | | 0.0 | 0.0 | 0.0 | 43.3 |
| 86 | 0.006 | 0.008 | 0.008 | | 0.0 | 0.0 | 0.0 | 64.0 |
| Cmax (ng/ml) | 2.940 | 4.040 | 2.580 | 1.800 | 3.0 | 0.6 | 0.2 | 19.0 |
| Tmax (hr) | 16 | 16 | 16 | 0 | 14.9 | 4.3 | 1.1 | 28.8 |
| AUC (mcg/hr) | 57.652 | 62.820 | 53.798 | 12.300 | 47.0 | 12.9 | 3.4 | 27.4 |

*The hour refers to sample collection times as described hereinabove. For the a.m. dosing group, the following would be the actual time of collection in relation to final active dose.
Predose = Pre-study plasma sample
Hour 0 = Day 4 14-hours prior to last active dose
Hour 2 = Day 4 12-hours prior to last active dose
Hour 14 = Day 5 immediately prior to last active dose
Hour 16 = Day 5 2-hours following last active dose
Hour 19 = Day 5 5-hours following last active dose
Hour 38 = Day 6 24-hours following last active dose
Hour 62 = Day 7 48-hours following last active dose
Hour 86 = Day 8 72-hours following last active dose LOMEFLOXACIN PLASMA CONCENTRATIONS (mcg/ml)
LOMEFLOXACIN PM - PERIOD I

| | Subject Number | | | | | | | | | |
|---|---|---|---|---|---|---|---|---|---|---|
| Hour* | 3 | 4 | 6 | 7 | 9 | 11 | 15 | 16 | 18 | 21 |
| Predose | 0.000 | 0.000 | 0.000 | 0.000 | 0.000 | 0.000 | 0.000 | 0.000 | 0.000 | 0.000 |
| 0 | 0.534 | 0.681 | 0.641 | 0.224 | 0.388 | 0.332 | 0.334 | 0.304 | 0.245 | 0.191 |
| 2 | 3.410 | 0.499 | 3.500 | 3.540 | 2.920 | 1.960 | 2.970 | 2.200 | 3.170 | 4.320 |
| 14 | 0.995 | 1.380 | 1.380 | 0.813 | 1.010 | 0.782 | 0.823 | 0.925 | 0.660 | 0.833 |
| 16 | 0.842 | 1.190 | 1.040 | 0.575 | 0.804 | 0.689 | 0.700 | 0.727 | 0.592 | 0.665 |
| 19 | 0.626 | 0.941 | 0.983 | 0.440 | 0.765 | 0.547 | 0.565 | 0.556 | 0.401 | 0.397 |
| 38 | 0.143 | 0.251 | 0.159 | 0.048 | 0.134 | 0.093 | 0.115 | 0.091 | 0.044 | 0.041 |
| 62 | 0.029 | 0.059 | 0.037 | 0.007 | 0.026 | 0.014 | 0.018 | 0.014 | 0.009 | 0.010 |
| 86 | 0.007 | 0.020 | 0.014 | 0.000 | 0.006 | 0.000 | 0.000 | 0.000 | 0.000 | 0.000 |
| Cmax (ng/ml) | 3.410 | 1.380 | 3.500 | 3.540 | 2.920 | 1.960 | 2.970 | 2.200 | 3.170 | 4.320 |
| Tmax (hr) | 2 | 14 | 2 | 2 | 2 | 2 | 2 | 2 | 2 | 2 |
| AUC (mcg/hr) | 44.215 | 34.213 | 52.689 | 38.173 | 41.900 | 29.601 | 37.755 | 32.405 | 34.108 | 43.413 |

| | Subject Number | | | | | | | |
|---|---|---|---|---|---|---|---|---|
| Hour* | 23 | 24 | 25 | 27 | Mean | S.D. | S. Error | C.V. (%) |
| Predose | 0.000 | 0.000 | 0.000 | 0.000 | 0.0 | 0.0 | 0.0 | 0.0 |
| 0 | 0.464 | 0.242 | 0.735 | 0.464 | 0.4 | 0.2 | 0.0 | 43.3 |
| 2 | 4.620 | 0.911 | 2.410 | 3.790 | 2.9 | 1.2 | 0.3 | 41.2 |
| 14 | 1.560 | 0.726 | 1.170 | 1.220 | 1.0 | 0.3 | 0.1 | 27.4 |
| 16 | 1.210 | 0.564 | 1.040 | 0.890 | 0.8 | 0.2 | 0.1 | 26.8 |
| 19 | 0.828 | 0.390 | 0.865 | 0.738 | 0.6 | 0.2 | 0.1 | 32.1 |
| 38 | 0.142 | 0.061 | 0.183 | 0.142 | 0.1 | 0.1 | 0.0 | 50.9 |
| 62 | 0.033 | 0.008 | 0.043 | 0.029 | 0.0 | 0.0 | 0.0 | 64.3 |
| 86 | 0.019 | 0.000 | 0.008 | 0.011 | 0.0 | 0.0 | 0.0 | 122 |
| Cmax (ng/ml) | 4.620 | 0.911 | 2.410 | 3.790 | 2.9 | 1.1 | 0.3 | 36.3 |
| Tmax (hr) | 2 | 2 | 2 | 2 | 2.9 | 3.2 | 0.9 | 112 |
| AUC (mcg/hr) | 59.930 | 18.905 | 42.973 | 49.758 | 40.0 | 10.3 | 2.8 | 25.8 |

*The hour refers to sample collection times as described hereinabove. For the p.m. dosing group, the following would be the actual time of collection in relation to final active dose.
Predose = Pre-study plasma sample
Hour 0 = Day 4 immediately prior to last active dose
Hour 2 = Day 4 2-hours prior to last active dose
Hour 14 = Day 5 14-hours prior to last active dose
Hour 16 = Day 5 16-hours following last active dose
Hour 19 = Day 5 19-hours following last active dose
Hour 38 = Day 6 38-hours following last active dose
Hour 62 = Day 7 62-hours following last active dose
Hour 86 = Day 8 86-hours following last active dose

TABLE 7

NUMBER OF SUBJECTS WITH SCORE >=2

| SCHEDULED EVALUATION TIME | TREATMENT | COUNT | PERCENT* |
|---|---|---|---|
| PERIOD I - UVA | | | |
| BL | a.m. | 0 | 0.00 |
| BL | p.m. | 0 | 0.00 |
| 0 | a.m. | 1 | 7.69 |
| 0 | p.m. | 0 | 0.00 |
| 3 | a.m. | 6 | 46.15 |
| 3 | p.m. | 0 | 0.00 |
| 6 | a.m. | 9 | 69.23 |
| 6 | p.m. | 0 | 0.00 |
| 24 | a.m. | 5 | 38.46 |
| 24 | p.m. | 0 | 0.00 |
| 48 | a.m. | 2 | 15.38 |
| 48 | p.m. | 0 | 0.00 |
| 72 | a.m. | 0 | 0.00 |
| 72 | p.m. | 0 | 0.00 |
| PERIOD I - UVA & UVB | | | |
| BL | a.m. | 2 | 15.38 |
| BL | p.m. | 1 | 7.69 |
| 0 | a.m. | 0 | 0.00 |
| 0 | p.m. | 0 | 0.00 |
| 3 | a.m. | 0 | 0.00 |
| 3 | p.m. | 0 | 0.00 |
| 6 | a.m. | 2 | 15.38 |
| 6 | p.m. | 0 | 0.00 |
| 24 | a.m. | 0 | 0.00 |
| 24 | p.m. | 1 | 7.69 |
| 48 | a.m. | 0 | 0.00 |
| 48 | p.m. | 0 | 0.00 |
| 72 | a.m. | 0 | 0.00 |
| 72 | p.m. | 0 | 0.00 |

*N-13 This represents all subjects who had their irradiated sites graded regardless of having an established MED.
**BL Baseline The foregoing examples are provided to enable one of ordinary skill in the art to practice the present invention. These examples are merely illustrative, however, and should not be read as limiting the scope of the invention as it is claimed in the appended claims.

While the present invention has been described herein with some specificity, and with reference to certain preferred embodiments thereof, those of ordinary skill in the art will recognize numerous variations, modifications and substitutions of that which has been described which can be made, and which are within the scope and spirit of the invention. For example, numerous and varied over-the-counter and prescription medications, and doses of such medications, other than those set forth hereinabove may be employed in the methods of the present invention. Further, other modes of administration than those described herein may be employed in the methods of the present invention. It is intended therefore that all of these modifications and variations be within the scope of the present invention as described and claimed herein, and that the claims which follow be interpreted as broadly as is reasonable.

What is claimed is:

1. A method for preventing or reducing a photosensitivity and/or phototoxicity reaction caused by a once-a-day dose of an anti-infection medication which causes such a reaction in a patient, comprising administering said medication to said patient between the hours of about 4:00 p.m. and about 12:00 a.m., provided said anti-infection medication is not lomefloxacin hydrochloride.

2. The method of claim 1 wherein said medication is administered between the hours of about 5:00 p.m. and about 10:00 p.m.

3. The method of claim 2 wherein said medication is administered between the hours of about 5:30 p.m. and about 7:30 p.m.

4. The method of claim 1 wherein said medication is isotretinoin; chlortetracycline hydrochloride; the monohydrochloride of (4S-(4a,4aα,5aα,6β,12aα,))-4-(dimethylamino)-1,4,4a,5,5a,6,11,12a-octahydro-3,6,10,12,12a-pentahydroxy-6-methyl-1,11-dioxo-2-naphthacenecarboxamide; human leukocyte derived interferon α-n3; flucytosine; sulfamethoxazole and phenazopyridine hydrochloride; sulfisoxazole and phenazopyridine hydrochloride; trimethoprim and sulfamethoxazole; norfloxacin; ciprofloxacin; (4-4' diaminodiphenylsulfone; (4S-(4a,4aα,5aα,6β,12aα))-7-Chloro-4-(dimethylamino)-1,4,4a,5,5a,6,11,12a-octahydro-3,6,10,12,12a-pentahydroxy-1,11-dioxo-2-naphthacenecarboxamide monohydrochloride; doxycycline hyclate; N1-(5,6-dimethoxy-4-pyrimidinyl) sulfanilamide (sulfadoxine) and 2,4-diamino-5-(p-chlorophenyl)-6-ethylpyrimidine (pyrimethamine); ofloxacin; griseofulvin; sulfamethoxazole; sulfisoxazole; chlorhexidine gluconate; recombinant interferon α-2b; clofazimine; (4S-(4a,4aα,5aα,12aα))-4,7-bis(dimethylamino)-1,4,4a,5,5a,6,11,12a-octahydro-3,10,12,12a-tetrahydroxy-1,11-dioxo-2-naphthacenecarboxamide monohydrochloride; doxycycline monohydrate; nalidixic acid; hexachlorophene; erythromycin ethylsuccinate, USP and sulfisoxazole acetyl, US; enoxacin; trimethoprim sulfate and polymyxin B sulfate; pyrazinamide; trimethoprim and sulfamethoxazole; amantadine hydrochloride; chlorprothixene; oxytetracycline; sulfamethizole; sulfacetamide; doxycycline monohydrate; oxytetracycline; or anzithromycin.

5. The method of claim 4 wherein said medication is administered between the hours of about 5:00 p.m. and about 10:00 p.m.

6. The method of claim 5 wherein said medication is administered between the hours of about 5:30 p.m. and about 7:30 p.m.

7. The method of claim 4 wherein said medication is an orally-administered medication selected from isotretinoin; the monohydrochloride of (4S-(4α,4aα,5aα,6β,12aα,))-4-(dimethylamino)-1,4,4a,5,5a,6,11,12a-octahydro-3,6,10,12,12a-pentahydroxy-6-methyl-1,11-dioxo-2-naphthacenecarboxamide; sulfamethoxazole and phenazopyridine hydrochloride; sulfisoxazole and phenazopyridine hydrochloride; trimethoprim and sulfamethoxazole; norfloxacin; ciprofloxacin; (4-4' diaminodiphenylsulfone; oxaproxin; (4S-(4α,4aα,5aα,6β,12aα))-7-Chloro-4-(dimethylamino)-1,4,4a,5,5a,6,11,12a-octahydro-3,6,10,12,12a-pentahydroxy-1,11-dioxo-2-naphthacenecarboxamide monohydrochloride; doxycycline hyclate; N1-(5,6-dimethoxy-4-pyrimidinyl) sulfanilamide (sulfadoxine) and 2,4-diamino-5-(p-chlorophenyl)-6-ethylpyrimidine (pyrimethamine); griseofulvin; sulfamethoxazole; sulfisoxazole; clofazimine; (4S-(4α,4aα,5aα,12aα))-4,7-bis(dimethylamino)-1,4,4a,5,5a,6,11,12a-octahydro-3,10,12,12a-tetrahydroxy-1,11-dioxo-2-naphthacenecarboxamide monohydrochloride; doxycycline monohydrate; nalidixic acid; erythromycin ethylsuccinate, USP and sulfisoxazole acetyl, USP; pyrazinamide; trimethoprim and sulfamethoxazole; amantadine hydrochloride; sulfamethizole; doxycycline monohydrate; oxytetracycline; and azithromycin.

8. The method of claim 7 wherein said medication is administered between the hours of about 5:00 p.m. and about 10:00 p.m.

9. The method of claim 8 wherein said medication is administered between the hours of about 5:30 p.m. and about 7:30 p.m.

10. The method of claim 1 wherein said medication is a quinolone antibiotic selected from amifloxacin, cinoxacin, ciprofloxacin, difloxacin, enoxacin, fleroxacin, flumequine, milaxacin, nalidixic acid, norfloxacin, oflaxacin, oxolinic acid, peflaxacin, pipemidic acid, piromidic acid, rosoxacin, temefloxacin and tosuflaxacin, or the pharmaceutically-acceptable salt thereof.

11. The method of claim 10 wherein said medication is administered between the hours of about 5:00 p.m. and about 10:00 p.m.

12. The method of claim 11 wherein said medication is administered between the hours of about 5:30 p.m. and about 7:30 p.m.

13. The method of claim 1 wherein said medication is a sulfonamide antibiotic selected from acetyl sulfamethoxypyrazine, acetyl sulfisoxazole, azosulfamide, benzylsulfamide, chloramine-B, chloramine-T, dichloramine T, formosulfathiazole, $N^2$-Formylsulfisomidine, $N^4$-β-D-glucosylsulfanilamide, mafenide, 4'-(methylsulfamoyl) sulfanilanilide, p-nitrosulfathiazole, noprylsulfamide, phthalylsulfacetamide, phthalylsulfathiazole, salazosulfadimide, succinylsulfathiazole sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicylic acid, $N^4$-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasolazine, sulfasomizole, sulfasymazine, sulfathiazole, sulfathiourea, sulfatolamide, sulfisomidine and sulfisoxazole.

14. The method of claim 13 wherein said medication is administered between the hours of about 5:00 p.m. and about 10:00 p.m.

15. The method of claim 14 wherein said medication is administered between the hours of about 5:30 p.m. and about 7:30 p.m.

16. The method of claim 1 wherein said medication is a tetracycline antibiotic selected from apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin and tetracycline.

17. The method of claim 16 wherein said medication is administered between the hours of about 5:00 p.m. and about 10:00 p.m.

18. The method of claim 17 wherein said medication is administered between the hours of about 5:30 p.m. and about 7:30 p.m.

19. In a method for administering a therapeutically effective amount of a once-a-day anti-infection medication which medication in such a once-a-day therapeutic amount achieves a concentration in the blood which causes a photosensitivity and/or phototoxicity reaction in the patient to whom the medication is administered, an improvement in the method comprising administering said medication to the patient at a time sufficient for the blood level of said medication to be at a concentration which is less than a concentration which produces a photosensitivity and/or phototoxicity reaction between the hours of about 6:00 a.m. and about 7:00 p.m., provided said anti-infection medication is not lomefloxacin hydrochloride.

20. The method of claim 19 wherein said medication is administered between the hours of about 5:00 p.m. and about 10:00 p.m.

21. The method of claim 20 wherein said medication is administered between the hours of about 5:30 p.m. and about 7:30 p.m.

22. The method of claim 1 wherein said medication is isotretinoin; chlortetracycline hydrochloride; the monohydrochloride of (4S-4α,4aα,5aα,6β,12aα,))-4-(dimethylamino)-1,4,4a,5,5a,6,11,12a-octahydro-3,6,10,12,12a-pentahydroxy-6-methyl-1,11-dioxo-2-naphthacenecarboxamide; humanleukocyte derived interferon α-n3; flucytosine; sulfamethoxazole and phenazopyridine hydrochloride; sulfisoxazole and phenazopyridine hydrochloride; trimethoprim and sulfamethoxazole; norfloxacin; ciprofloxacin; (4-4' diaminodiphenylsulfone; (4S-(4α,4aα,5aα,6β,12aα))-7-Chloro-4-(dimethylamino)-1,4,4a,5,5a,6,11,12a-octahydro-3,6,10,12,12a-pentahydroxy-1,11-dioxo-2-naphthacenecarboxamide monohydrochloride; doxycycline hyclate; N1-(5,6-dimethoxy-4-pyrimidinyl) sulfanilamide (sulfadoxine) and 2,4-diamino-5-(p-chlorophenyl)-6-ethylpyrimidine (pyrimethamine); ofloxacin; griseofulvin; sulfamethoxazole; sulfisoxazole; chlorhexidine gluconate; recombinant interferon α-2b; clofazimine; (4S-(4α,4aα,5aα,12aα))-4,7,-bis(dimethylamino)-1,4,4a,5,5a,6,11,12a-octahydro-3,10,12,12a-tetrahydroxy-1,11-dioxo-2-naphthacenecarboxamide monohydrochloride; doxycycline monohydrate; nalidixic acid; hexachlorophene; erythromycin ethylsuccinate, USP and sulfisoxazole acetyl, USP; enoxacin; trimethoprim sulfate and polymyxin B sulfate; pyrazinamide; trimethoprim and sulfamethoxazole; amantadine hydrochloride; oxytetracycline; sulfamethizole; sulfacetamide sodium-phenylephrine hydrochloride; doxycycline monohydrate; oxytetracycline; or anzithromycin.

23. The method of claim 22 wherein said medication is administered between the hours of about 5:00 p.m. and about 10:00 p.m.

24. The method of claim 23 wherein said medication is administered between the hours of about 5:30 p.m. and about 7:30 p.m.

25. The method of claim 4 wherein said medication is an orally-administered medication selected from isotretinoin; the monohydrochloride of (4S-(4α,4aα,5aα,6β,12aα,))-4-(dimethylamino)-1,4,4a,5,5a,6,11,12a-octahydro-3,6,10,12,12a-pentahydroxy-6-methyl-1,11-dioxo-2-naphthacenecarboxamide; sulfamethoxazole and phenazopyridine hydrochloride; sulfisoxazole and phenazopyridine hydrochloride; trimethoprim and sulfamethoxazole; norfloxacin; ciprofloxacin; (4-4' diaminodiphenylsulfone; oxaproxin; (4S-(4α,4aα,5aα,6β,12aα))-7-Chloro-4-(dimethylamino)-1,4,4a,5,5a,6,11,12a-octahydro-3,6,10,12,12a-pentahydroxy-1,11-dioxo-2-naphthacenecarboxamide monohydrochloride; doxycycline hyclate; N1-(5,6-dimethoxy-4-pyrimidinyl) sulfanilamide (sulfadoxine) and 2,4-diamino-5-(p-chlorophenyl)-6-ethylpyrimidine (pyrimethamine); cyclobenzaprine hydrochloride; griseofulvin; sulfamethoxazole; sulfisoxazole; clofazimine; (4S-(4α,4aα,5aα,12aα))-4,7-bis(dimethylamino)-1,4,4a,5,5a,6,11,12a-octahydro-3,10,12,12a-tetrahydroxy-1,11-dioxo-2-naphthacenecarboxamide monohydrochloride; doxycycline monohydrate; nalidixic acid; erythromycin ethylsuccinate, USP and sulfisoxazole acetyl, USP; pyrazinamide; trimethoprim and sulfamethoxazole; amantadine hydrochloride; sulfamethizole; doxycycline monohydrate; oxytetracycline; and azithromycin.

26. The method of claim 25 wherein said medication is administered between the hours of about 5:00 p.m. and about 10:00 p.m.

27. The method of claim 26 wherein said medication is administered between the hours of about 5:30 p.m. and about 7:30 p.m.

28. The method of claim 19 wherein said medication is a quinoline antibiotic selected from amifloxacin, cioxacin, ciprofloxacin, difloxacin, enoxacin, fleroxacin, flumequine, miloxacin, nalidixic acid, norloxacin, ofloxacin, oxolinic acid, perfloxacin, pipemidic acid, piromidic acid, rosoxacin, temafloxacin and tosufloxacin, or the pharmaceutically-acceptable salt thereof.

29. The method of claim 28 wherein said medication is administered between the hours of about 5:00 p.m. and about 10:00 p.m.

30. The method of claim 29 wherein said medication is administered between the hours of about 5:30 p.m. and about 7:30 p.m.

31. The method of claim 19 wherein said medication is a sulfonamide antibiotic selected from acetyl sulfamethoxypyrazine, acetyl sulfisoxazole, azosulfamide, benzylsulfamide, chloramine-B, chloramine-T, dichloramine T, formosulfathiazole, $N^2$-Formylsulfisomidine, $N^4$-β-D-glucosylsulfanilamide, mafenide, 4'-(methylsulfamoyl) sulfanilanilide, p-nitrosulfathiazole, noprylsulfamide, phthalylsulfacetamide, phthalylsulfathiazole, salazosulfadimide, succinylsulfathiazole sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicylic acid, $N^4$-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasolazine, sulfasomizole, sulfasymazine, sulfathiazole, sulfathiourea, sulfatolamide, sulfisomidine and sulfisoxazole.

32. The method of claim 31 wherein said medication is administered between the hours of about 5:00 p.m. and about 10:00 p.m.

33. The method of claim 32 wherein said medication is administered between the hours of about 5:30 p.m. and about 7:30 p.m.

34. The method of claim 19 wherein said medication is a tetracycline antibiotic selected from apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin and tetracycline.

35. The method of claim 34 wherein said medication is administered between the hours of about 5:00 p.m. and about 10:00 p.m.

36. The method of claim 35 wherein said medication is administered between the hours of about 5:30 p.m. and about 7:30 p.m.

37. An article of manufacture comprising:
(1) a packaging material, and
(2) a once-a-day dose of an anti-infection medication which causes a photosensitivity and/or a phototoxicity reaction contained within said packaging material,
wherein such reaction is prevented or reduced by administering said medication between the hours of about 4:00 p.m. and about 12:00 a.m., and wherein said packaging material comprises a label which indicates that such reaction is prevented or reduced by administering said medication between the hours of about 4:00 p.m. and about 12:00 a.m., and/or that such medication is to be administered between the hours of about 4:00 p.m. and about 12:00 a.m., and/or wherein said packaging material is arranged in a manner which releases said medication to said patient between the hours of about 4:00 p.m. and about 12:00 a.m., provided said anti-infection medication is not lomefloxacin hydrochloride.

38. The article of manufacture of claim 37 wherein said medication is administered between the hours of about 5:00 p.m. and about 10:00 p.m.

39. The article of manufacture of claim 38 wherein said medication is administered between the hours of about 5:30 p.m. and about 7:30 p.m.

40. The article of manufacture of claim 37 wherein said medication is isotretinoin; chlortetracycline hydrochloride; the monohydrochloride of (4S-(4a,4aα,5aα,6β,12aα))-4-(dimethylamino)-1,4,4a,5,5a,6,11,12a-octahydro-3,6,10,12,12a-pentahydroxy-6-methyl-1,11-dioxo-2-naphthacenecarboxamide; human leukocyte derived interferon α-n3; sulfamethoxazole and phenazopyridine hydrochloride; sulfisoxazole and phenazopyridine hydrochloride; trimethoprim and sulfamethoxazole; norflaxacin; ciprofloxacin; (4-4' diaminodiphenylsulfone; oxaproxin; (4S-(4α,4aα,5aα,6β, 12aα))-7-Chloro-4-(dimethylamino)-1,4,4a,5,5a,6,11,12a-octahydro-3,6,10,12,12a-pentahydroxy-1,11-dioxo-2-naphthacenecarboxamide monohydrochloride; doxycycline hyclate; N1-(5,6-dimethoxy-4-pyrimidinyl) sulfanilamide (sulfadoxine) and 2,4-diamino-5-(p-chlorophenyl)-6-ethylpyrimidine (pyrimethamine); ofloxacin; griseofulvin; sulfamethoxazole; sulfisoxazole; chlorhexidine gluconate; recombinant interferon a-2b; clofazimine; (4S-(4α,4aα,5aα, 12aα))-4,7-bis(dimethylamino)-1,4,4a,5,5a,6,11,12a-octahydro-3,10,12,12a-tetrahydroxy-1,11-dioxo-2-naphthacenecarboxamide monohydrochloride; doxycycline monohydrate; nalidixic acid; hexachlorophene; erythromycin ethylsuccinate, USP and sulfisoxazole acetyl, USP; enoxacin; trimethoprim sulfate and polymyxin B sulfate; pyrazinamide; trimethoprim and sulfamethoxazole; amantadine hydrochloride; chlorprothixene; oxytetracycline; sulfamethizole; sulfacetamide; doxycycline monohydrate; oxytetracycline or anzithromycin.

41. The article of manufacture of claim 40 wherein said medication is administered between the hours of about 5:00 p.m. and about 10:00 p.m.

42. The article of manufacture of claim 41 wherein said medication is administered between the hours of about 5:30 p.m. and about 7:30 p.m.

43. The method of claim 40, wherein said medication is an orally-administered medication selected from isotretinoin; the monohydrochloride of (4S-(4α,4aα,5aα,6β, 12aα,))-4-(dimethylamino)-1,4,4a,5,5a,6,11,12a-octahydro-3,6,10,12,12a-pentahydroxy-6-methyl-1,11-dioxo-2-naphthacene-carboxamide; sulfamethoxazole and phenazopyridine hydrochloride; sulfisoxazole and phenazopyridine hydrochloride; trimethoprim and sulfamethoxazole; norfloxacin; ciprofloxacin; (4-4' diaminodiphenylsulfone; oxaproxin; (4S-(4α,4aα,5aα,6β,12aα))-7-Chloro-4-(dimethylamino)-1,4,4a,5,5a,6,11,12a-octahydro-3,6,10,12,12a-pentahydroxy-1,11-dioxo-2-naphthacenecarboxamide monohydrochloride; doxycycline hyclate; N1-(5,6-dimethoxy-4-pyrimidinyl) sulfanilamide (sulfadoxine) and 2,4-diamino-5-(p-chlorophenyl)-6-ethylpyrimidine (pyrimethamine); griseofulvin; sulfamethoxazole; sulfisoxazole; clofazimine; (4S-(4α,4aα, 5aα,12aα))-4,7-bis(dimethylamino)-1,4,4a,5,5a,6,11,12a-octahydro-3,10,12,12a-tetrahydroxy-1,11-dioxo-2-naphthacenecarboxamide monohydrochloride; doxycycline monohydrate; nalidixic acid; erythromycin ethylsuccinate, USP and sulfisoxazole acetyl, USP; pyrazinamide; trimethoprim and sulfamethoxazole; amantadine hydrochloride; sulfamethizole; doxycycline monohydrate; oxytetracycline; and azithromycin.

44. The article of manufacture of claim 43 wherein said medication is administered between the hours of about 5:00 p.m. and about 10:00 p.m.

45. The article of manufacture of claim 44 wherein said medication is administered between the hours of about 5:30 p.m. and about 7:30 p.m.

46. The article of manufacture of claim 37 wherein said medication is a quinoline antibiotic selected from amifloxacin, cioxacin, ciprofloxacin, difloxacin, enoxacin, fleroxacin, flumequine, miloxacin, nalidixic acid, norloxacin, ofloxacin, oxolinic acid, perfloxacin, pipemidic acid, piromidic acid, rosoxacin, temafloxacin and tosufloxacin, or the pharmaceutically-acceptable salt thereof.

47. The article of manufacture of claim 46 wherein said medication is administered between the hours of about 5:00 p.m. and about 10:00 p.m.

48. The article of manufacture of claim 47 wherein said medication is administered between the hours of about 5:30 p.m. and about 7:30 p.m.

49. The article of manufacture of claim 37 wherein said medication is a sulfonamide antibiotic selected from acetyl sulfamethoxypyrazine, acetyl sulfisoxazole, azosulfamide, benzylsulfamide, chloramine-B, chloramine-T, dichloramine T, formosulfathiazole, $N^2$-Formylsulfisomidine, $N^4$-β-D-glucosylsulfanilamide, mafenide, 4'-(methylsulfamoyl) sulfanilanilide, p-nitrosulfathiazole, noprylsulfamide, phthalylsulfacetamide, phthalylsulfathiazole, salazosulfadimide, succinylsulfathiazole sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, sulfanilamidomethanesulfonic acid triethanolamine salt, 4-sulfanilamidosalicylic acid, $N^4$-sulfanilylsulfanilamide, sulfanilylurea, N-sulfanilyl-3,4-xylamide, sulfanitran, sulfaperine, sulfaphenazole, sulfaproxyline, sulfapyrazine, sulfapyridine, sulfasolazine, sulfasomizole, sulfasymazine, sulfathiazole, sulfathiourea, sulfatolamide, sulfisomidine and sulfisoxazole.

50. The article of manufacture of claim 49 wherein said medication is administered between the hours of about 5:00 p.m. and about 10:00 p.m.

51. The article of manufacture of claim 50 wherein said medication is administered between the hours of about 5:30 p.m. and about 7:30 p.m.

52. The article of manufacture of claim 37 wherein said medication is a tetracycline antibiotic selected from apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, senociclin and tetracycline.

53. The article of manufacture of claim 52 wherein said medication is administered between the hours of about 5:00 p.m. and about 10:00 p.m.

54. The article of manufacture of claim 53 wherein said medication is administered between the hours of about 5:30 p.m. and about 7:30 p.m.

* * * * *